US006773922B2

(12) United States Patent
Jeng et al.

(10) Patent No.: US 6,773,922 B2
(45) Date of Patent: Aug. 10, 2004

(54) REAGENTLESS ANALYSIS OF BIOLOGICAL SAMPLES

(75) Inventors: Tzyy-Wen Jeng, Vernon Hills, IL (US); Larry L. McDowell, Beach Park, IL (US); Joseph Larry Pezzaniti, Round Lake, IL (US); Gary M. Oosta, Gurnee, IL (US); Eric B. Shain, Glencoe, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/191,148

(22) Filed: Jul. 9, 2002

(65) Prior Publication Data

US 2003/0048432 A1 Mar. 13, 2003

Related U.S. Application Data

(62) Division of application No. 09/407,716, filed on Sep. 28, 1999, now Pat. No. 6,426,045, which is a division of application No. 09/141,483, filed on Aug. 27, 1998, now Pat. No. 6,087,182.

(51) Int. Cl.$^7$ ............................................. G01N 21/41
(52) U.S. Cl. ..................... 436/66; 436/86; 436/95; 436/98; 436/108; 436/97; 436/164; 436/165
(58) Field of Search ................................ 356/244, 246, 356/72, 73; 436/108, 97, 165, 66, 67, 95, 98, 86–90, 164, 171, 172

(56) References Cited

U.S. PATENT DOCUMENTS

| | | | |
|---|---|---|---|
| 2,413,208 A | | 12/1946 | Barnes |
| 2,483,102 A | | 9/1949 | Pierson |
| 3,090,222 A | | 5/1963 | Akaboshi et al. |
| 3,560,161 A | | 2/1971 | Webb et al. |
| 3,638,640 A | | 2/1972 | Shaw |
| 3,713,780 A | | 1/1973 | Shapiro |
| 4,027,971 A | | 6/1977 | Kolman |
| 4,256,403 A | * | 3/1981 | Powell ........................ 356/73 |
| 4,381,895 A | | 5/1983 | Hughes et al. |
| 4,427,889 A | | 1/1984 | Muller |
| 4,616,927 A | * | 10/1986 | Phillips et al. .............. 356/338 |
| 4,622,298 A | | 11/1986 | Mansour et al. |
| 4,681,443 A | | 7/1987 | Bach et al. |
| 4,710,025 A | * | 12/1987 | Wyatt et al. ................. 356/343 |
| 4,710,643 A | | 12/1987 | Schmukler et al. |
| 4,756,884 A | * | 7/1988 | Hillman et al. .............. 422/73 |
| 4,935,875 A | | 6/1990 | Shah et al. |
| 5,015,091 A | | 5/1991 | Suzuki et al. |
| 5,046,846 A | | 9/1991 | Ray et al. |
| 5,110,205 A | | 5/1992 | Suzuki et al. |
| 5,141,310 A | | 8/1992 | Boiarski |
| 5,159,642 A | | 10/1992 | Kosaka |
| 5,242,602 A | | 9/1993 | Richardson et al. |
| 5,247,340 A | | 9/1993 | Ogino |
| 5,267,151 A | | 11/1993 | Ham et al. |
| 5,291,426 A | | 3/1994 | Collins et al. |
| 5,296,911 A | | 3/1994 | Weyrauch et al. |
| 5,305,071 A | * | 4/1994 | Wyatt ........................... 356/73 |
| 5,313,406 A | | 5/1994 | Kauppinen et al. |
| 5,322,165 A | | 6/1994 | Melker et al. |
| 5,348,003 A | | 9/1994 | Caro |
| 5,377,674 A | | 1/1995 | Kuestner |
| 5,426,499 A | | 6/1995 | Kosaka et al. |
| 5,436,717 A | | 7/1995 | Ogino |
| 5,446,681 A | | 8/1995 | Gethner et al. |
| 5,448,349 A | | 9/1995 | Kosaka |
| 5,449,622 A | | 9/1995 | Yabe et al. |
| 5,457,526 A | | 10/1995 | Kosaka |
| 5,457,535 A | | 10/1995 | Schmidtke et al. |
| 5,469,251 A | | 11/1995 | Kosaka et al. |
| 5,481,113 A | | 1/1996 | Dou et al. |
| 5,488,469 A | | 1/1996 | Yamamoto et al. |
| 5,500,372 A | | 3/1996 | Kell |
| 5,511,558 A | | 4/1996 | Shepard et al. |
| 5,517,870 A | | 5/1996 | Kurimura et al. |
| 5,589,932 A | | 12/1996 | Garcia-Rubio et al. |
| 5,592,402 A | | 1/1997 | Beebe et al. |
| 5,594,544 A | | 1/1997 | Horiuchi et al. |
| 5,596,401 A | | 1/1997 | Kusuzawa |
| 5,602,038 A | | 2/1997 | Kell |
| 5,633,503 A | | 5/1997 | Kosaka |
| 5,696,580 A | | 12/1997 | Kubo et al. |

(List continued on next page.)

FOREIGN PATENT DOCUMENTS

| | | |
|---|---|---|
| EP | 0035081 | 9/1981 |
| EP | 0201824 | 11/1986 |
| EP | 0334536 | 9/1989 |
| EP | 0337173 | 10/1989 |

(List continued on next page.)

OTHER PUBLICATIONS

Voswinckel, Peter, Kidney International, vol. 46, Suppl. 47 (1994) pp. S–3–S–7, "A marvel of colors and ingredients. The story of urine test strips".

(List continued on next page.)

Primary Examiner—Jeffrey R. Snay
(74) Attorney, Agent, or Firm—David L. Weinstein

(57) ABSTRACT

Apparatus and method for determining at least one parameter, e.g., concentration, of at least one analyte, e.g., urea, of a biological sample, e.g., urine. A biological sample particularly suitable for the apparatus and method of this invention is urine. In general, spectroscopic measurements can be used to quantify the concentrations of one or more analytes in a biological sample. In order to obtain concentration values of certain analytes, such as hemoglobin and bilirubin, visible light absorption spectroscopy can be used. In order to obtain concentration values of other analytes, such as urea, creatinine, glucose, ketones, and protein, infrared light absorption spectroscopy can be used. The apparatus and method of this invention utilize one or more mathematical techniques to improve the accuracy of measurement of parameters of analytes in a biological sample. The invention also provides an apparatus and method for measuring the refractive index of a sample of biological fluid while making spectroscopic measurements substantially simultaneously.

15 Claims, 28 Drawing Sheets

U.S. PATENT DOCUMENTS

| | | | |
|---|---|---|---|
| 5,706,208 A | | 1/1998 | Osten |
| 5,772,606 A | | 6/1998 | Ashibe et al. |
| 5,776,783 A | | 7/1998 | Kell |
| 5,796,476 A | | 8/1998 | Wang et al. |
| 5,815,260 A | * | 9/1998 | Dou et al. ................. 356/301 |
| 5,838,008 A | | 11/1998 | Esler et al. |
| 6,118,520 A | * | 9/2000 | Harner ........................ 356/73 |
| 6,381,009 B1 | * | 4/2002 | McGahan .................... 356/73 |

FOREIGN PATENT DOCUMENTS

| | | |
|---|---|---|
| EP | 0404258 | 12/1990 |
| EP | 0415401 | 3/1991 |
| EP | 0501006 | 9/1992 |
| EP | 0514178 | 11/1992 |
| EP | 0515099 | 11/1992 |
| EP | 0535700 | 4/1993 |
| EP | 0564122 | 10/1993 |
| EP | 0564157 | 10/1993 |
| EP | 0608987 | 8/1994 |
| EP | 0614077 | 9/1994 |
| EP | 0634642 | 1/1995 |
| EP | 0644412 | 3/1995 |
| EP | 0644413 | 3/1995 |
| EP | 0670492 | 9/1995 |
| EP | 0679889 | 11/1995 |
| EP | 0682242 | 11/1995 |
| EP | 0711991 | 5/1996 |
| EP | 0720012 | 7/1996 |
| EP | 0750045 | 12/1996 |
| EP | 0751388 | 1/1997 |
| EP | 0769691 | 4/1997 |
| EP | 0780678 | 6/1997 |
| EP | 0780679 | 6/1997 |
| EP | 0780680 | 6/1997 |
| EP | 0781990 | 7/1997 |
| EP | 0805352 | 11/1997 |
| EP | 0832690 | 4/1998 |
| JP | 3154850 | 7/1991 |
| JP | 5079970 | 3/1993 |
| JP | 5079971 | 3/1993 |
| JP | 6258317 | 9/1994 |
| JP | 7280803 | 10/1995 |
| JP | 8075731 | 3/1996 |
| JP | 8075732 | 3/1996 |
| JP | 8240520 | 9/1996 |
| JP | 9170978 | 6/1997 |
| JP | 9243558 | 9/1997 |
| WO | 9303450 | 2/1993 |
| WO | 9418557 | 8/1994 |
| WO | 9624045 | 8/1996 |
| WO | 9717013 | 5/1997 |
| WO | 9719340 | 5/1997 |

OTHER PUBLICATIONS

Free, A.H. and Free, H.M., Office Practice of Laboratory Medicine, Clinics in Laboratory Medicine, vol. 6, No. 2 (Jun. 1986), "Urinalysis: Its Proper Role in the Physician's Office".

Skoog and West, Principles of Instrumental Analysis, Second Edition, Saunders College/Holt, Rinehart & Winston (Philadelphia 1980) pp. 192–194; 113–351; 352–357.

Y. Yasui, et al., "Urinary Sediment Analyzed by Flow Cytometry", Cytometry 22(1): 75–79 (1995).

M. Roy First, Pathophysiology, Chapter 22, pp. 346–358 "Renal Function".

G. B. Schumann, S.C. Schweitzer, Methods of Analysis, Chapter 56, pp. 820–849, "Examination of Urine".

Sprouse, J.F. and Boruta, M. "Spectral Subtraction and Data Manipulation using Spectra from Digitized Libraries", Proc. SPIE–Int. Soc. Opt. Eng. (1981), 289 (Int. Conf. Fourier Transform Infrared Spectrosc.), 240–244.

Gluch, Richard P. "Computer–Assited Spectral Identification", AM.Lab. (Fairfield, Conn.) (1982), 14(4), 98,100, 102–103.

Ward, K.J., Haaland, D.M., Robinson, R., and Eaton, R.P. "Post Prandial Blood Glucose Determination by Quantitative Mid–Infrared Spectroscopy", Applied Spectroscopy, 46(6), 959,965.

Iwata, et al., "Minimization of Noise in Spectral Data", *Appied Spectroscopy,* vol. 50, No. 6, 1996, pp. 747–752.

* cited by examiner

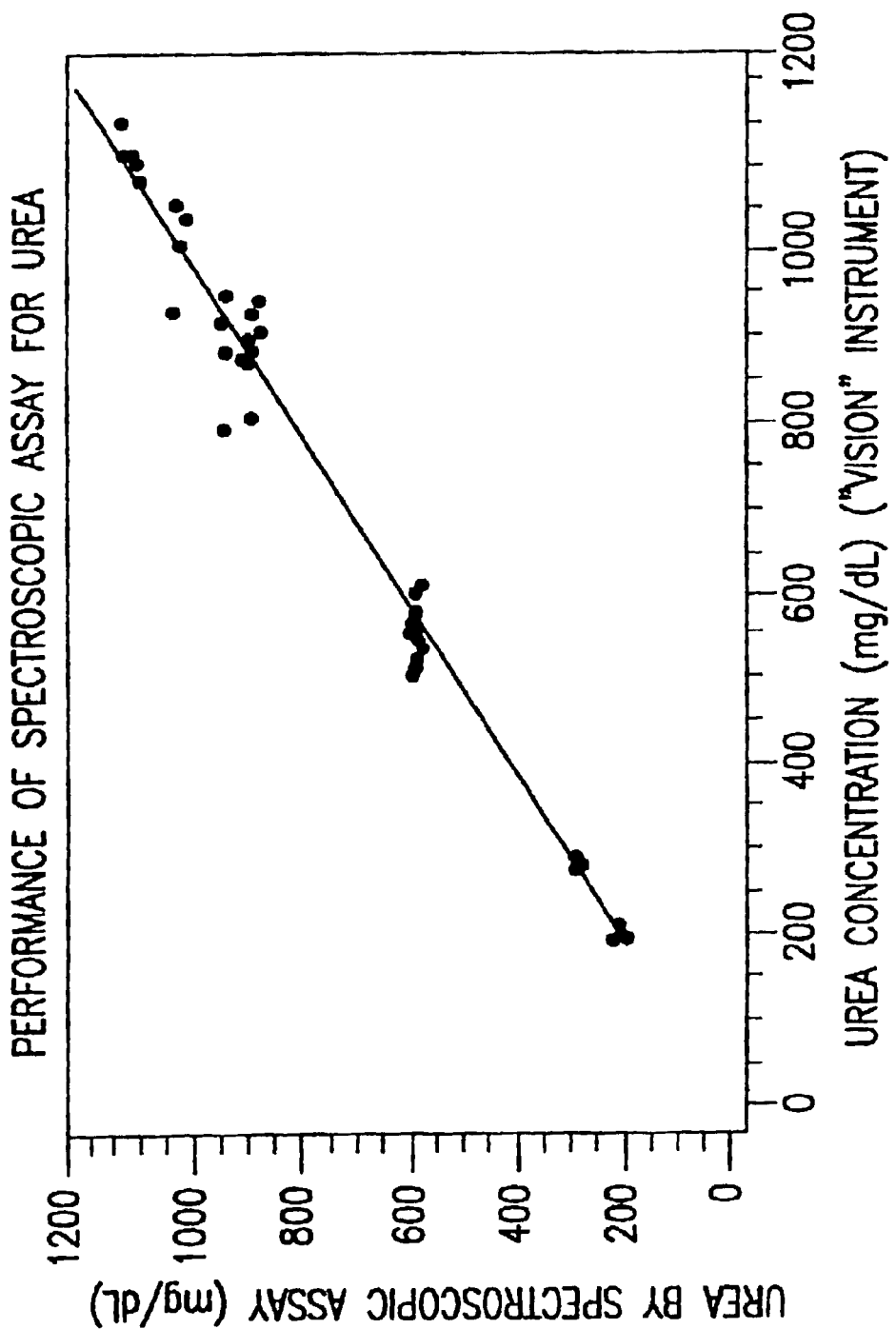

US 6,773,922 B2

REAGENTLESS ANALYSIS OF BIOLOGICAL SAMPLES

This application is a divisional of Ser. No. 09/407,716, filed Sep. 28, 1999, now U.S. Pat. No. 6,426,045, which was a divisional of Ser. No. 09/141,483, filed Aug. 27, 1998, now U.S. Pat. No. 6,087,182.

BACKGROUND OF THE INVENTION

1. Field of the Invention

This invention relates to the field of analysis of biological samples, both solids and liquids, e. g., urinalysis, and, in particular, to apparatus and method for conducting analysis of biological samples without the need for reagents. This invention also relates to detection of adulteration of samples of biological fluid to protect the integrity of analysis results.

2. Discussion of the Art

Determining the concentration of an analyte or a parameter of physical condition in a biological sample has been an important area in the field of diagnostics. Analytes that have diagnostic value includes nutrients, metabolites, enzymes, immunity entities, hormones, and pathogens. The physical characteristics of a biological sample, such as temperature, optical properties, density, and hardness, are also of interest because of their capability of providing indications for diagnostic purposes. Most determination methods use signal-enhancing agents.

Urinalysis involves measuring critical components in a sample of urine to determine the condition of the body with respect to diseases and other substances, e. g., drugs. Urine contains a wide variety of substances. In current urinalysis systems, such as those provided by Bayer and Boehringer Mannheim, the analytes measured include glucose, bilirubin, ketones (80% 3-hydroxybutyrate, 17% acetoacetic acid, 3% acetone), blood (or hemoglobin), protein, urobilinogen, nitrites, and leukocytes. Specific gravity (or refractive index) and pH are also measured. In some cases, measurement of creatinine is suggested, but is not provided by Bayer's or Boehringer Mannheim's urinalysis systems. All of these analytes represent breakdown products of metabolism from various organ systems. The pattern of excretion is indicative of various disease states. The history and utility of urinalysis is discussed in Voswinckel, Peter, "A marvel of colors and ingredients. The story of urine test strips", Kidney International, Vol. 46, Suppl. 47 (1994), pp. S-3–S-7, and Free, Alfred H. & Free, Helen M., "Urinalysis: Its Proper Role in the Physician's Office", Office Practice of Laboratory Medicine, Clinics in Laboratory Medicine—Vol. 6, No. 2, June 1986, both of which are incorporated herein by reference.

Urinalysis testing is also used as a means to determine which samples of urine need to be examined by microscopy, which is such an expensive and time-consuming procedure that it cannot be performed on all urine samples with current methods. Microscopic examination of urine sediment can confirm the presence of bacterial infection, or white cells, indicating infection or kidney damage, among other indications.

The majority of urinalysis testing is accomplished by means of dip and read strip technology supplied by Bayer and Boehringer Mannheim. Strip technology is well understood and suffers from a number of limitations. Readings must be properly timed to obtain accurate results. Controls must be employed. Urine samples must be well mixed and at room temperature. Strips are sensitive to light and humidity, and must be stored and handled properly. Quantitative results are difficult to obtain. Interfering substances can cause incorrect readings.

Abuse of drugs and other substances is recognized as a significant problem in the United States, and is now being recognized in other parts of the world. As a result, more people are being tested in routine drug screening programs than ever before. In the United States, about 10% of the population is estimated to abuse drugs or alcohol, and about 70% of those are employed. Business and government organizations in the United States will spend about $725,000,000 in 1998 to test selected populations to determine whether their performance may be impaired by abuse of depressants, hallucinogens, hypnotics/sedatives, or stimulants. In most cases, the sample tested is urine. Consequences of failing a routine drug screen can be severe, e. g., loss of employment or loss of freedom if testing is performed for the criminal justice system, and these consequences have led to the development of an industry designed to "beat" a drug test. Drug testing can be "beaten" by simply diluting the sample with water, apple juice, or similar materials. Drug testing can also be "beaten" by attacking the macromolecules and indicators used in the testing systems with materials such as acids, bases, nitrites, and glutaraldehyde, among others.

While estimates of the extent of adulteration are difficult to obtain and some evidence suggests that they vary with the populations tested, estimates of adulteration range as high as 30% of urine samples submitted for testing. The drug of abuse assay system using Enzyme Multiplied Immunoassay Technique (EMIT) is a major high-speed screening tool for drugs of abuse, but it is also among the most sensitive systems to failures caused by sample adulteration. Systems based on fluorescence polarization immunoassay (FPIA) are more robust, but are not immune from failures caused by adulterated samples.

To achieve the social purpose of deterring drug abuse by testing of urine, it is essential to assure the integrity of the samples of urine. Sample integrity can be assured by "observed" collection. However, such a stringent method is applicable only in special situations, and is costly. Legal considerations require a thoroughly documented chain of custody for each sample. A system configuration that permits a check for sample adulteration and simultaneously sequesters the sample for further testing such as GC/mass spectrometry, or for archiving, may be advantageous. The integrity of a urine sample can also be judged by measuring specific gravity, pH, creatinine level, and temperature of the sample before committing the sample to further tests that employ costly reagents. Low levels of creatinine may indicate dilution of the sample. An abnormally low or high value of pH indicates the addition of acid or base. Altered specific gravity indicates the addition of foreign materials, such as apple juice or salts, that may alter test results. If the temperature of a urine sample is unexpectedly low, it may indicate that a sample was substituted, and if the temperature of a urine sample is unexpectedly high, it may indicate that a sample was substituted or that a chemical reaction took place. By ensuring sample integrity, potentially adulterated samples may be rejected for testing, and unadulterated samples may be recollected more quickly, thereby assuring the accuracy of the test results, and preventing impaired individuals from endangering the safety of the public.

There are several methods for measuring creatinine. The oldest, the Jaffee method, requires temperature control for accurate results. The 3.5-DiNitroBenzoic Acid (DNBA) method (similar to the Jaffee method) has been adapted to strips for a serum assay. Both methods have been commercialized with as many as four enzymes by Kodak. When measured with long wavelength infrared radiation, creatinine provides the second strongest signal in urine. Hence, infrared spectroscopy utilizing multivariate mathematical analysis is able to "pick-out" creatinine with a high degree of precision and specificity.

The amount of dissolved solids in urine is typically measured by refractive index measurement (the gold standard) or by specific gravity measurements. Measurements of refractive index and specific gravity in urine are highly correlated, as shown by studies of samples of patients in hospitals.

pH is a measure of acid or base content of the urine sample. Standard laboratory practice makes use of a pH electrodes for accurate pH measurements. Miniature pH electrodes have been demonstrated by Nova Biomedical (Waltham, Mass.) in their instruments and by others. Bayer has a block on a colorimetric strip that measures pH in urine with reasonable accuracy for the normal range of pH in urine (4.6–8.0).

It would be desirable to provide a method and a device for analysis of biological samples and detection of sample adulteration that does not encounter the disadvantages of a system based on roagont containing reagent-containing strips. In a reagentless system, the stability, storage, and shelf life issues of reagents would be of no concern. In a reagentless system, the method could be automated and would not require precise timing by the user. Interfering substances could be detected and incorrect readings could be minimized. Proper controls could be incorporated into the system and could be transparent to the user. Quantitative readings could be performed better, and larger dynamic ranges than can be provided by reagent containing reagent-containing strips could be made available. A reagentless system has the additional advantage that it can be adapted to possible future expansion of adulterants when the features of those adulterants become known. If needed, a reagentless system could also be integrated with a reagent-using system to provide a broader menu, better performance, and higher throughput.

SUMMARY OF THE INVENTION

This invention provides an apparatus and method for determining at least one parameter, e. g., concentration, of at least one analyte, e. g., urea, of a biological sample, e. g., urine. A biological sample particularly suitable for the apparatus and method of this invention is urine. In general, spectroscopic measurements can be used to quantify the concentrations of one or more analytes in a biological sample. In order to obtain concentration values of certain analytes, such as hemoglobin and bilirubin, visible light spectroscopy can be used. In order to obtain concentration values of other analytes, such as urea, creatinine, glucose, ketones, and protein, infrared light spectroscopy can be used. The apparatus and method of this invention utilize one or more mathematical techniques to improve the accuracy of measurement of parameters of analytes in a biological sample.

In one aspect, the invention provides a method for determining at least one parameter of at least one analyte of a biological sample involving the use of a mathematical technique to assist in reducing noise in signal detection in spectroscopic measurements. More specifically, this invention provides a method for reducing noise in a determination of concentration of at least one analyte of interest in a biological sample by means of spectroscopic analysis comprising the steps of:

(a) identifying a mathematical function that is substantially similar to a region of a non-smoothed spectrum of the sample over a selected range of the non-smoothed spectrum;

(b) selecting a portion of the region of the non-smoothed spectrum such that noise in the selected portion is substantially random;

(c) determining coefficients of the mathematical function that result in a close fit of the function to the selected portion of the non-smoothed spectrum;

(d) calculating at least one value of the non-smoothed spectrum at at least one wavelength of the non-smoothed spectrum by means of the coefficients and the mathematical function of step (c), wherein said at least one wavelength includes the center of the region of the non-smoothed spectrum;

(e) assigning said at least one calculated value of the non-smoothed spectrum to a wavelength including the center of the selected portion of the region of the non-smoothed spectrum to form at least one point of a smoothed spectrum;

(f) shifting a selected distance in the non-smoothed spectrum and repeating steps (c), (d), and (e) until a desired amount of the smoothed spectrum is formed;

(g) forming a residual spectrum by subtracting each point of the desired amount of the smoothed spectrum at a given wavelength from each point of the non-smoothed spectrum at said given wavelength;

(h) inspecting the residual spectrum to determine if it is random; and (i) if the residual spectrum is not random, repeating steps (b), (c), (d), (e), (f), (g), and (h) to achieve a smoothing, wherein said residual spectrum is random.

In another aspect, the invention provides a method for determining at least one parameter of at least one analyte of a biological sample involving the use of a mathematical technique to assist in elimination of residual signal associated with interfering compounds by the use of multivariate analysis, such as partial least squares. More specifically, this invention provides a method for determining concentration of at least one analyte of interest in a biological sample of an individual by means of spectroscopic analysis comprising the steps of:

(a) identifying at least one analyte that is a major component of said biological sample, said at least one analyte accounting for significant variations with respect to a plurality of spectra of biological samples from a plurality of donors of said biological samples;

(b) measuring a spectrum for each of the plurality of biological samples from the plurality of donors of the biological samples;

(c) calculating a model spectrum for each of the plurality of biological samples from the plurality of donors of the biological samples by mathematically fitting spectra of the analytes of the at least one identified analyte to each spectrum of each of the biological samples from the plurality of donors of the biological samples;

(d) calculating a residual spectrum for each spectrum of each of the biological samples from the plurality of donors of the biological samples by subtracting each value of the model spectrum from each value of the spectrum of the biological samples from the plurality of donors of the biological samples that corresponds to the model spectrum;

(e) repeating steps (a), (b), (c), and (d) at least one time by introducing at least one additional analyte to the model spectrum until the calculated residual spectra are substantially constant from one biological sample to another biological sample of the plurality of biological samples from the plurality of donors of the biological samples;

(f) determining a set of calibration parameters from the model spectra, said set of calibration parameters accounting for effects of said substantially constant residual spectra; and (g) using said calibration parameters to determine concentration of an analyte of interest in the sample of biological fluid of the individual.

By use of one or more of these mathematical techniques, a calibration model can be derived. The calibration model and constants associated with the calibration model can be used to calculate the concentration of an analyte of interest in a biological sample.

In another aspect, the invention provides a method for measuring the refractive index of a sample of biological fluid while making spectroscopic measurements substantially simultaneously. The refractive index measurement provides the equivalent to a measurement of specific gravity, because both measurements are affected by the amount of solute in a solution. In this invention, however, the beam of light for measuring the refractive index is not co-linear with the beam of light for spectroscopic measurements. Further, pH electrodes can be used to obtain accurate pH values of a sample of biological fluid. An ion selective electrode can be used to provide nitrite values of a sample of biological fluid when nitrites are present at low concentration, while infrared spectroscopy can be used to provide nitrite values of a sample of biological fluid when nitrites are present at higher concentration.

If the spectroscopic measurements previously mentioned are combined with a cell counting method, such as flow cytometry, a fully integrated, rapid system for determining at least one parameter of at least one analyte of interest in a biological fluid as well as at least one parameter of at least one particulate material in a sample of biological fluid can be constructed. Such a system can provide enhanced automation of systems that are now only partially automated.

In order to make it possible to carry out the foregoing methods in an optimal manner, systems utilizing several novel components have been developed. To aid in enhancing measurements of refractive index, it has been found that a position-sensitive detector is preferred. Such a detector is commercially available. An arrangement for aligning the light source with the sample and the position-sensitive detector has been designed. To aid in enhancing the speed and convenience of carrying out spectroscopic measurements and refractive index measurements, a sample cell assembly having a unique geometry has been designed. In addition, in some cases, it is desirable to employ assays that employ reagents to enhance the accuracy of the reagentless system described herein. For this purpose a system that integrates the reagentless system of this invention with a reagent-using device has been developed. The integration of a reagent-using system with the reagentless system of this invention makes it possible to carry out determinations on analytes of interest that exhibit little or no spectral signature.

In a preferred embodiment of this invention, the system described herein can be used to measure creatinine, pH, and refractive index to check for adulteration of urine in a drugs-of-abuse testing environment. For spectroscopic measurements, it is preferred to employ a spectrometer which measures the spectra of analytes of interest in a sample of biological fluid. In another preferred embodiment of this invention, the spectrometer previously mentioned can be replaced by a filter photometer unit, which involves utilization of appropriate filters to provide absorbance values at selected wavelength regions of a spectrum of interest. Regardless of which type of instrument is used to determine the spectrum, the preferred embodiments of this invention include the following components:

(1) spectrometer or infrared filter photometer unit to measure the concentration of creatinine in a sample of urine, whereby sample dilution brought about by ingestion of water or by direct dilution with other materials can be assessed;

(2) pH electrodes to assess the suitability of the sample for chemistry assays;

(3) refractometer to measure the level of dissolved solids.

Such a system may be expanded to include measurement of other adulterants, such as glutaraldehyde and nitrites. Measurement of adulterants can be simplified by selection of appropriate filters in an infrared filter photometer.

An embodiment involving a hand-held or easily portable system that can serve the workplace testing area or insurance physicals area by allowing an immediate assessment of the integrity of a urine sample collected in a remote location is also contemplated. The system may include the following components:

(1) laser diode or light emitting diode to measure the concentration of creatinine and other adulterants in a sample of urine, whereby the creatinine value obtained can be used to assess dilution of sample caused by ingestion of water or by direct dilution with water, while positive detection of other adulterants, such as glutaraldehyde or nitrites, can be used to identify urine samples spiked with such adulterants, (2) pH electrodes to assess the suitability of the sample for chemistry assays, (3) refractometer to measure the level of dissolved solids, (4) temperature sensor to determine if the sample is at a physiologically significant temperature or whether a false sample has been substituted.

Concentrations of components in a sample of urine are variable depending on the state of hydration of the individual. By calculating the ratio of the concentration an analyte of interest in a urine sample (e.g., ketones) to the concentration of creatinine, measurement variability can be reduced or eliminated.

This invention provides several advantages over urinalysis systems currently in use. One of the problems for bilirubin determinations by means of test strips is caused by the stain of the reaction pad by urine, the color of which is too close to the color generated by the chemical reaction for bilirubin determination. This false positive situation is of such concern that some laboratories routinely run confirmatory tests. Because spectroscopic methods involve multiple wavelength differentiation, and do not generate a colored compound by chemical reaction, they do not suffer from the interference caused by the native color of urine.

If integrated into an automatic analyzer system or if interfaced with the ADx systems (an automated drug of abuse assay instrument by Abbott Laboratories), the reagentless system of this invention can provide a drug/creatinine ratio. The ratio can be used as a means to correct for sample dilution, and may represent a new standard in drugs of abuse testing.

The reagentless system of this invention provides improved performance, rapid throughput, elimination of reagents, and increased convenience for the user. The reagentless system of this invention allows substantial removal of base-line drift in spectroscopic measurements. The reagentless system of this invention allows determination of the concentrations of several analytes simultaneously in the presence of interfering signals in spectroscopic measurements.

BRIEF DESCRIPTION OF THE DRAWINGS

FIG. 29 is a graph showing the performance of a spectroscopic assay for urea.

DETAILED DESCRIPTION

Figure 1:
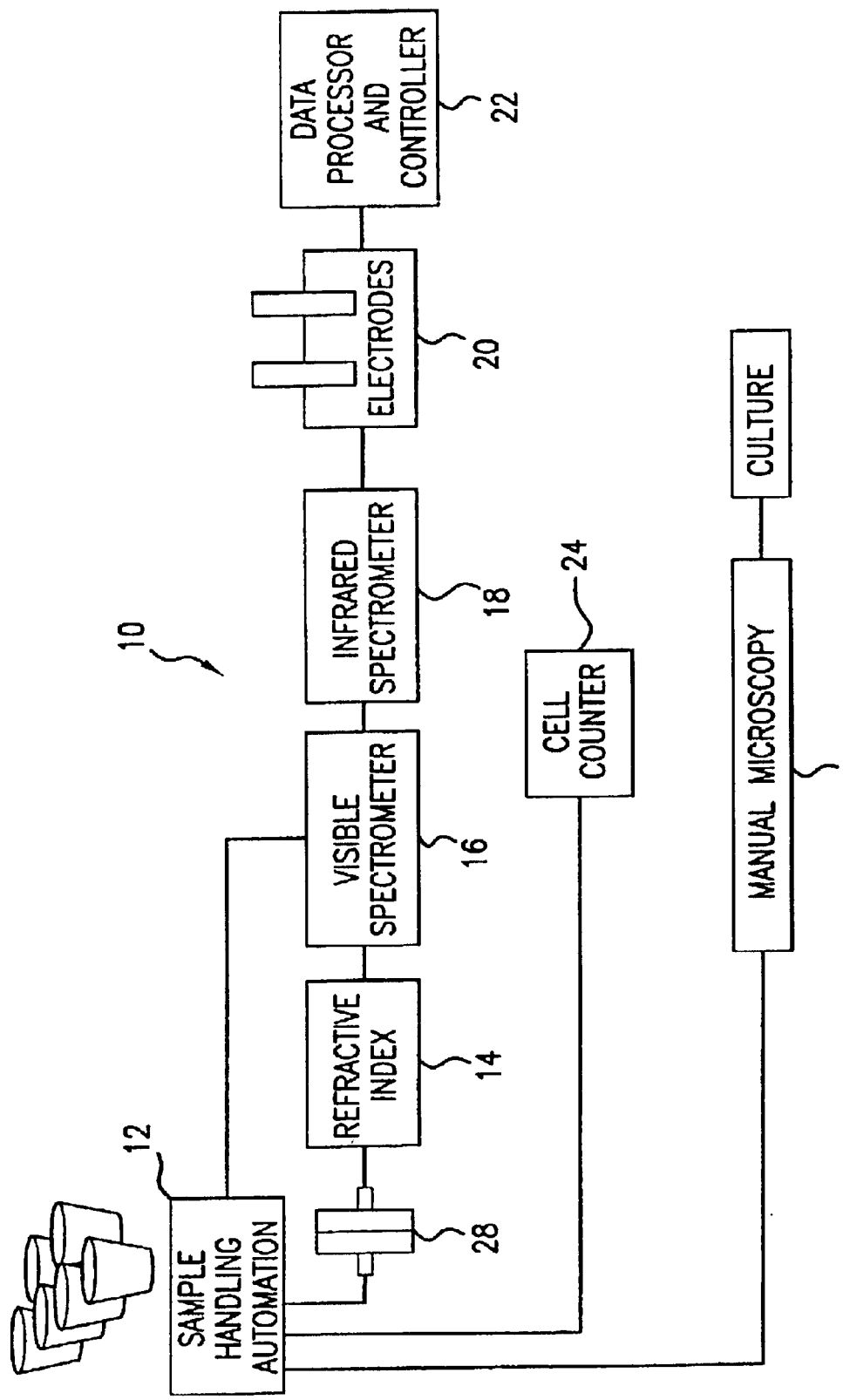
FIG. 1 is a schematic drawing of an analytical system capable of providing full menu capability and versatility for the practice of this invention.
Figure 2:
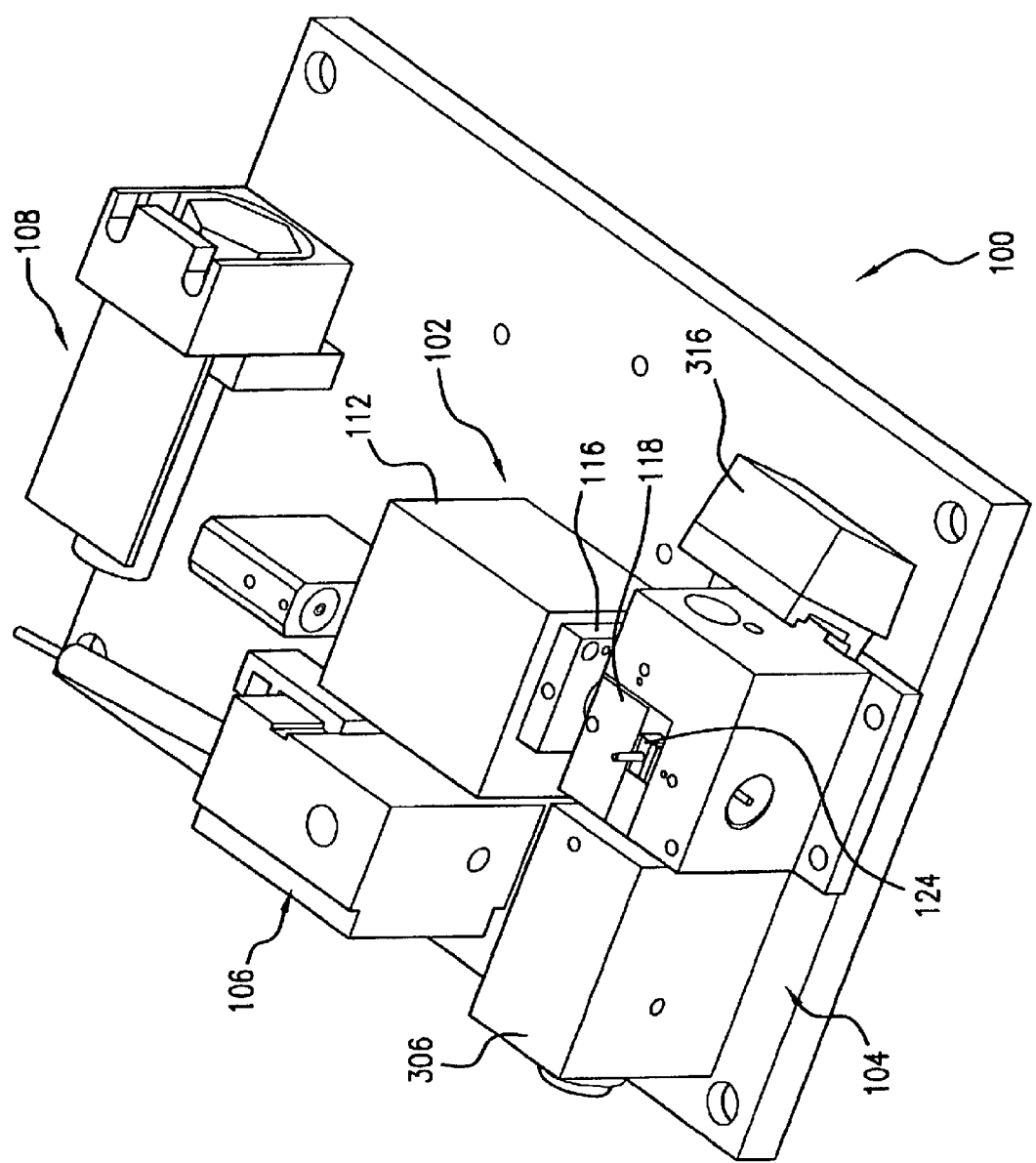
FIG. 2 is a perspective view of an embodiment of an apparatus suitable for use in this invention. In this embodiment, the unit for measuring the spectrum is a spectrometer.

As used herein, the expression "spectroscopic analysis" means analysis of a spectrum in order to determine characteristics of its source. The term "absorption" means the reduction of intensity of electromagnetic radiation, according to Beer's Law, of a beam of electromagnetic radiation as it propagates through a material. The expression "biological sample" is intended to include biological samples in solid form and biological samples in fluid form. For example, biological samples in solid form include, but are not limited to, living body parts, such as, for example, fingers, ear lobes, forearms, internal organs and the like, biopsy, tissue, skin, stool, and so forth. Biological sample in fluid form include, but are not limited to, urine, whole blood, plasma, serum, sputum, saliva, sweat, interstitial fluid, cerebral spinal fluid, and dialysate obtained in kidney dialysis, and the like.

As used herein, the term "calibration" means the determination of a mathematical function relating a physical quantity being measured to a signal measured. The term "prediction" refers to the calculation of the concentration of an analyte in a given sample based on the signals measured from the sample and the calibration determined from samples independent of the given sample.

As used herein, the expression "major component" refers to an analyte of a biological sample that provides a signal that is substantially larger than the background signal (i. e., the background signal excluding the contribution of water). For example, in urinalysis, urea is a major component on account of its large spectral signature and high concentration in urine. The expression "minor component" refers to an analyte of a biological sample that provides a signal that is comparable in magnitude or smaller in magnitude than the background signal (i. e., the background signal excluding the contribution of water). For example, in urinalysis, nitrites are considered a minor component, on account of its low concentration in normal urine.

As used herein, the term "residual" means the remaining portion of a measured quantity after a major portion of the measured quantity has been accounted for. With respect to a spectral signal obtained from a sample containing a multiplicity of components, the residual spectrum is the portion of the spectral signal remaining after the portion of the spectral signal contributed by major components of the sample is subtracted from the observed spectrum. This residual spectrum of the observed spectrum typically results from the presence of a combination of minor components, which are usually interfering compounds. For example, in the case of urinalysis, it has been discovered herein that the residual portion of the spectral signal could be due to combination of nitrites, salts, vitamins, metabolites, and hormonal metabolites that are present at low concentrations.

The term "model" means a tentative description of a theory or system that accounts for substantially all of its known properties. The term "constant" means an experimental or theoretical condition, factor, or quantity that occurs, is held, or is regarded as invariant in given circumstances. The term "noise" means a usually random and persistent disturbance that obscures or reduces the clarity or quality of a signal. The term "random" refers to a phenomenon happening by chance, as in a haphazard manner. For example, a random noise is a variation in a signal that occurs by chance. Because the chance of the variation to be either higher or lower than the true value is equal, the sum of the random noise (i. e., the difference of the observed value from the true value) over an extended observation dimension (time, space, or wavelength) approached zero. The terms "smooth", "smoothing", and the like refer to elimination of random noise from a measured spectrum.

The term "reagentless" refers to a determination of a parameter of an analyte of a biological sample without the use of a reagent. The term "reagent-using" means a method (in contrast to reagentless) where chemical or biological agents are used for enhancing the process of determining the presence or concentration of a specific analyte. For example, when an enzyme is used to react with a specific analyte to generate a detectable signal for determination of that analyte, the enzyme is the reagent used for determination of that analyte, and the detection method is a "reagent-using" method.

The expression "derivative spectroscopy" means either the process of determining a derivative of a spectrum or the process of measuring a derivative spectrum directly by means of a derivative spectrometer. Derivative spectroscopy refers to the rate of change of the spectrum with respect to the rate of change of wavelength. There can be many different orders in derivative spectroscopy corresponding to the different orders of derivatives in a mathematical function. For example, in first order derivative spectroscopy, the first derivative of the observed spectrum is determined. The first derivative is equivalent to calculating slope, as in obtaining the first derivative of a mathematical function. See also Skoog and West, *Principles of Instrumental Analysis*, Second Edition, Saunders College/Holt, Rinehart and Winston (Philadelphia:1980), pp.192–194, incorporated herein by reference.

The expression "base-line drift" means a slow varying trend of the measured background in the detection system. The rate of change of base-line drift is lower than the rate of change of random noise. Base-line drift is typically caused by lamp warm up, temperature change in the system, or lamp aging.

As used herein, the term "light" means the subset of electromagnetic radiation that includes the ultraviolet region of the electromagnetic spectrum, the visible region of the electromagnetic spectrum, and the infrared region of the electromagnetic spectrum. For example, radio waves are not light waves.

As used herein, the ultraviolet region of the electromagnetic spectrum includes light having a wavelength of from about 190 nm to about 400 nm. The visible region of the electromagnetic spectrum includes light having a wavelength of from about 400 nm to about 780 nm. The infrared region of the electromagnetic spectrum comprises the near-infrared region of the electromagnetic spectrum, the mid-infrared region of the electromagnetic spectrum, and the far-infrared region of the electromagnetic spectrum. The near-infrared region of the electromagnetic spectrum includes light having a wavelength of from about 780 nm to about 1,500 nm; the mid-infrared region of the electromagnetic spectrum includes light having a wavelength of from about 1,500 nm to about 3,000 nm; the far-infrared region of the electromagnetic spectwm includes light having a wavelength of from about 3,000 nm to about 40,000 nm.

In one aspect, this invention involves a method for determining at least one parameter, e. g., concentration, of an analyte of interest, e. g., urea, in a sample of biological fluid, such as, for example, urine. One or more of the following techniques can be used to enhance the determination of the aforementioned parameter(s):

(1) using mathematical smoothing of spectra, e. g., polynomial smoothing, to reduce noise in spectral measurements so that accurate calibration and prediction are possible;

(2) computing a derivative of spectra before applying multivariate regression techniques to remove base-line drift in spectral measurements and to bring the weaker spectral features that carry analytical information into prominence;

(3) determining the major components of the biological system so that the residual fitting errors can be identified and removed by means of a calibration operation.

The following features can be used to enhance the determination of one or more parameters of an analyte of interest in a sample of biological fluid, e g., urine:

(1) refractive index measurements and pH measurements can be combined with spectroscopic measurements, whereby detection of adulteration of samples intended for test of drugs of abuse or urinalysis can be carried out;

(2) refractive index measurements, pH measurements, and use of reagents for analytes present in low concentration can be combined with spectroscopic measurements, whereby detection of adulteration of samples intended for test of drugs of abuse or urinalysis can be carried out;

(3) impedance spectroscopy can be used to quantify analytes in a sample of urine that have a unique impedance frequency signature.

Techniques for spectroscopic measurements and refractive index measurements are well known to those of ordinary skill in the art. By gathering and processing the data obtained in these measurements in novel ways, the accuracy of results can be improved. Techniques for spectroscopic measurements are described in Skoog and West, *Principles of Instrumental Analysis,* Second Edition, Saunders College/Holt, Rinehart and Winston (Philadelphia:1980), pp. 113–351, incorporated herein by reference. See also, B. Henderson, *Handbook of Optics,* 2nd edition, McGraw-Hill (New York:1995), chapter 20, incorporated herein by reference. Techniques for refractive index measurements are described in Skoog and West, *Principles of Instrumental Analysis,* Second Edition, Saunders College/Halt, Rinehart and Winston (Philadelphia:1980), pp. 352–357, incorporated herein by reference. See also, E. Hecht, *Optics,* 2nd edition, Addison-Wesley (Reading, MA: 1988), pp. 163–169, incorporated herein by reference.

Figure 25:
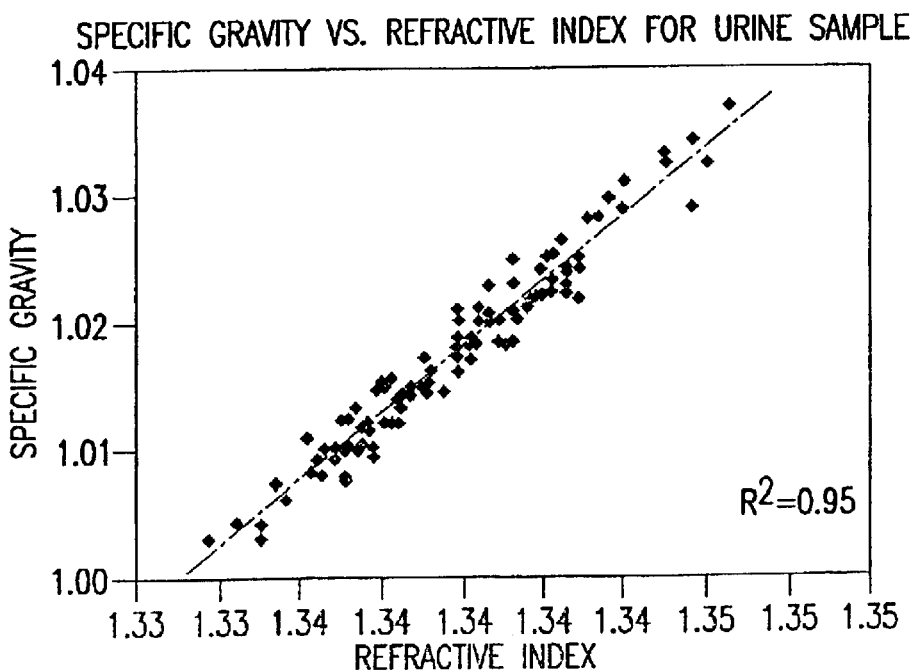
FIG. 25 is a graph showing the relationship between specific gravity and refractive index for normal urine samples. This graph was derived from S. Bakhshandeh et al., "Michigan Medicine", 74(21): 399–403, 1975), incorporated herein by reference.
Figure 26:
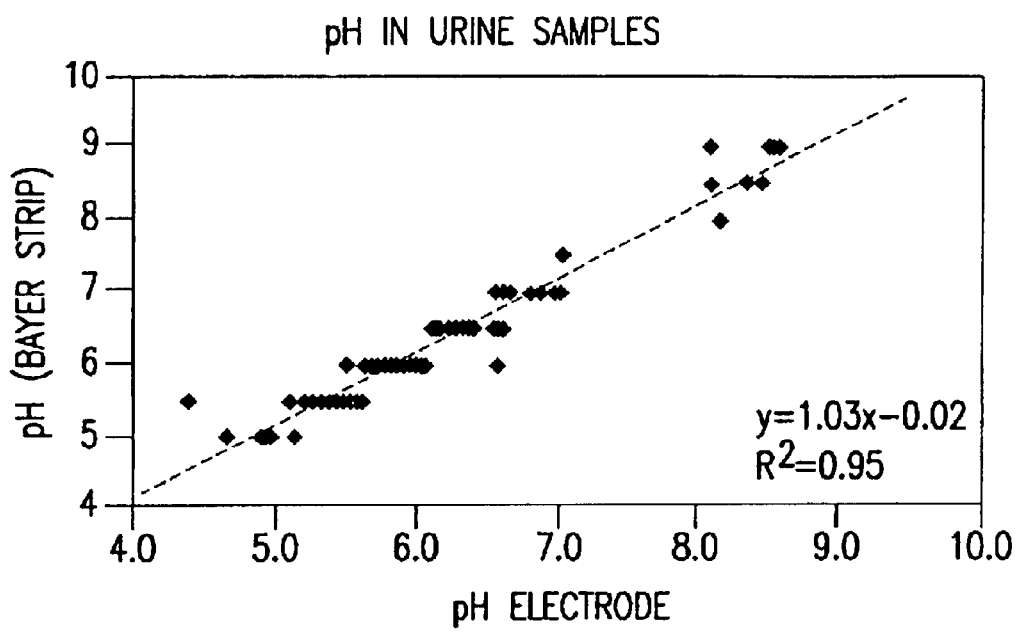
FIG. 26 is a graph showing the relationship between a pH determination by Bayer strips and a pH determination by pH electrodes.

FIG. 1 illustrates a system showing various types of measurements that can be carried out with the method and apparatus of the present invention. The reagentless system 10 comprises a sample handling subsystem 12, the purpose of which is to introduce samples of biological fluid, e.g., urine, to the optical measurement subsystems. The reagentless system 10 further comprises a refractive index determination subsystem 14, a visible light spectroscopic subsystem 16, and an infrared light spectroscopic subsystem 18. In the case of urinalysis, the refractive index determination subsystem 14 can be used to determine the specific gravity of urine, the visible light spectroscopic subsystem 16 can be used to determine color, turbidity, bilirubin, hemoglobin, urobilinogen, and protein, or other analytes with a usable visible spectral signature, and the infrared light spectroscopic subsystem 18 can be used to determine urea, creatinine, glucose, protein, and ketones, or other analytes that have a usable near-infrared or mid-infrared spectral signature. The reagentless system 10 may further comprise a subsystem 20 for determining pH and nitrites. The data obtained via the subsystems 14, 16, 18, and 20 can be processed by means of data processing and controlling subsystem 22. The reagentless system 10 can be combined with a cell counter 24, the purpose of which is to determine leukocytes, bacteria, red blood cells, casts, crystals, and the like. The reagentless system 10 can further be combined with a manual subsystem 26, the purpose of which is to identify bacteria or further culture bacteria for drug resistance testing at a later time. FIG. 25 shows how specific gravity can be determined from a determination of refractive index. FIG. 26 shows how pH determined by means of pH electrodes correlates with pH determined by means of Bayer strips.

The sample handling subsystem 12 can comprise (1) a pump or equivalent means (a) (not shown) for aspirating a liquid sample into a sample cell assembly (not shown) for containing the sample during optical measurements and to the pH determination subsystem 20 and (b) for removing the liquid sample from the sample cell assembly and the pH determination subsystem 20 and delivering the removed sample to a waste container (not shown), (2) an aspiration probe or other implement (not shown) for aspirating the sample, and (3) a flow control system (not shown), e. g., a three-way valve, so that the sample or a wash liquid may be aspirated and dispensed through the sample handling subsystem 12. The liquid sample can be drawn into the sample cell assembly by means of a pump or syringe mechanism (not shown). Alternatively, the liquid sample can be drawn into the sample cell assembly by means of a vacuum (not shown), such as a commercially available blood draw "VACUTAINER" tube. A filtering system 28 is preferably included to remove significant particulate materials.

The refractive index determination subsystem 14 can comprise a source of light (not shown) that generates a light beam, which is propagated through a sample cell assembly (not shown). The refractive index determination subsystem 14 can further comprise a detector (not shown) for detecting the deflection of the light beam that emerges from the sample cell assembly. The purpose of refractive index measurement is to determine the percent solids in the liquid sample. The normal range of the refractive index can be defined by the technician, for example between 1.336 and 1.345. The refractive index determination subsystem 14 can be used to measure the percent solids dissolved in the liquid sample, as an indicator of degree of hydration of biological samples, particularly biological fluids, such as, for example, urine.

The visible light spectroscopic subsystem 16 can comprise a source of visible light (not shown). The source of visible light can be a broadband source, such as a tungsten filament lamp, if used in conjunction with a wavelength selection module (not shown). Alternatively, the source of visible light can be monochromatic or quasi-monochromatic, such as a laser diode or a light emitting diode. Multiple monochromatic light sources would be spatially or angularly multiplexed by use of beam splitters, mirrors, and the like, such that the beams travel through substantially the same path through the sample cell assembly. The wavelength selection module can comprise a set of filters, a grating monochromator, a prism monochromator, an acousto-optic tunable filter, or any other wavelength dispersing device. The visible light spectroscopic subsystem 16 can comprise a detector (not shown) to determine the degree to which the light is affected by the sample. The visible light spectroscopic subsystem 16 can be used to determine color, turbidity, bilirubin, urobilinogen and hemoglobin, or other analytes with a usable visible spectral signature.

The infrared light spectroscopic subsystem 18 can comprise a source of infrared light (not shown). The source of infrared light can be a broadband source, such as a tungsten filament lamp, if used in conjunction with a wavelength selection module (not shown). Alternatively, the source of infrared light can be monochromatic or quasi-monochromatic, such as a laser diode or a light emitting diode. Multiple monochromatic light sources would be spatially or angularly multiplexed by use of beam splitters, mirrors, and the like, such that the beams travel through substantially the same path through the sample cell assembly. The wavelength selection module can comprise a set of filters, a grating monochromator, a prism monochromator, an acousto-optic tunable filter, or any other wavelength dispersing device. The infrared light spectroscopic subsystem 18 can comprise a detector (not shown) to determine the degree to which the light is affected by the sample. The infrared light spectroscopic subsystem 18 can be used to determine urea, creatinine, glucose, protein, ketones, nitrites, or other analytes, with a usable near-infrared or mid-infrared spectral signature. The purpose of a creatinine measurement, with respect to a sample of urine, is to determine whether or not the creatinine level of the urine sample is within the normal range. The range that is considered to be normal can be defined by the technician, for example, above 20 mg/dL. If the creatinine level of the urine sample is below 20 mg/dL the urine sample may be too dilute for accurate identification of drugs present in the urine. Dilution of a urine sample may have been caused by excessive intake of water.

The pH determination subsystem 20 can comprise a standard pair of electrodes that measures a potential drop between a measurement electrode and a reference electrode. The purpose of a pH measurement is to determine whether or not the pH level of a biological sample is within normal range. Normal range can be determined by the technician and can range, for example, between 3 and 11. pH values outside of this range may indicate that materials have been added to the biological sample for the purpose of producing a false negative in a drugs of abuse determination. Alternatively, pH outside this range may indicate that materials may have been added to the biological sample to alter or destroy enzymes.

Nitrites ($NO_2$)can be measured by means of spectroscopy, by means of ion selective electrodes, or by adding a reagent and making a colorimetric measurement. The purpose of a $NO_2$ measurement, with respect to a sample of urine, is to determine if $NO_2$ has been added to the sample of urine for the purpose of producing a false negative test result for a drug of abuse in a drug of abuse adulteration test. Determination of $NO_2$ can also be used as an indicator for an infection in a urinalysis test.

A colorimetric measurement subsystem that utilizes one or more reagents may be included as needed to measure the concentration of an analyte of interest in a biological sample, either when the concentration of the analyte is too low to allow measurement by spectroscopy, or when the spectral signature of the analyte is insufficient to allow accurate measurement of the concentration. An impedance spectrometric measurement device may be included to measure the impedance of the biological sample at one or more frequencies for the purpose of measuring the concentration of an analyte of interest that cannot be measured by absorption spectroscopic analysis but that has a unique impedance spectral signature.

The data processing and controlling subsystem 22 contains a detector (not shown) to measure how the light is affected by the sample in the sample cell assembly, an amplifier (not shown) to amplify the signal from the detector, and an A/D (analog to digital) converter (not shown) to convert the amplified signal to a number, and a signal processor (not shown) to process the data. A reference detector (not shown) determines a signal proportional to the power of the source incident on the sample cell assembly. This signal may be used to compensate for source fluctuations in software, or to actively adjust the power to the source to stabilize its output. The aforementioned reference detector may be eliminated if the source of light is sufficiently stable to obtain accurate results.

Additional features that can be combined with the foregoing subsystems include a cell-counting subsystem. When positive values are obtained for leukocytes or nitrites or blood in a sample of urine, a more detailed microscopic evaluation of urine sediment is called for. To obtain a urine sediment determination, a sample of urine is centrifuged to form pellets of sediment materials in urine. The sediment materials include leukocytes, red blood cells, cell ghosts, bacteria, crystals, and casts. The sediment pellet is transferred to a slide and a skilled technician must quantify the material by inspection. Such a process is time-consuming and costly.

Recent literature (Y. Yasui et al., "Urinary Sediment Analyzed by Flow Cytometry", Cytometry 22(1):75–79, 1995) suggests that the formed elements may be quantified by cell counting methods, which employ light scattering and/or urine impedance measurements. A system that combines cell counting technology with one or more of spectroscopic measurements, refractive index measurements, pH measurements, and ion selective electrodes could bring about complete automation of urinalysis, thereby saving time for a trained technician and saving cost for the testing institution.

Another feature that can be combined with the foregoing subsystems is a manual subsystem, which typically includes microscopy. Microscopy of urine sediment allows a trained, experienced technician to identify a number of disease indicators in urine, such as, for example, red cells, white cells, bacteria, casts, and crystals. Microscopy, as it is currently practiced in many laboratories, is a manual, time-consuming process involving a number of steps. To begin the process, urine must be centrifuged for five minutes at about 80 xg, causing formed elements to pellet at the bottom of the centrifuge tube. Most of the supernatant urine is carefully decanted, leaving only a small amount of urine to re-suspend the pellet. After re-suspension, the re-suspended pellet is spread on a microscope slide, and examined first under low and later under high power magnification to search for red cells, leukocytes, bacteria, casts, and crystals. Subdued lighting helps identify hyaline casts and crystals that are nearly transparent in bright field microscopy. With increased lighting, fat bodies change from dark to light and become highly refractile in bright field microscopy. With polarized light, fat bodies become especially visible as they typically contain significant quantities of cholesterol, a refractile material. The structure of urine casts may indicate their origin, and a trained eye is needed to accurately identify structures. In a separate separate step, addition of biological stains to the urine sediment enhances the technologist's ability to identify red cells, leukocytes and bacteria in urine. See *Clinical Chemisty: Theory, Analysis and Correlation*, second edition, Kaplan, L. A. and Pesce, A. J. (Editors), (C. V. Mosby Company:1989), pages 832–848, incorporated herein by reference.

In a preferred embodiment, as shown in FIGS. 2, 3, 4, 5, and 6, the apparatus 100 comprises a spectral measurement assembly 102, a refractive index determination assembly 104, a pH electrode assembly 106, and a fluid pump assembly 108.

The purpose of the spectral measurement assembly is to utilize spectral measurements to determine the concentration of at least one analyte of interest in a biological sample, more particularly a biological fluid.

Figure 3:
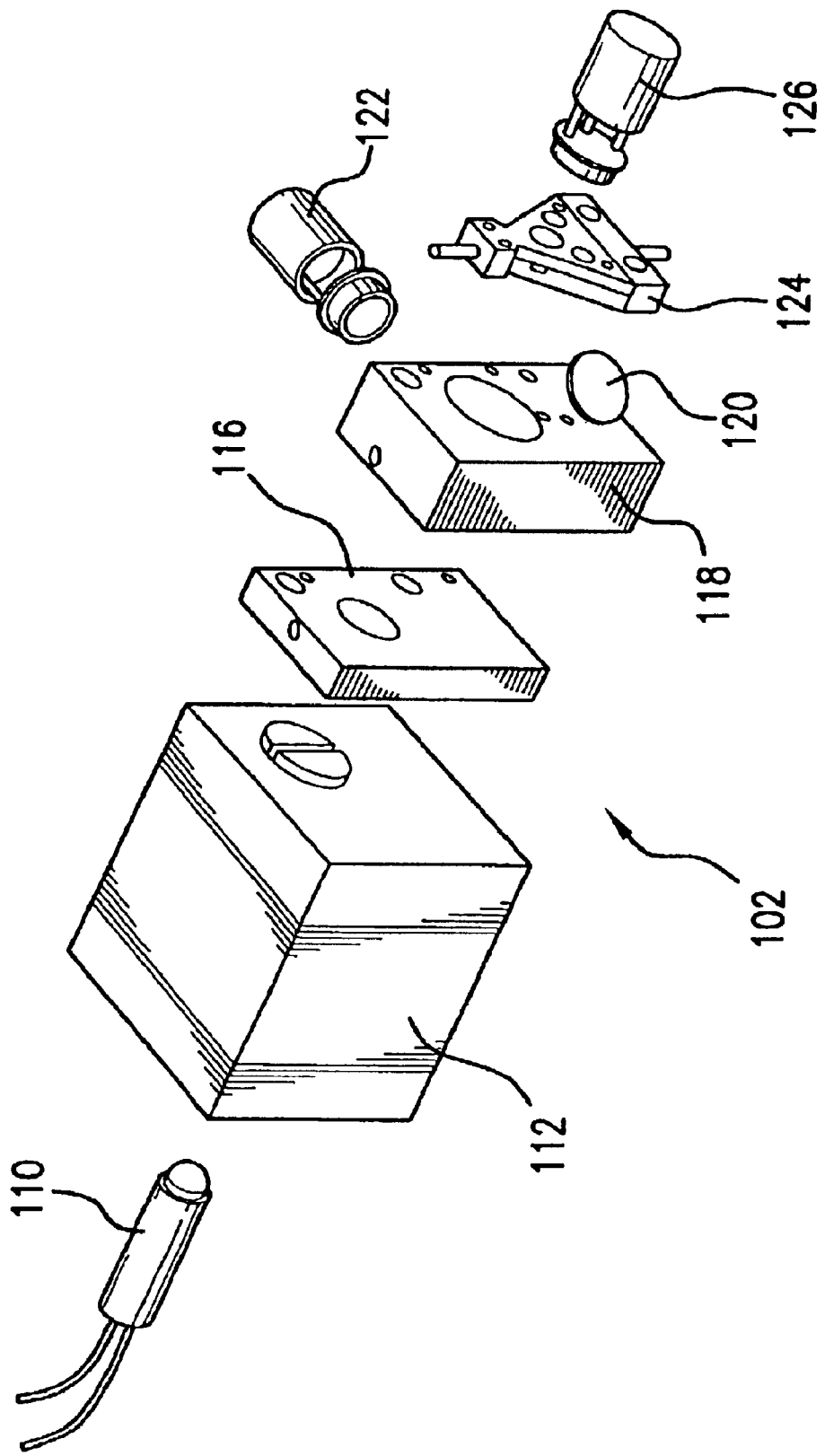
FIG. 3 is an exploded perspective view of the essential components of the unit employed in FIG. 2 for measuring the spectrum.

The spectral measurement assembly 102, shown in detail in FIG. 3, comprises a source of light 110, a scanning monochromator 112, a collimating lens (not shown), a holder 116 for the collimating lens, a lens holder/beam splitter assembly 118, a focusing lens (not shown), a beam splitter 120, a reference detector 122, a sample cell assembly 124, and an absorption detector 126. The functions of the foregoing components are well known to those of ordinary skill in the art. However, the functions will be briefly described in the context of the present invention. The source of light 110 provides the light for the spectral measurement.

The monochromator 112 selects the wavelength for an absorption measurement. The collimating lens collimates the beam of light emerging from the scanning monochromator 112. The holder 116 supports the collimating lens. The lens holder/beam splitter assembly 118 holds the focusing lens and the beam splitter 120. The beam splitter 120 diverts a portion of the light entering the assembly 118 to the reference detector 122, which indicates the intensity of the source of light 110. This is particularly important in order to compensate for the drift of the source of light. Light source fluctuation could result from power variation, temperature variation, and age of the source of light. The sample cell assembly 124 has a chamber that contains the biological sample undergoing the spectroscopic measurements. The focusing lens focuses the collimated light onto the biological sample in the sample cell assembly 124. The absorption detector 126 measures the quantity of light absorbed by the biological sample. Not shown are the electronic components for processing data and controlling the functional components of the apparatus.

When a scanning monochromator is used in the arrangement shown in FIG. 3, the wavelength of the light is selected before the beam of light is propagated through the sample. In some circumstances it is preferred to use an array spectrometer in place of the scanning monochromator. When array spectrometer is used, the beam of light from the source of light enters the sample. The beam of light exiting the sample is then focused onto the entrance aperture of the array spectrometer. The light within the beam is then dispersed onto a detector array, such that the detector array measures the intensity of the beam as a function of wavelength. The advantage of a detector array is that it provides the capability of measuring the spectra very quickly, typically less than one second. Array spectrometers are described in detail in B. Henderson, *Handbook of Optics*, 2nd edition, McGraw-Hill (New York: 1995), chapter 20, incorporated herein by reference. A commercially available scanning monochromator is a TR 190MS2 monochromator from Instruments SA. A commercially available array spectrometer is a NIROSC array spectrometer from Control Development. It should be noted that a monochromator differs from a spectrometer in that a spectrometer includes a detector and a monochromator does not include a detector.

Figure 4:
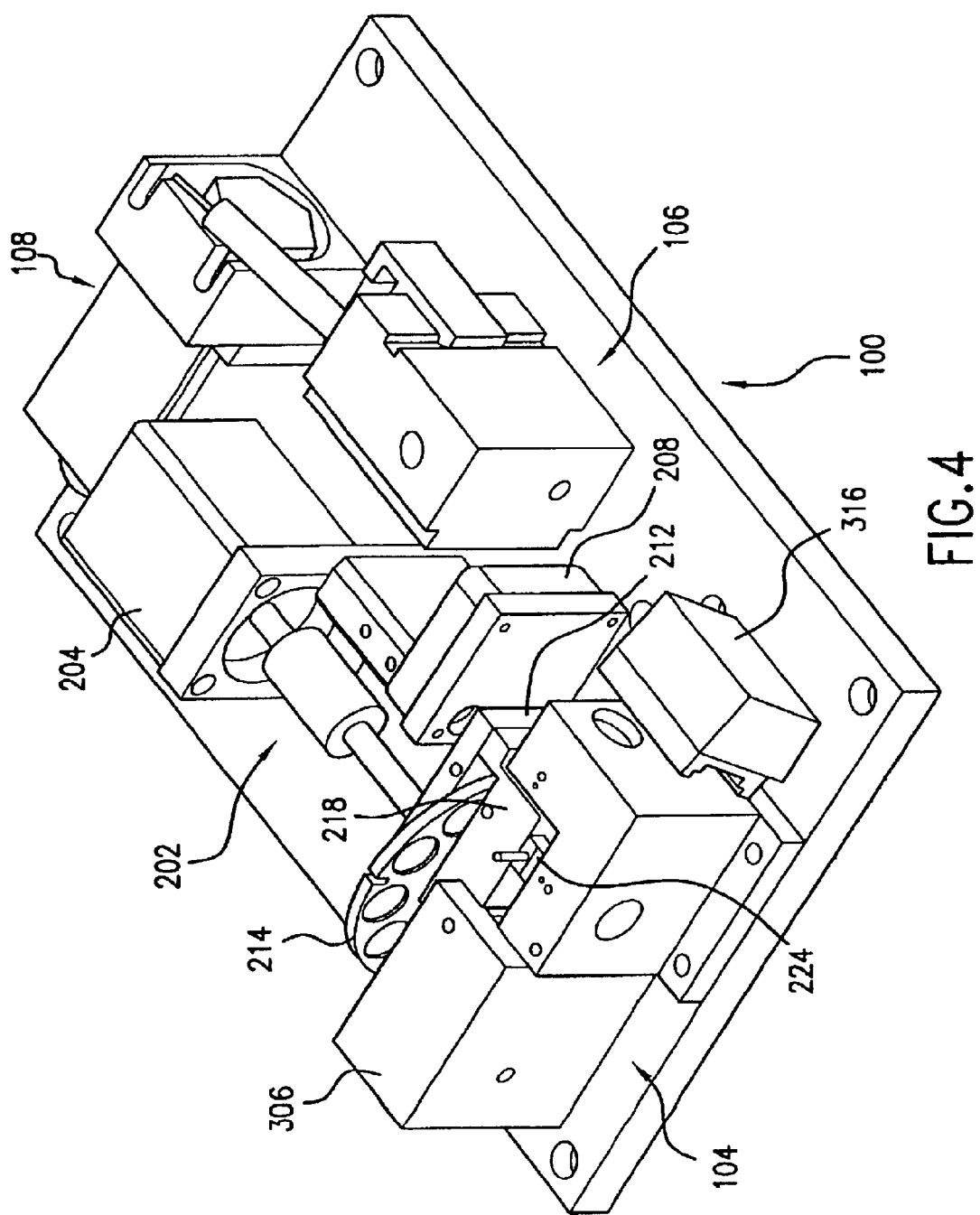
FIG. 4 is a perspective view of another embodiment of an apparatus suitable for use in this invention. In this embodiment, the unit for measuring the spectrum is a filter photometer.
Figure 5:
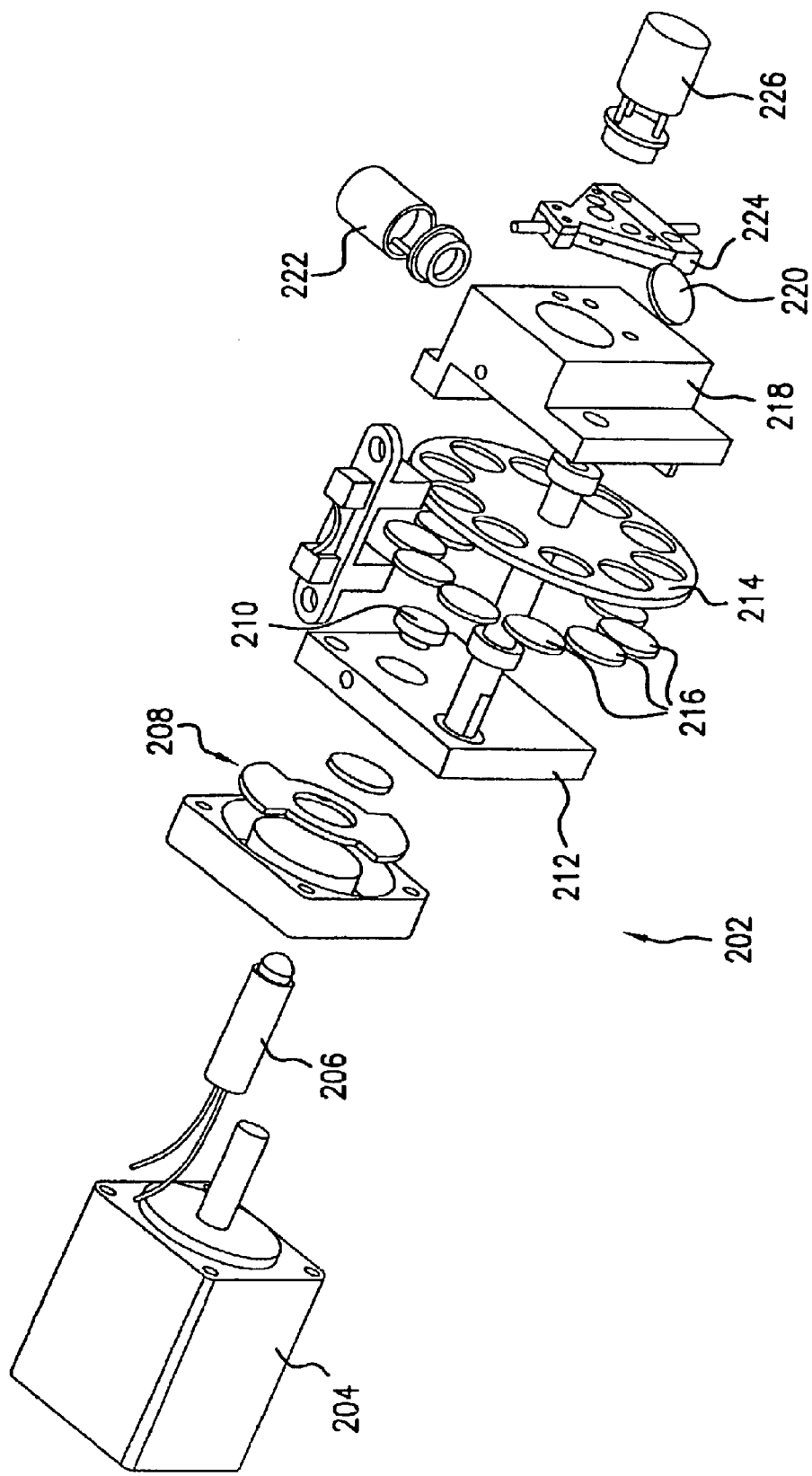
FIG. 5 is an exploded perspective view of the essential components of the unit shown in FIG. 4 for measuring the spectrum.

An alternative to the spectral measurement assembly 102 can be a filter photometer assembly 202, shown generally in FIG. 4 and in detail in FIG. 5. In FIG. 4, the remaining components of apparatus 100, namely, the refractive index determination assembly 104, the pH electrode assembly 106, and the fluid pump assembly 108 remain unchanged. Turning to FIG. 5, the filter photometer assembly 202 comprises a stepping motor 204, a source of light 206, a light source modulator 208, a collimating lens 210, a holder 212 for the collimating lens 210, a filter cartridge 214, selected filters 216, a lens holder/beam splitter assembly 218, a focusing lens (not shown), a beam splitter 220, a reference detector 222, a sample cell assembly 224, and an absorption detector 226. The functions of the foregoing components are well known to those of ordinary skill in the art. However, the functions will be briefly described in the context of the present invention. The source of light 206 provides the light for the spectral measurement. The light source modulator 208 modulates the amplitude of the beam from the source of light to allow phase-locked detection, which provides better rejection of noise. The collimating lens 210 collimates the beam of light emerging from the source of light 206. The holder 212 supports the collimating lens 210. The filters 216 select the appropriate wavelength for a measurement of absorption of a sample. The filter cartridge 214 contains the filters 216. The stepping motor 204 moves the filter cartridge 214 so that the appropriate filter 216 will be in the path of the beam of light emerging from the collimating lens 210. The lens holder/beam splitter assembly 218 holds the focusing lens and the beam splitter 220. The beam splitter 220 diverts a portion of the light entering the assembly 218 to the reference detector 222, which, as stated previously, indicates the intensity of the source of light 206. This is particularly important in order to compensate for the drift of the source of light. Light source fluctuation could result from power variation, temperature variation, and age of the source of light. The sample cell assembly 224 has a chamber that contains the biological sample undergoing the spectroscopic measurements. The focusing lens focuses the collimated light onto the biological sample in the chamber of the sample cell assembly 224. The absorption detector 226 measures the quantity of light absorbed by the biological sample. Not shown are the electronic components for processing data and controlling the functional components of the apparatus.

Figure 6:
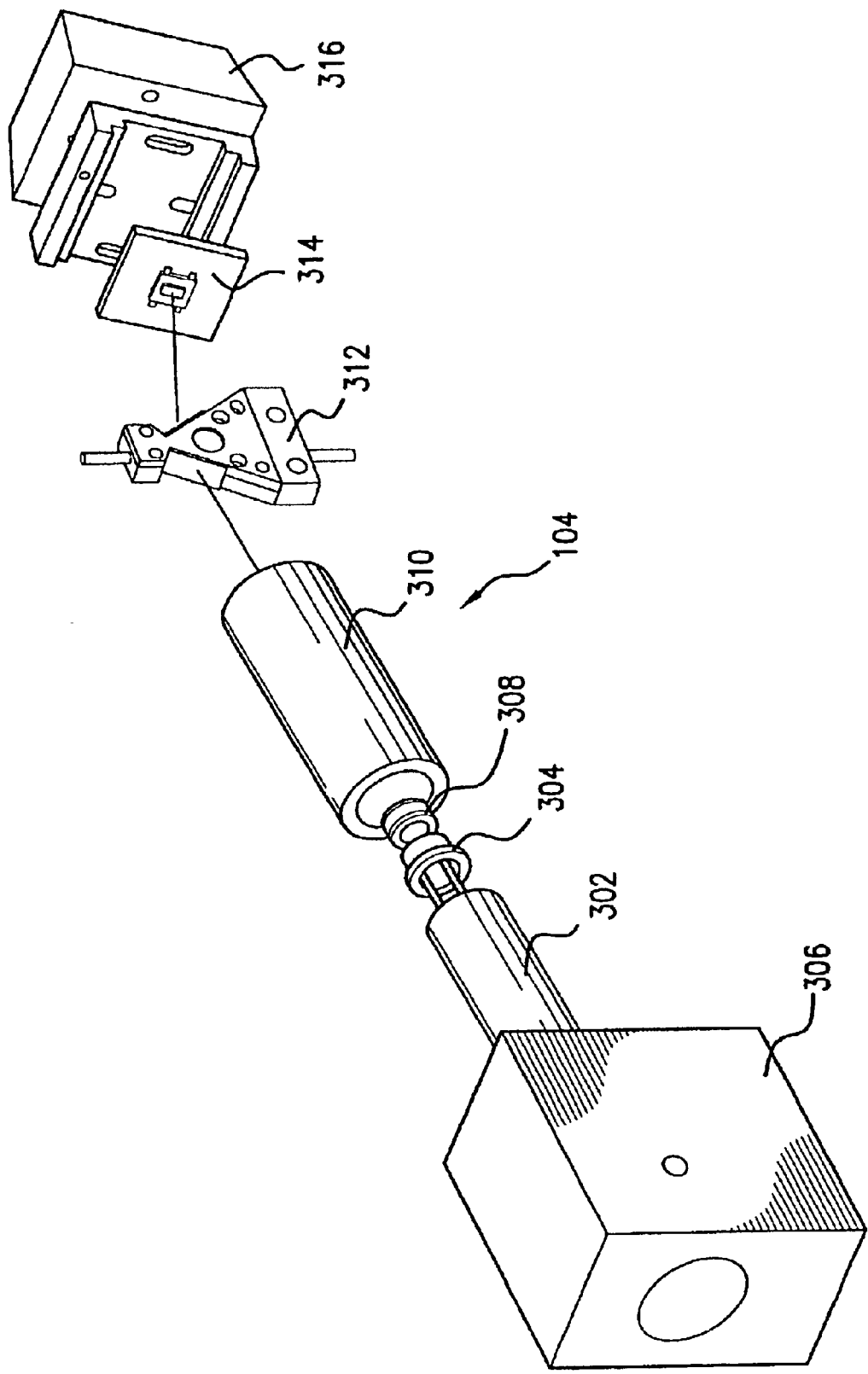
FIG. 6 is an exploded perspective view of the essential components of an assembly for determining refractive index of a sample of biological fluid.

The refractive index determination assembly 104, shown in detail in FIG. 6, comprises a sleeve 302, a source of light 304, such, for example, a laser diode emitter, a mount 306 for the sleeve 302 and the source of light 304, a lens 308, a translational mount 310 for the source of light 304, a sample cell assembly 312, a detector 314, such as, for example, a position-sensitive detector, and a mount 316 for the detector 314. The functions of the foregoing components are well known to those of ordinary skill in the art. However, the functions will be briefly described in the context of the present invention A preferred source of light for the refractive index determination is a laser. Lasers are preferred to other sources of light, such as a conventional lamp, because it is an inexpensive way to provide monochromic light, which results in better sensitivity on measuring light bending by refractive index of sample. In FIG. 6, the source of light 304 is a laser diode emitter. The sleeve 302 and the translational mount 310 function to properly align the beam from the source of light 304. The lens 308 focuses the light from the source of light 304 onto the sample cell assembly 312, which has a chamber that contains the biological sample. The detector 314 measures the change of position of the beam of light from the source of light 304 brought about by the biological sample.

The pH electrode assembly 106 can be described in a manner similar to that of the pH determination subsystem 20, which was previously described. The fluid pump assembly 108 can be described in a manner similar to that of the sampling handling subsystem 12, which was previously described.

All of the components shown in FIGS. 2, 3, 4, 5, and 6, with the exception of the sample cell assembly, are commercially available, and the apparatus in these figures can be readily assembled by one of ordinary skill in the art. It should also be noted that although sample cell assemblies 124, 224, and 312 have different reference numerals, they are intended to be identical in FIGS. 3, 5, and 6.

Figure 7:
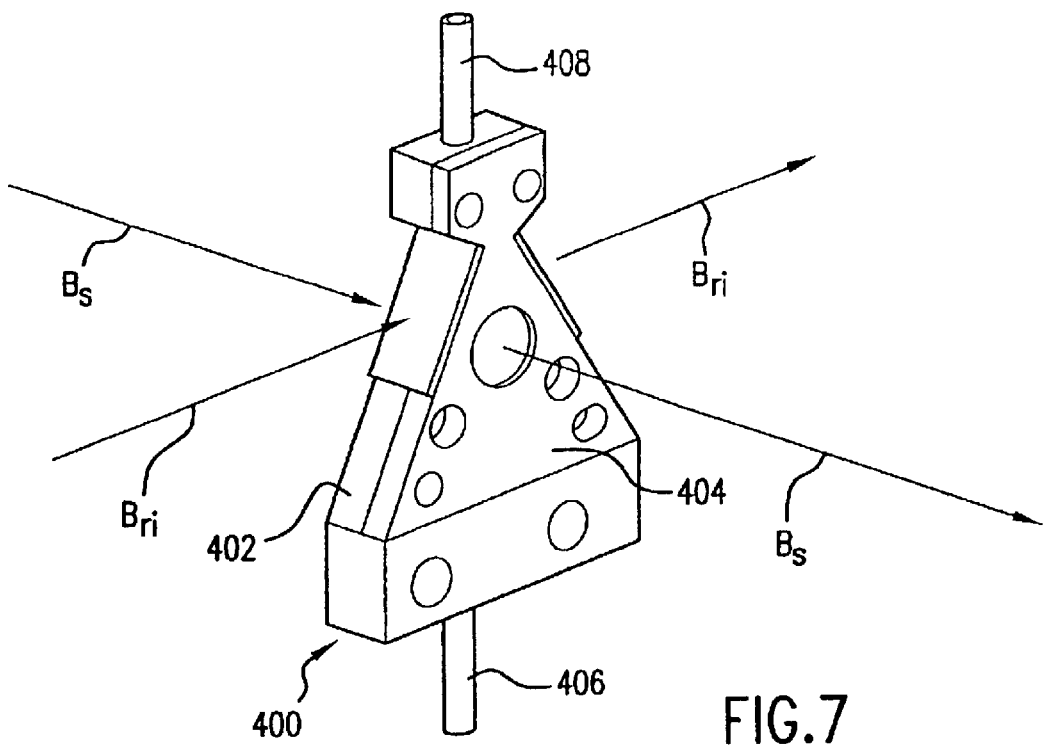
FIG. 7 is perspective view of a sample cell assembly suitable for use in this invention.

The sample cell assembly of this invention allows both spectroscopic measurements and refractive index measurements to be made with the same sample at substantially the same time. The sample cell assembly 400, shown in detail in FIGS. 7, 8, and 9A, comprises a body 402, a cover 404 for the body 402, a sample inlet tube 406, a sample outlet tube 408, a spectroscopic measurement entrance window 410 and a spectroscopic measurement exit window 412, and a refractive index measurement entrance window 414 and a refractive index measurement exit window 416. The window 410 into which the beam for conducting spectroscopic measurements enters the sample cell assembly 400 and the window 412 from which the beam for conducting spectroscopic measurements exits the sample cell assembly 400 are parallel to one another. The window 414 into which the beam beam for conducting refractive index measurements enters the sample cell assembly 414 and the window 416 from which the beam for conducting refractive index measurements exits the sample cell assembly 400 are not parallel to one another. The body 402, the cover 404, the windows 410, 412, 414, and 416 form the boundaries of a chamber that contains the biological sample. As shown in FIG. 7, the beam for spectroscopic measurements $B_s$ and the beam for measuring refractive index $B_{ri}$ are propagated through the sample cell assembly 400 such that the beam for spectroscopic measurements does not interfere with the beam for measuring refractive index and vice versa.

The interior of the sample cell assembly 400, i. e., the chamber that contains the biological sample, is divided into three zones: (1) an expansion zone 418, (2) a read zone 420, and (3) a contraction zone 422. In the expansion zone 418, the flow front of the sample expands. The expansion zone 418 is designed such that the amount of surface area in contact with the fluid is minimized to reduce the likelihood of bubble formation caused by fluid clinging to the interior surfaces of the sample cell assembly and to minimize cleaning requirements of the interior surfaces of the sample cell assembly. The expansion zone 418 is also designed to eliminate regions where fluid may become trapped, thereby resulting in difficulties in washing the interior surfaces of the sample cell assembly for subsequent samples. In the contraction zone 422, the flow front of the sample contracts. Like the expansion zone 418, the contraction zone 422 is also designed such that the amount of surface area in contact with the fluid is minimized to reduce the likelihood of bubble formation caused by fluid clinging to the interior surfaces of the sample cell assembly and to minimize cleaning requirements of the interior surfaces of the sample cell assembly. The read zone 420 for absorption measurements should be large enough to allow the absorption beam to pass through the entrance window and the exit window without being substantially truncated. The read zone 420 for refractive index measurements should be large enough to allow the refractive index beam to pass through the entrance window and the exit window without being substantially truncated. The read zones for the absorption measurements and the refractive index measurements may coincide or they may not, depending on system design considerations. The read zones 420 for the absorption measurements and refractive index measurements in FIGS. 7, 8, and 9A are shown to coincide, thereby reducing required sample volume.

Figure 8:
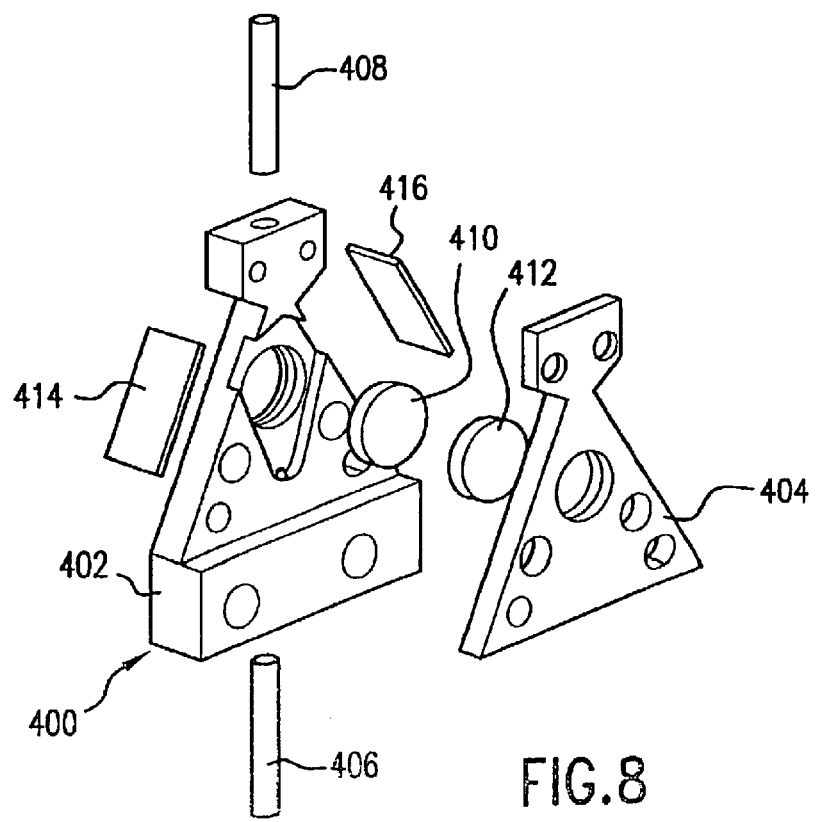
FIG. 8 is an exploded perspective view of the sample cell assembly shown in FIG. 7.
Figure 9A:
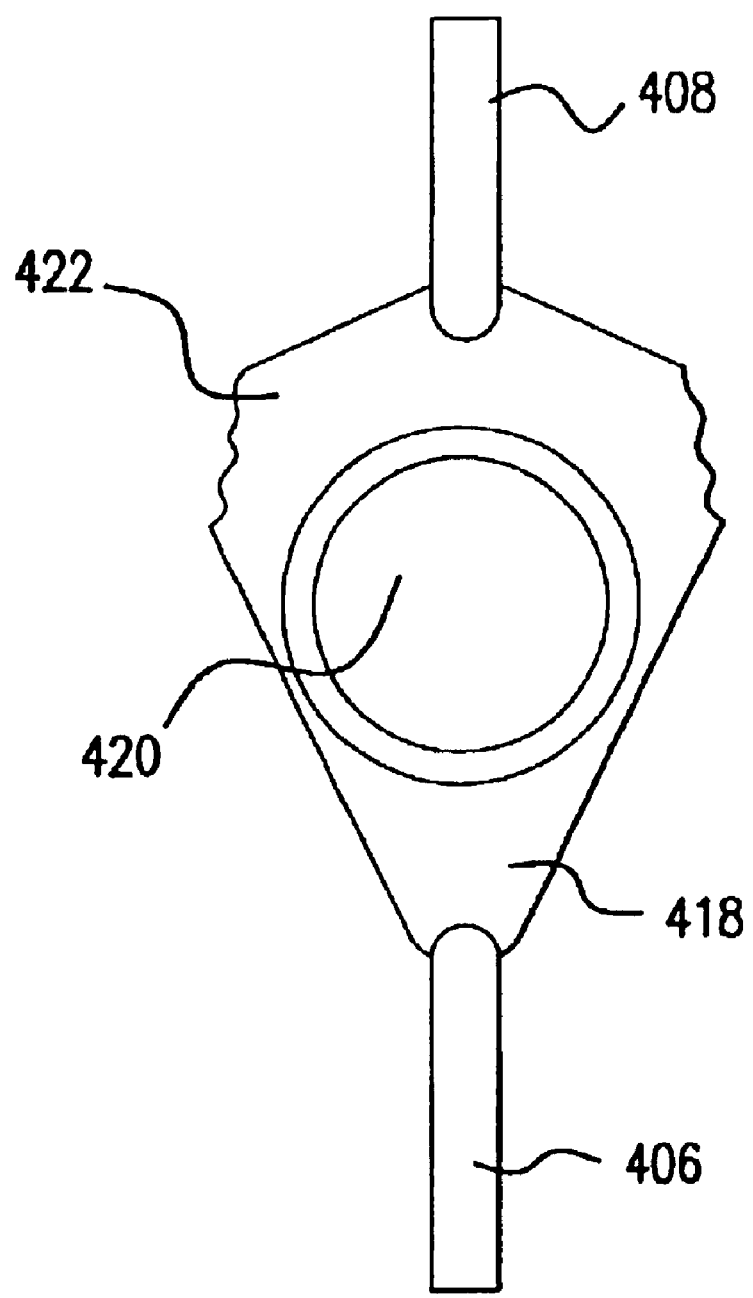
FIG. 9A is an enlarged elevational view of one embodiment of the interior of the sample cell assembly shown in FIG. 7.
Figure 9B:
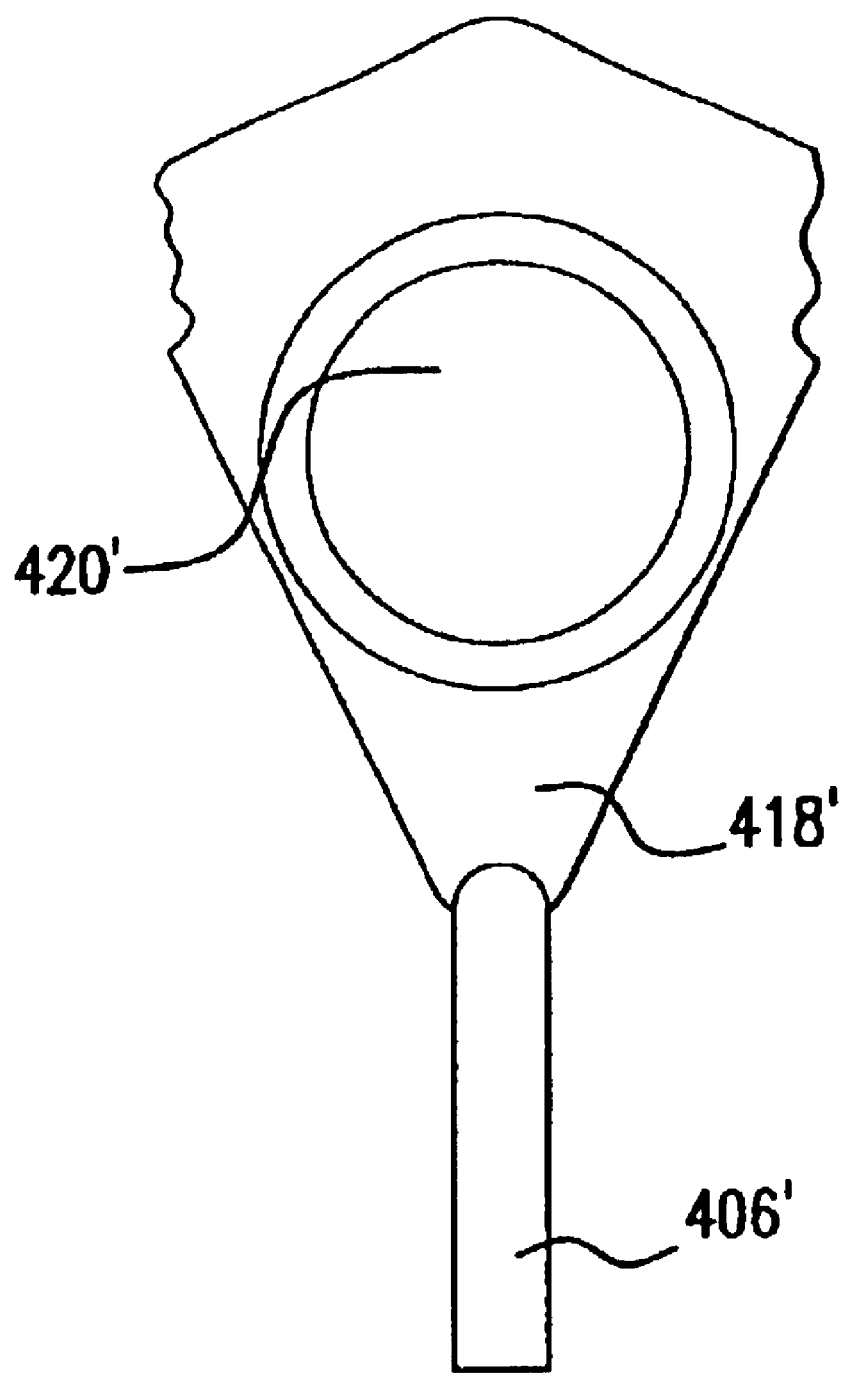
FIG. 9B is an enlarged elevational view of another embodiment of the interior of the sample cell assembly shown in FIG. 7.

In the sample cell assembly 400 shown in FIGS. 7, 8, and 9A, the sample flows into the inlet tube 406 and through the contraction zone 422 to the read zone 420, where it resides during the time needed for optical readings. After the optical readings are taken, the sample flows from the read zone 420 through the contraction zone 422, and is then removed from the sample cell assembly 400 by means of flowing through the outlet tube 408. In an alternative embodiment, shown in FIG. 9B, the sample enters and exits the sample cell assembly by way of the inlet tube 406'. The sample cell assembly of the alternative embodiment does not have an outlet tube distinct from the inlet tube 406'. In the alternative embodiment, the sample flows into the inlet tube 406' and through the expansion zone 418' to the read zone 420', where it resides during the time needed for optical readings. After the optical readings are taken, the sample sample flows from the read zone 420' back though the expansion zone 418', and is then removed from the sample cell assembly by means of flowing back through the inlet tube 406'. In the alternative embodiment, the expansion zone 418' serves as the contraction zone when the sample is removed from the sample cell assembly.

The sample cell assembly of this invention can be used to simultaneously measure refractive index and ultraviolet, visible, or infrared spectrum. While not preferred, it is acceptable to replace the sample cell assembly of this invention with two or more sample cell assemblies in tandem for separate measurements.

Materials for forming the windows of the sample cell assembly are well known to those of ordinary skill in the art. However, parameters of the most critical materials of the sample cell assembly will now be described to clearly set forth the important features of the sample cell assembly. Spectroscopic measurement windows 410 and 412 are preferably formed from glass or fused silica, and refractive index measurement windows 414 and 416 are preferably formed of glass, fused silica, or polymeric materials. The distance between the spectroscopic measurement windows 410 and 412 preferably ranges from about 100 $\mu$m to about 5 cm, more preferably 1 mm. The angle between the refractive index measurement windows 414 and 416 preferably ranges from about 5° to about 60°, more preferably 30°. Wavelengths of light suitable for refractive index measurement preferably ranges from about 500 nm to about 1000 nm. Wavelengths of light suitable for spectroscopic measurement preferably ranges from about 300 nm to about 2500 nm. The volume of the interior of the sample cell assembly, i. e., the chamber that contains the biological sample, is not critical; however, it is preferred that the volume of the interior of the sample cell assembly be of sufficient size so that it can contain a sufficient volume of sample for the desired optical measurements.

The method of this invention differs from that disclosed in U.S. Pat. No. 5,696,580, which proposes measuring absorbance and refractive index through a sample cell assembly having at least one face of the sample cell assembly tilted with respect to the axis along which the beam used for absorption propagates. In U.S. Pat. No. 5,696,580, the beam of infrared light and the beam of light for measuring refractive index travel in the same direction through the sample cell assembly. This common path for the two beams leads to two significant problems.

First, a sample cell assembly having a triangular shape (as described in U.S. Pat. No. 5,696,580) makes implementation of an array spectrometer difficult. An array spectrometer must be used for measurements of analytes in urine in order to increase the speed of analysis. In an array spectrometer, the light rays are fanned out as a function of wavelength. The fanned out light rays are projected onto an array detector such that each detector element of the array detector observes a different wavelength. If the fanned out light rays are first transmitted through the triangular-shaped sample cell assembly, then the detector element that each light ray strikes will change as the refractive index of the urine sample changes. Compensation for this effect is complicated, requires excessive computation, and will introduce its own sources of noise.

Second, if an array spectrometer cannot be employed, a scanning spectrometer must be used. Measurement of the refractive index and absorption in a scanning spectrometer would require a split aperture detector. A split aperture detector is one in which the detector area comprises two independent detectors that are joined in the center. Calibration is problematic if there is a gap, which is referred to as a dead zone, between the detectors. A dead zone is an area in which the device does not respond to the light. Practically, a dead zone cannot be avoided because the two detectors cannot be butted together perfectly. The larger the dead zone, the more problematic the calibration. The reason for the difficulty in calibration is that the beam does not have a uniform intensity distribution when it is projected onto the detector. If the beam is translated slightly, a different part of the beam strikes the dead zone. If the intensity of the beam is not uniform, then the measured intensity will change as the beam moves across the dead zone. Because the beam is intended to move across the split aperture detector, the presence of the dead zone will be a source of error. The larger the dead zone, the larger the error.

In the method of this invention, the beam for refractive index measurements and the beam for spectroscopic measurements are not co-linear. The absorption measuring beam passes through a sample cell assembly having plane parallel windows. Thus, scanning spectrometers and array spectrometers can both be employed in the usual way with established performances.

The method of this invention preferably employs a position-sensitive detector that works in the visible spectrum and is designed to eliminate a dead zone—it is not a split aperture detector.

Mathematical assumptions and relationships that are essential to the understanding of the operation of this invention will now be described.

Figure 10:
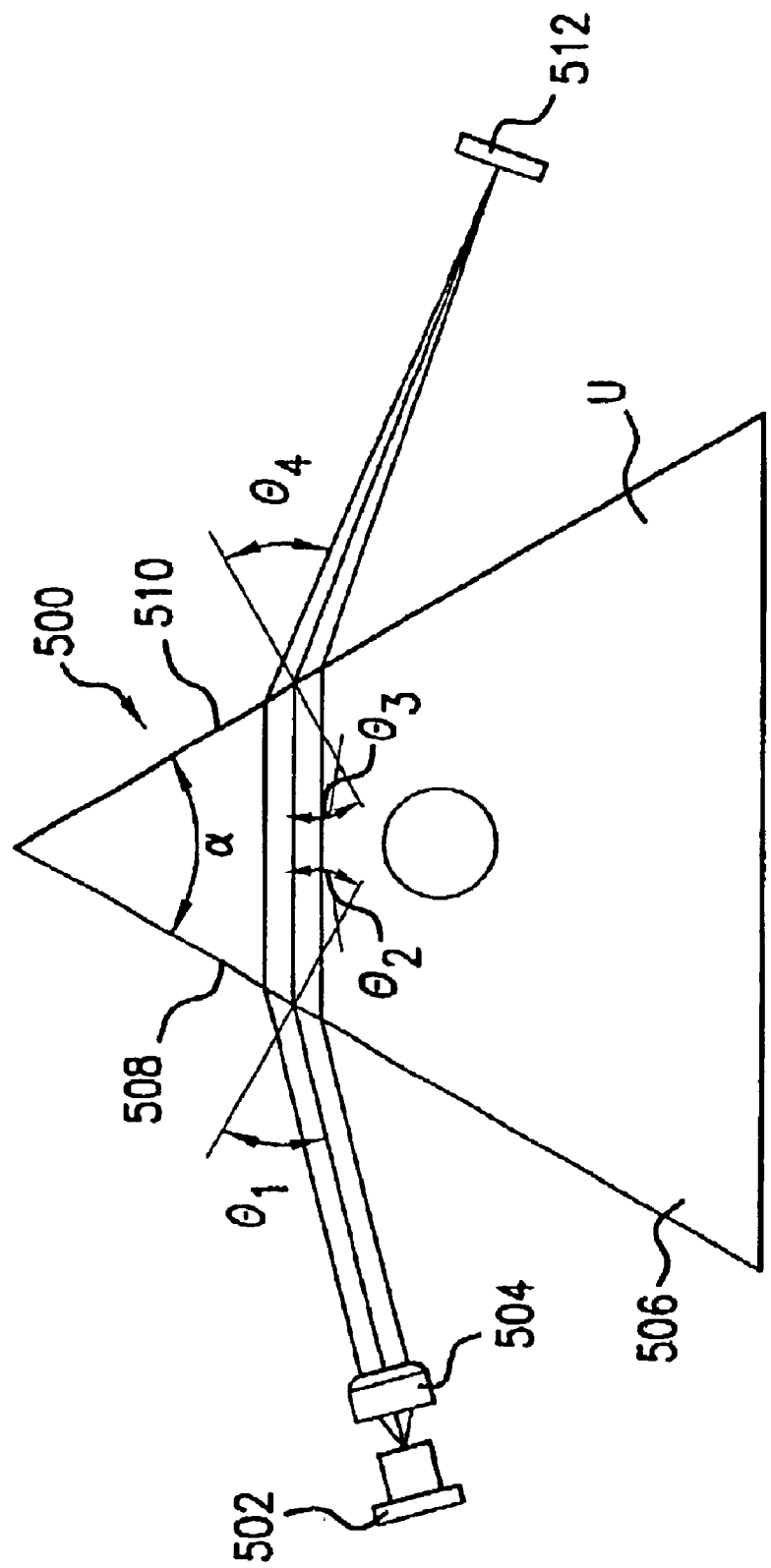
FIG. 10 is a schematic view of an arrangement for determining the refractive index of a biological fluid, wherein the sample-containing chamber of the sample cell assembly of this invention is in the form of a prism. In this figure, the beams of light employed to determine refractive index of a biological fluid are shown and characterized.

FIG. 10 illustrates an arrangement for determining the refractive index of a biological fluid, wherein the sample containing sample-containing chamber of the sample cell assembly of this invention is in the form of a prism. In the arrangement 500 for determining refractive index of a sample of biological fluid, a source of light 502 provides a beam of light, which is collimated by a lens 504. The beam of collimated light enters the chamber 506 of the sample cell assembly. The beam of light for measuring refractive index is incident on a window 508 of the chamber 506 of the sample cell assembly at an angle of $\theta_1$ degrees; the beam refracts into the chamber 506 of the sample cell assembly and then into the sample "U". The relationship between the incident angle and the angle of the beam inside the chamber 506 of the sample cell assembly is given by $$n_0 \sin(\theta_1) = n_s \sin(\theta_2) \quad (1)$$

where $n_0$ represents the refractive index of air (1.000) and $n_s$ represents the refractive index of the sample.

This relationship is independent of the refractive index of the material of the entrance window 508 of the chamber 506 of the sample cell assembly. The relationship between the incident angle of the beam at an exit window 510 of the chamber 506 of the sample cell assembly ($\theta_3$) and the angle of the beam outside the sample cell assembly ($\theta_4$) is given by $$n_s \sin(\theta_3) = n_0 \sin(\theta_4). \quad (2)$$

Solving for $\theta_4$ in terms of the refractive index of the sample and the incident angle $\theta_1$, $$\theta_4 = \sin^{-1}\left[n_s \sin\left(\alpha - \sin^{-1}\left[\frac{\sin(\theta_1)}{n_s}\right]\right)\right] \quad (3)$$

where $\alpha = \theta_2 + \theta_3$.

For small changes in refractive index, equation (3) becomes a linear function of the refractive index $$\theta_4 = A n_s + B \quad (4)$$

where A and B are constants. The displacement on the detector 512 is given by $$D = A' n_s + B' \quad (5)$$

where

A' and B' are constants that are determined in a calibration step, and

D represents the displacement on the detector.

A two-point calibration can be used to determine the two unknown constants. The first calibration point could be done with water (refractive index n=1.333) and the second calibration point could be made with a solution having a refractive index of 1.450. These two measurements would determine the relationship between L and the refractive index (slope and intercept) that can be used to determine subsequent refractive indices of solutions from the measured beam displacements. Additional calibration solutions can be measured so that a least squares fit can be used to determine the two unknown constants.

Figure 11:
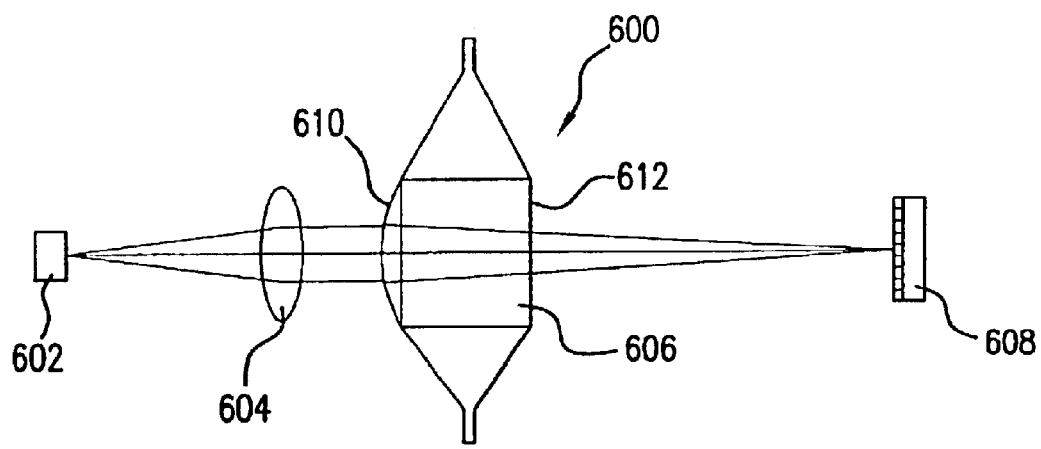
FIG. 11 is a schematic view of an arrangement for determining the refractive index of a biological fluid, wherein the entrance window of the sample containing sample-containing chamber of the sample cell assembly of this invention is curved.

FIG. 11 illustrates an arrangement for determining the refractive index of a biological fluid, wherein at least one window of the sample-containing chamber of the sample cell assembly of this invention is curved. In the refractive index determination arrangement 600 shown in FIG. 11, a source of light 602 transmits a beam of light through a collimating lens 604. The beam of collimated light emerging from the lens 604 enters the chamber 606 of the sample cell assembly. The beam of light emerging from the chamber 606 of the sample cell assembly is detected by a detector 608, preferably a detector having a plurality of detection elements. In the chamber 606 of the sample cell assembly, at least one window of the chamber 606 of the sample cell assembly is curved so that the chamber 606 of the sample cell assembly no longer operates in the manner of a prism, but rather operates in the manner of a lens. As shown in FIG. 11, an entrance window 610 of the chamber 606 of the sample cell assembly is curved and an exit window 612 is straight. However, the exit window 612 can also be curved, or the entrance window 610 can be straight and the exit window 612 can be curved. As the refractive index of the biological sample changes, the power of the "lens" formed by the chamber 606 of the sample cell assembly also changes. Consequently, the point, i.e., the focal point, to which the "lens" formed by the chamber 606 of the sample cell assembly focuses the beam of light emerging from the sample cell assembly also changes. The detector 608 is in a fixed position relative to the "lens" formed by the chamber 606 of the sample cell assembly. This position is near the focal point "P" of the "lens" formed by the chamber 606 of the sample cell assembly. The focal point "P" is the focal point when the sample in the chamber 606 of the sample cell assembly is water. The size of the spot of the beam of light striking the detector 608 will change as the focal point "P" changes. The size of the spot of the beam of light striking the detector 608 is proportional to the refractive index of the biological sample, i.e., as the refractive index of the biological sample changes, the size of the spot of the beam of light striking the detector 608 changes. The shape of the chamber 606 of the sample cell assembly is not preferred over a chamber of a sample cell assembly having a prism configuration, because the former is more sensitive to scattering from particulate material in the biological sample, but it would be expected to be suitable for many applications.

Figure 12:
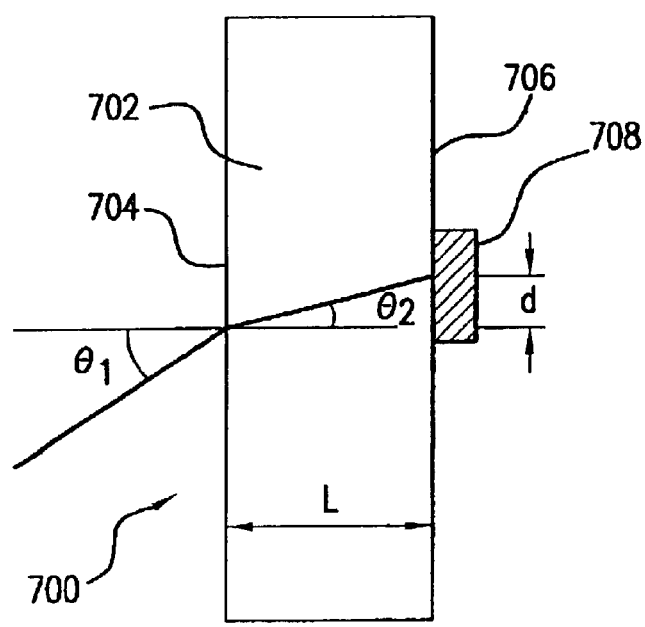
FIG. 12 is a schematic view of an arrangement for determining the refractive index of a biological fluid, wherein a portion of the sample-containing chamber of the sample cell assembly is shown. In this portion, the window where the light beam enters the chamber is parallel to the window where the light beam exits the chamber.

FIG. 12 illustrates an arrangement 700 for use in determining the refractive index of a biological fluid comprising a sample-containing chamber 702 of a sample cell assembly, wherein an entrance window 704 of the chamber 702 of the sample cell assembly is parallel to an exit window 706 of the chamber 702 of the sample cell assembly. Although not shown in FIG. 12, this arrangement also employs components than generate and collimate a beam of light, equivalent to that shown in FIG. 11.

The entrance window 704 and the exit window 706 are parallel to one another. A detector 708, preferably a position-sensitive detector, is positioned substantially adjacent to the exit window 706 of the chamber 702 of the sample cell assembly to receive the refracted beam of light. As used herein, the expression "substantially adjacent" includes both in contact with and at a small separation. The beam of light for determining the refractive index is incident on a first surface of the entrance window 704 at an angle $\theta_1$, which is greater than zero. Preferably, this angle ranges from about 45° to about 85°. Less preferably, this angle can range from about 5° to about 45°. The distance between the entrance window 704 and the exit window 706 preferably exceeds 5 mm, but can be less. The equation relating refractive index to the position of the beam on the detector is $$d = \frac{L}{n}\sin(\theta_1) \quad (6)$$

where
- L represents the distance between the entrance window and the exit window,
- n represents the refractive index of the sample inside the sample-containing chamber of the sample cell assembly, and
- d represents the vertical distance between the position at which the beam of light enters the sample-containing chamber of the sample cell assembly and exits the sample-containing chamber of the sample cell assembly.

The methods of spectroscopic analysis of this invention are not limited to absorption spectroscopy. All methods of spectroscopic analysis are contemplated for use with this invention, and, in particular, those spectroscopic analysis techniques set forth in Skoog and West, *Principles of Instrumental Analysis*, Second Edition, Saunders College/Holt, Rinehart and Winston (Philadelphia:1980), pp. 113–351, incorporated herein by reference and B. Henderson, *Handbook of Optics*, 2nd edition, McGraw-Hill (New York: 1995), chapter 20, incorporated herein by reference. These spectroscopic analysis techniques include, but are not limited to, ultraviolet spectroscopy, including ultraviolet scattering spectroscopy, visible spectroscopy, including visible scattering spectroscopy, infrared spectroscopy, including infrared scattering spectroscopy, fluorescence spectroscopy, and Raman spectroscopy. Also included is spectroscopic analysis utilizing measurement of transmitted light and spectroscopic analysis utilizing measurement of reflected light. Common practices in spectroscopy are detection of transmitted light to measure light intensity after a portion of the light is absorbed by a clear liquid sample and detection of reflected light to measure light intensity after a portion of the light is absorbed or scattered by a turbid liquid or a solid sample. Scattering spectroscopy may be defined as measuring (a) the attenuation of light caused by propagation of light through a medium that is capable of absorbing and scattering light, or (b) the attenuation of light caused by specular and diffuse reflection of light from an absorptive sample.

The method and apparatus of this invention not only removes base-line drift from the measured spectra, but also prominently displays spectral features unique to the analytes of interest. Removal of base-line drift, separation of spectral features, and noise reduction are necessary for spectroscopic analysis to provide accurate results. Derivative spectroscopy is a technique that can be used to bring about noise reduction. Derivative spectrophotometry is defined in Skoog and West, *Principles of Instrumental Analysis*, Second Edition, Saunders College/Halt, Rinehart and Winston (Philadelphia:1980), pp. 192–194, incorporated herein by reference. See also, B. Henderson, *Handbook of Optics*, 2nd edition, McGraw-Hill (New York:1995), chapter 20, incorporated herein by reference. Derivative spectroscopy, as used herein, will now be described.

The spectrum of urine comprises the spectrum of water plus the spectra of urea, creatinine, glucose, ketones, and many other chemical substances dissolved in the urine. The calibration process described herein can determine a mathematical operator (i.e., a model) that will simultaneously convert the absorption spectrum of a urine specimen into the concentration values of chemical components of interest in the urine specimen.

Beer's Law relates the absorbance of a chemical substance (a), the concentration of the substance (c), and the path length of the light (L) to the ratio of intensity of incident light ($I_o$) to intensity of transmitted light (I), $$\frac{I}{I_0} = e^{-Lca} \quad (7)$$

$$s_{q,1} = -\log\left(\frac{I_q}{I_{0,q}}\right) = Lc_n a_{q,n} \quad (8)$$

where
- $S_{q,n}$ represents the $q^{th}$ element (wavelength) of the $n^{th}$ analyte of the sample,
- L represents the path length of the light,
- $c_n$ represents the concentration of the $n^{th}$ analyte in the sample, and
- $a_{q,n}$ represents the $q^{th}$ element of the spectrum for the $n^{th}$ analyte,
- $I_{o,q}$ represents the intensity of the incident light for the $q^{th}$ wavelength,
- $I_q$ represents the intensity of the transmitted light for the $q^{th}$ wavelength.

The absorption spectrum S for urine can be expressed by the equation $$S = L[c_w a_w + c_1 a_1 + c_2 a_2 \ldots + c_n a_n \ldots + c_N a_N] \quad (9)$$

where
- $c_w a_w$ represents the product of the concentration of water and spectrum of water,
- $c_n a_n$ represents the product of the concentration of the $n^{th}$ analyte and absorption of the $n^{th}$ analyte,
- $c_N a_N$ represents the product of the concentration of the $N^{th}$ (final)analyte and spectrum of the $N^{th}$ (final) analyte, and L is as previously defined.

Figure 13:
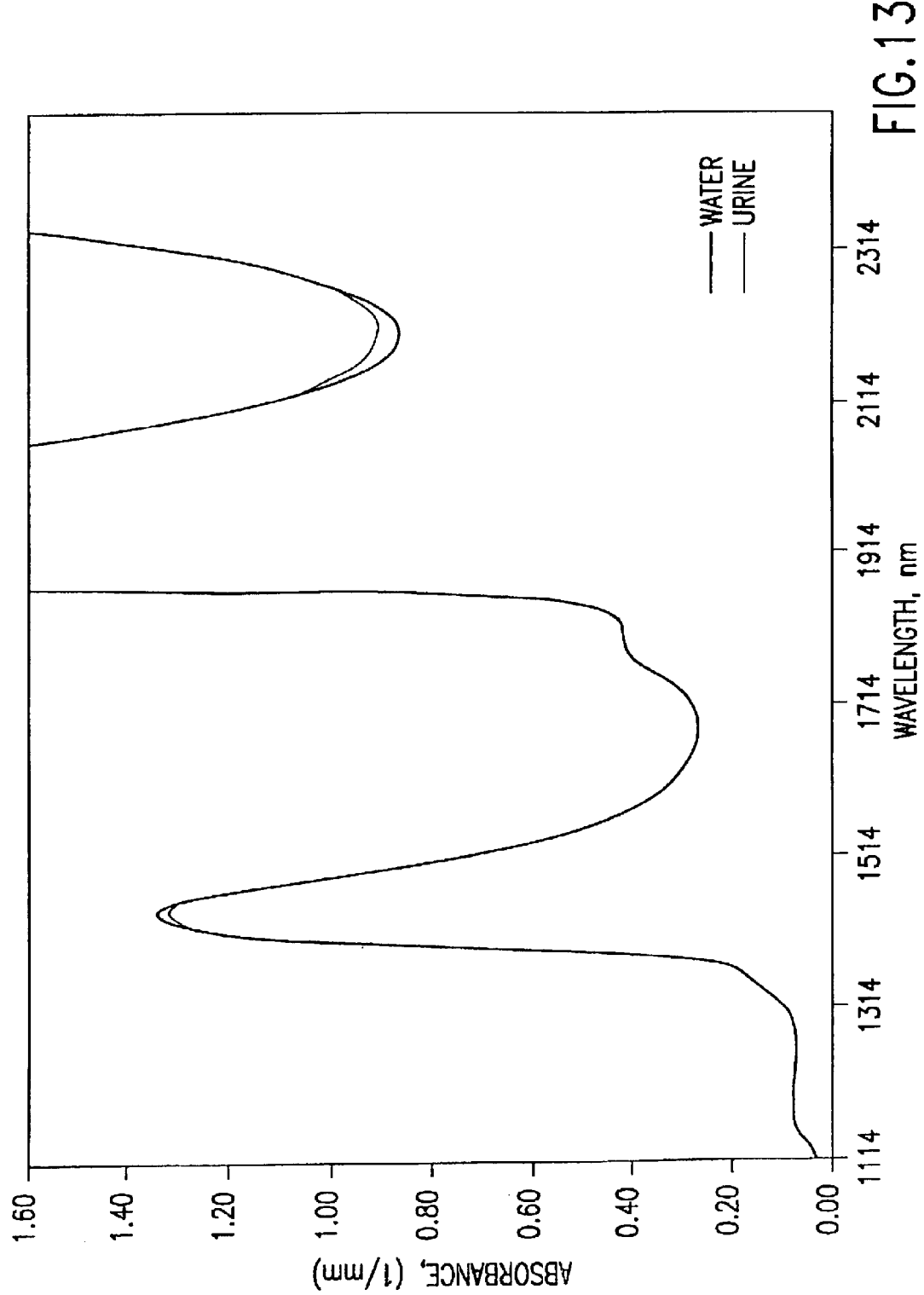
FIG. 13 is a graph showing spectra of both water and a sample of urine.

The spectrum of an aqueous liquid, e.g., urine, for the ideal case does not consider noise and base-line drift, which are integral parts of the measurement process. The measured spectra of aqueous liquids are often unsuitable for analytical treatment. FIG. 13 shows the absorption spectrum of water and the absorption spectrum of urine. The solid black line is the absorption spectrum of water and the dotted black line is the absorption spectrum of urine. In order to clearly feature the spectrum of an analyte of interest, e. g., urea, the water background must be subtracted from the spectrum of the aqueous solution containing the analyte of interest, e. g., urine. Because each point on each spectrum is a large number, and because one large number must be subtracted from another large number to observe a small difference, both of the spectra must be determined very precisely. Because practical considerations, such as noise, limit the precision of the spectral measurements, methods must be developed to deal with the noise in order to make spectroscopy useful for accurately recovering the concentration values of analytes in an aqueous solution, e. g., urine.

As a first step, base-line drift must be removed from the data. A base-line drift as low as 1% can cause large errors in the determination of the concentration of an analyte. By taking a first derivative of the spectrum of a biological sample, changes in the base-line signal can be removed. The derivative provides two features. First, it removes the base-line drift from the measured spectrum, and second, it brings to prominence the weaker features in the spectrum that carry analytical information.

In the presence of base-line drift, equation (8) becomes $$s_{q,n} = -\log\left(\frac{I_{q,n}}{(I_{0,q,n} + \Delta I_{0,q,n})}\right) = \tag{10}$$

$$-\log\left[\frac{I_{q,n}}{I_{0,q,n}}\right] + \left[\frac{\Delta I_{0,q,n}}{I_{0,q,n}}\right] + \frac{1}{2}\left[\frac{\Delta I_{0,q,n}}{I_{0,q,n}}\right]^2 + \ldots =$$

$$Lc_q a_{q,n} + \left[\frac{\Delta I_{0,q,n}}{I_{0,q,n}}\right] + \frac{1}{2}\left[\frac{\Delta I_{0,q,n}}{I_{0,q,n}}\right]^2 + \ldots$$

where $I_{q,n}$ represents the intensity of light transmitted by the sample at the $q^{th}$ wavelength, $I_{0,q,n}$ represents the intensity of light incident on the sample at the $q^{th}$ wavelength, and $\Delta I_{0,q,n}$ represents the drift in the intensity of incident light at the $q^{th}$ wavelength.

The above expression (10) can be generalized for other sources of drift, such as, for example, detector drift and electronics drift. Most sources of drift, including source, detector, and electronics drift, are sufficiently spectrally flat, i.e., lacking in spectral features such as peaks and valleys, that taking the derivative is helpful in removing the drift.

To first order approximation, which is a good approximation for small amounts of drift, $$s_q = Lc a_q + \left[\frac{\Delta I_{0,q}}{I_{0,q}}\right] \tag{11}$$

If the base-line drift on the spectrometer is spectrally flat, which is typically the case, then the dependence of the drift on wavelength is small, and the derivative of the drift with respect to wavelength is very small. To a very good approximation $$\frac{ds_q}{d\lambda} = Lc\frac{da_q}{d\lambda} \tag{12}$$

Thus, the drift can be eliminated from the measurement.

Figure 14:
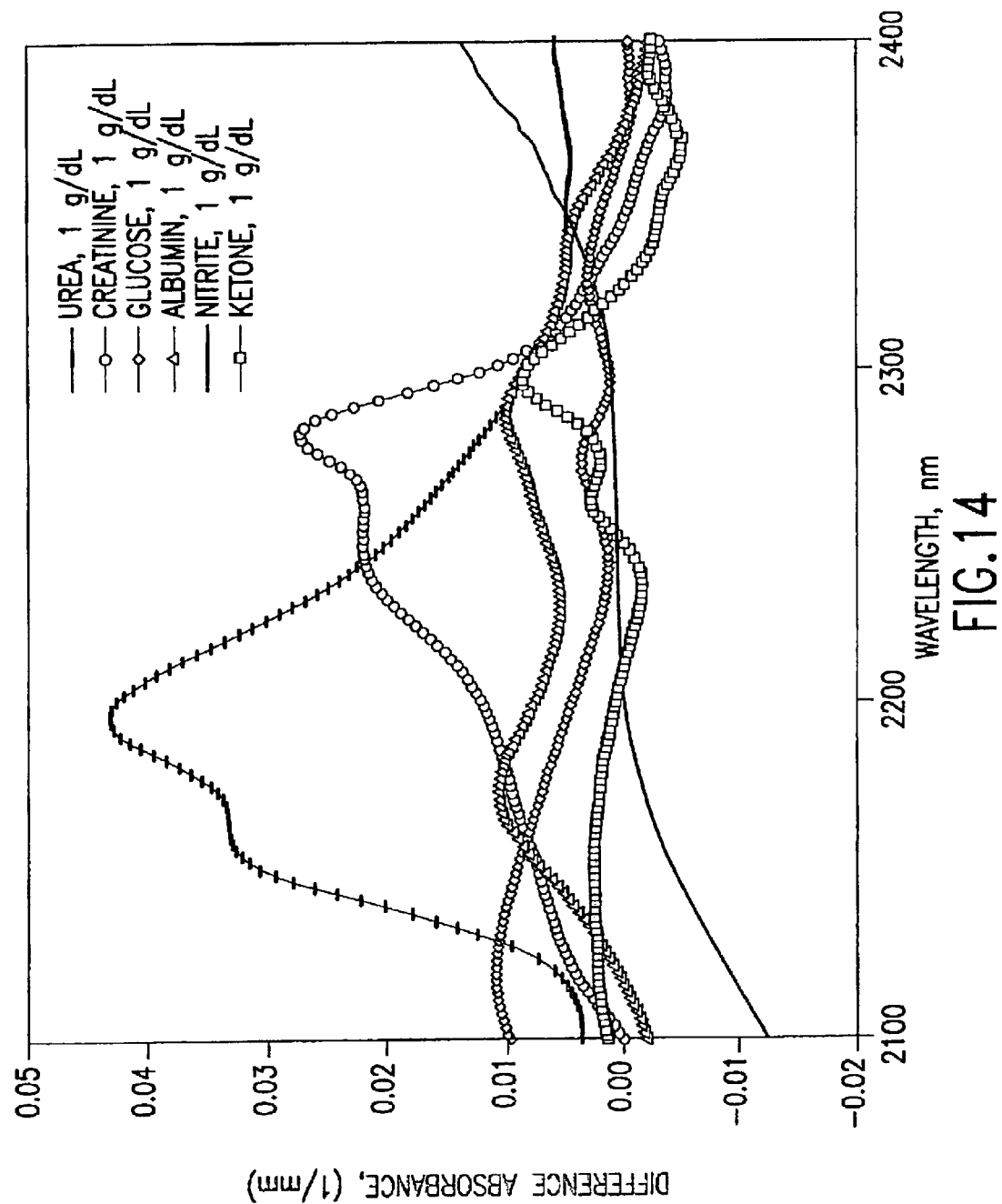
FIG. 14 is a graph showing spectra of urea, creatinine, glucose, albumin, ketones, and nitrites from a sample of urine after the spectrum of water has been subtracted.
Figure 15:
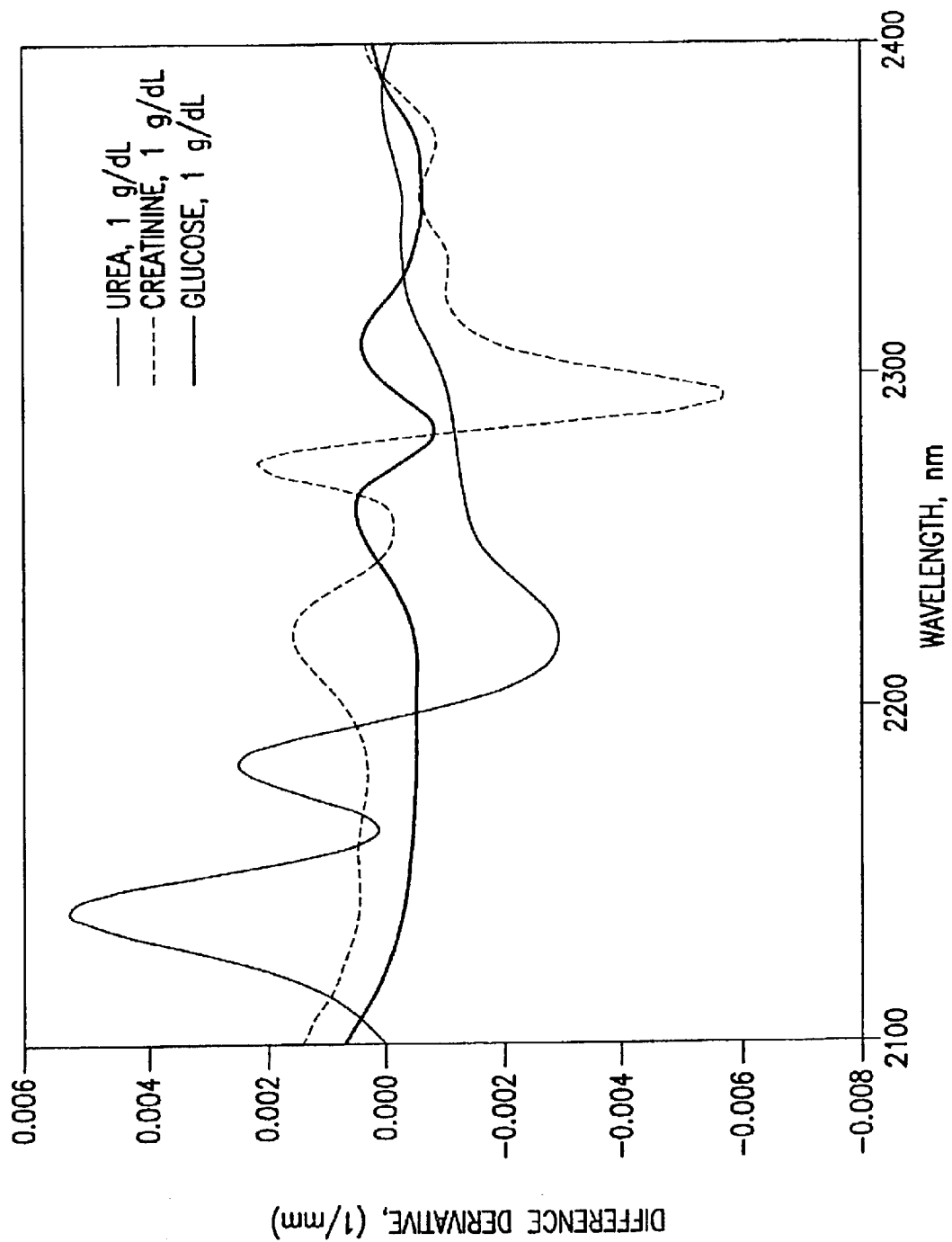
FIG. 15 is a graph showing the derivative spectra of urea, creatinine, and glucose.
Figure 16:
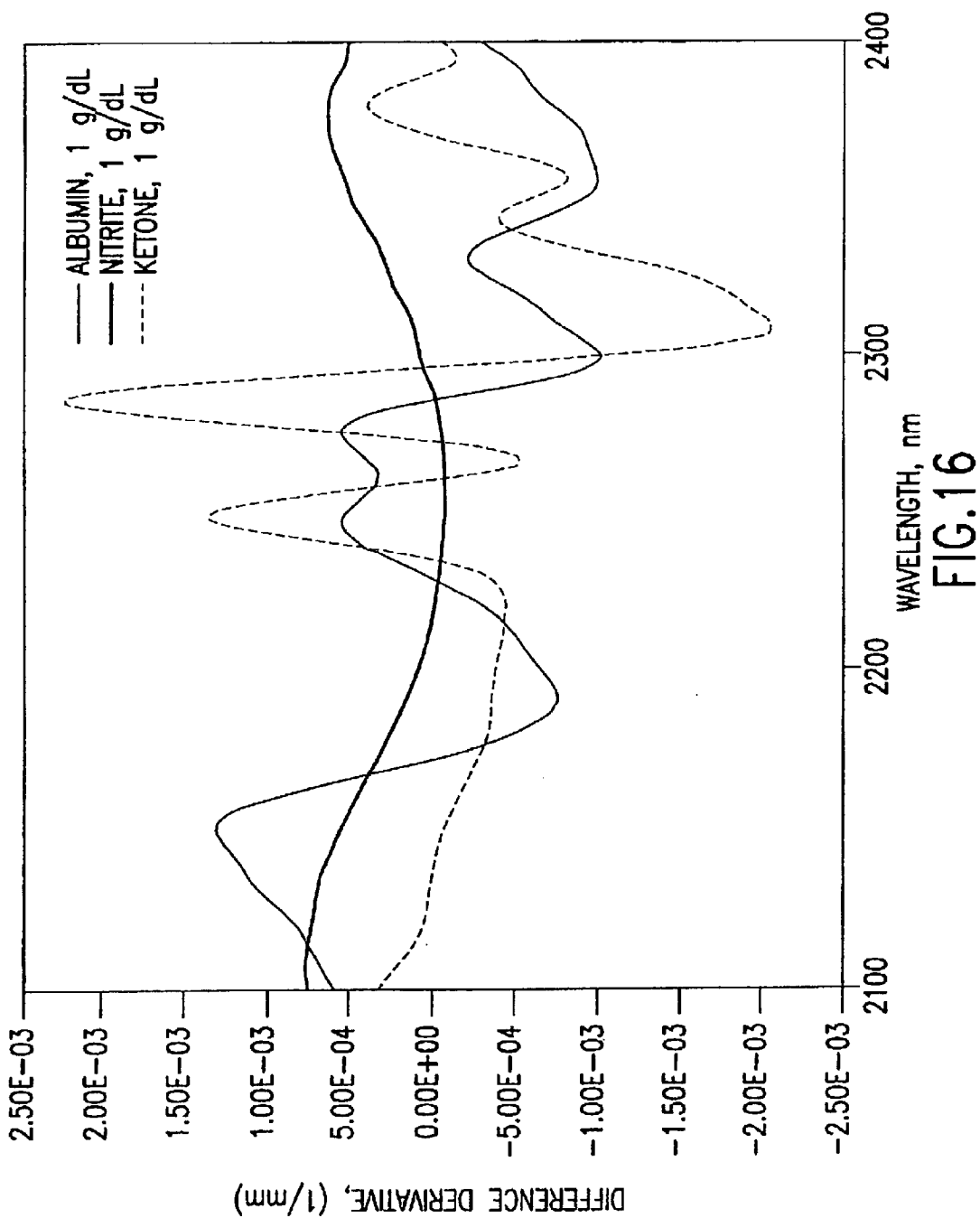
FIG. 16 is a graph showing the derivative spectra of albumin, nitrites, and ketones.
Figure 17:
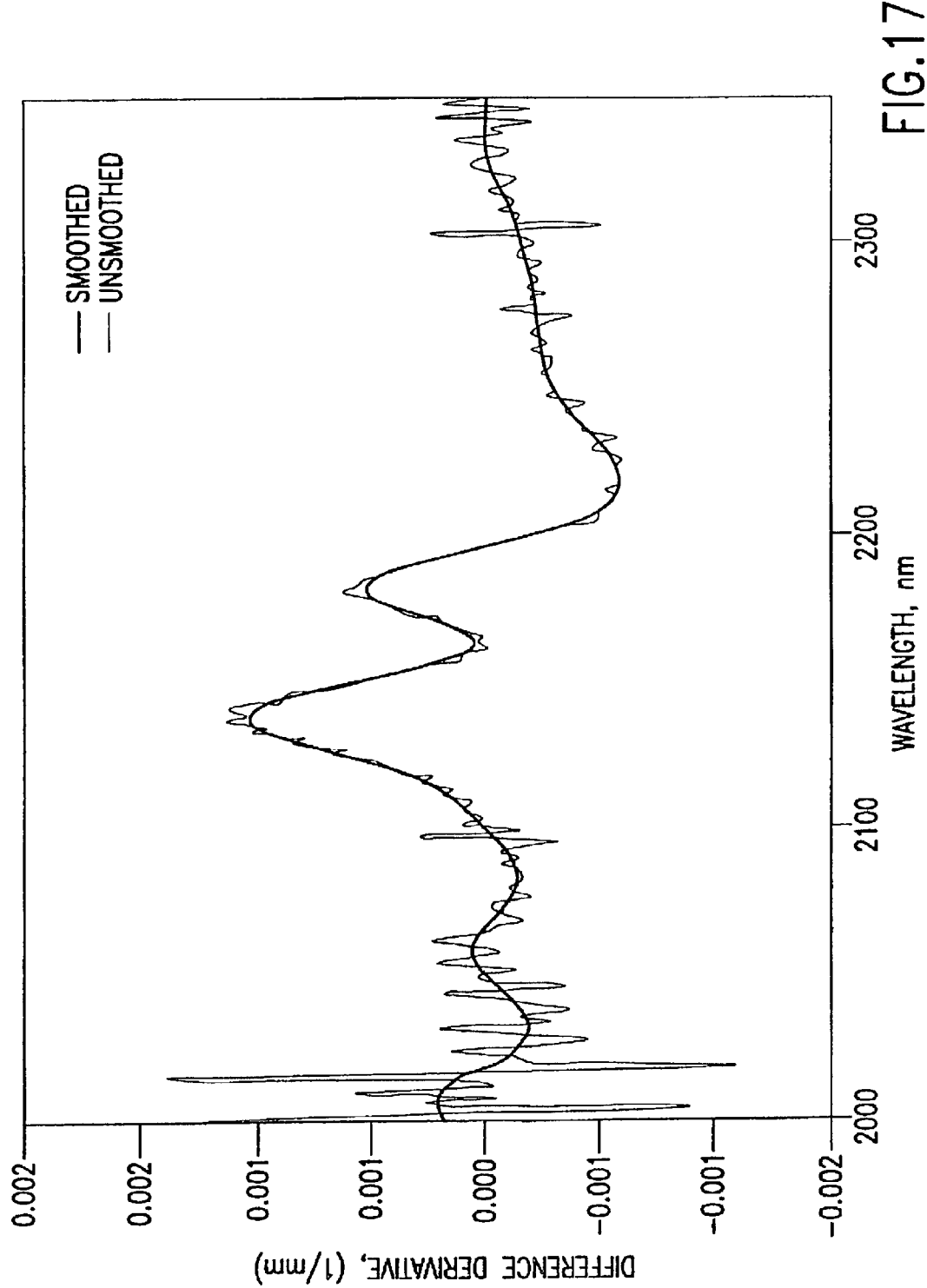
FIG. 17 is a graph showing the smoothed and non-smoothed spectra of urea at a concentration of 200 mg/dL.
Figure 18:
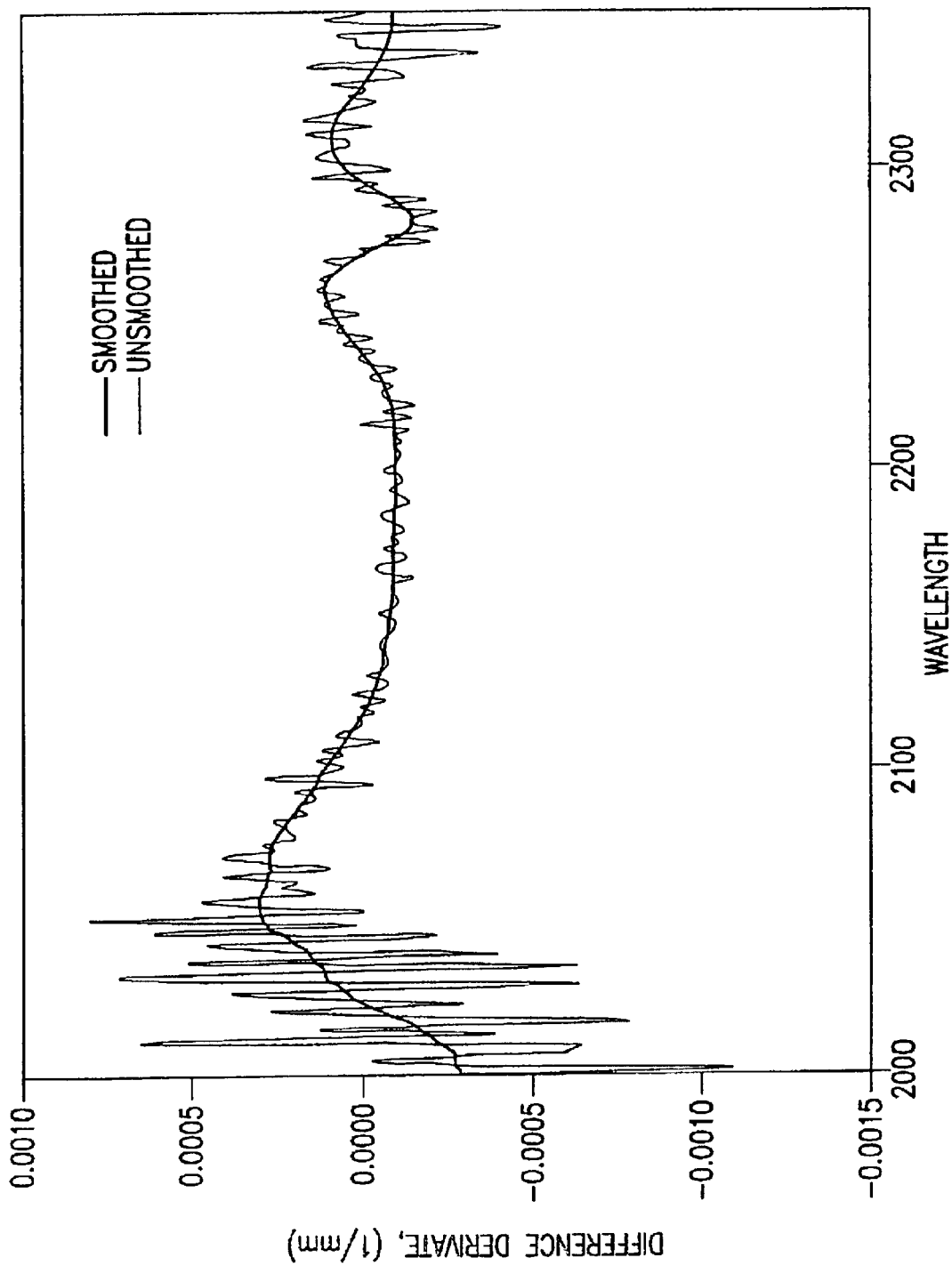
FIG. 18 is a graph showing the smoothed and non-smoothed spectra of glucose at a concentration of 100 mg/dL.
Figure 19:
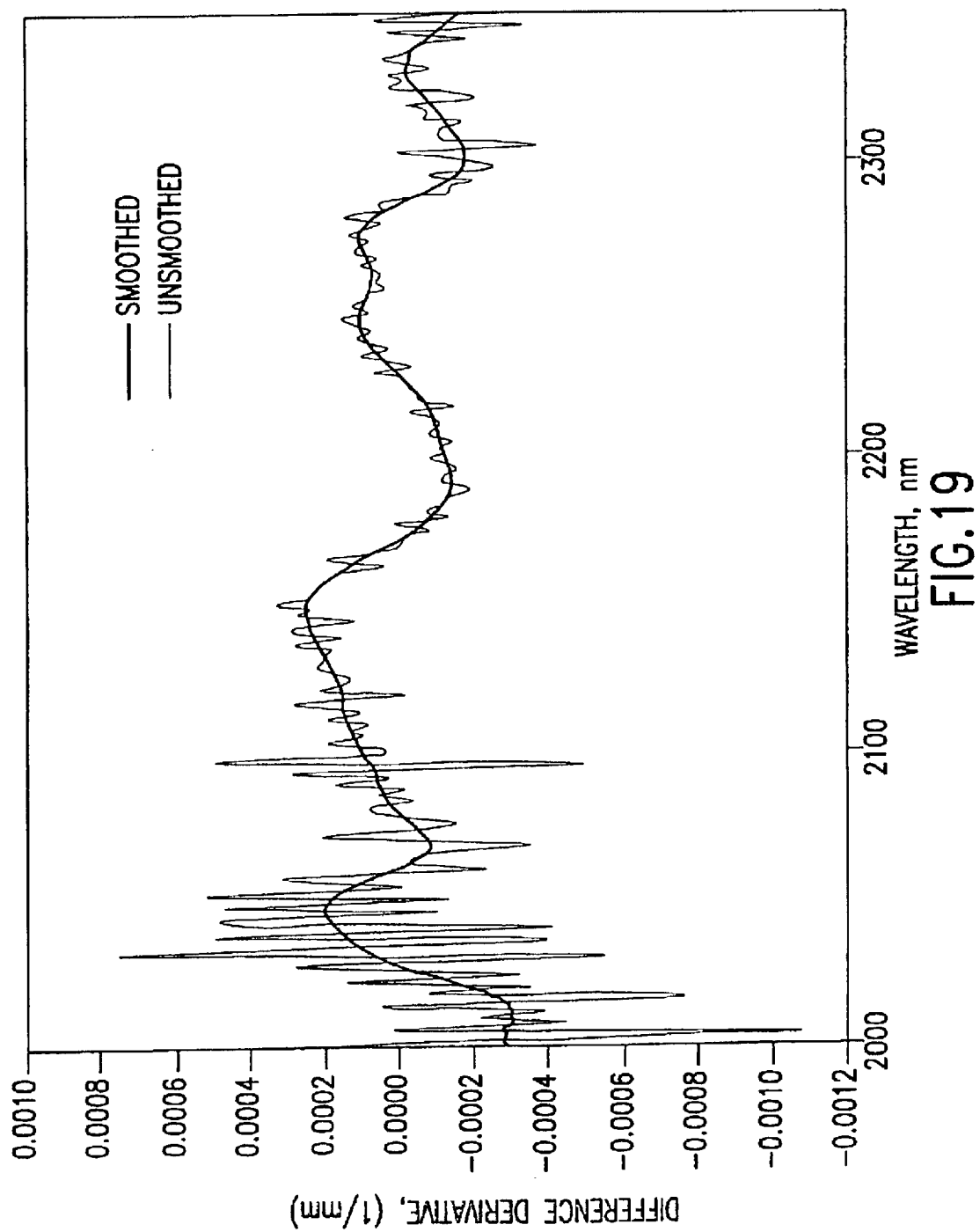
FIG. 19 is a graph showing the smoothed and non-smoothed spectra of albumin at a concentration of 50 mg/dL.

FIGS. 14 through 23 illustrate the second advantage to carrying out derivative spectroscopy. FIG. 14 shows the spectra of urea, creatinine, glucose, albumin, ketones, and nitrites after the absorption spectrum of water $c_w a_w$ has been subtracted. FIG. 14 was prepared by creating aqueous solutions of the above-mentioned analytes in water. The concentrations of the above-mentioned analytes are much greater than what would be expected in actual samples of urine, and the concentrations are shown at large values so that the spectral structure of these analytes can be observed. FIGS. 15 through 19 show the derivative spectra of the same six analytes individually or in combination for better comparison. FIG. 15 shows the derivative spectra of urea, creatinine, and glucose. FIG. 16 shows the derivative spectra of albumin, nitrites, and ketones. FIG. 17 shows the spectrum of urea at a concentration of 200 mg/dL. FIG. 18 shows the spectrum of glucose at a concentration of 100 mg/dL. FIG. 19 shows the spectrum of albumin at a concentration of 50 mg/dL. The second advantage of using the derivative spectroscopy is that the differences in the spectral structures between the analytes becomes more pronounced. As more unique features can be brought out of the spectral structure, the more specific the measurement of concentration of an analyte can be.

Figure 20:
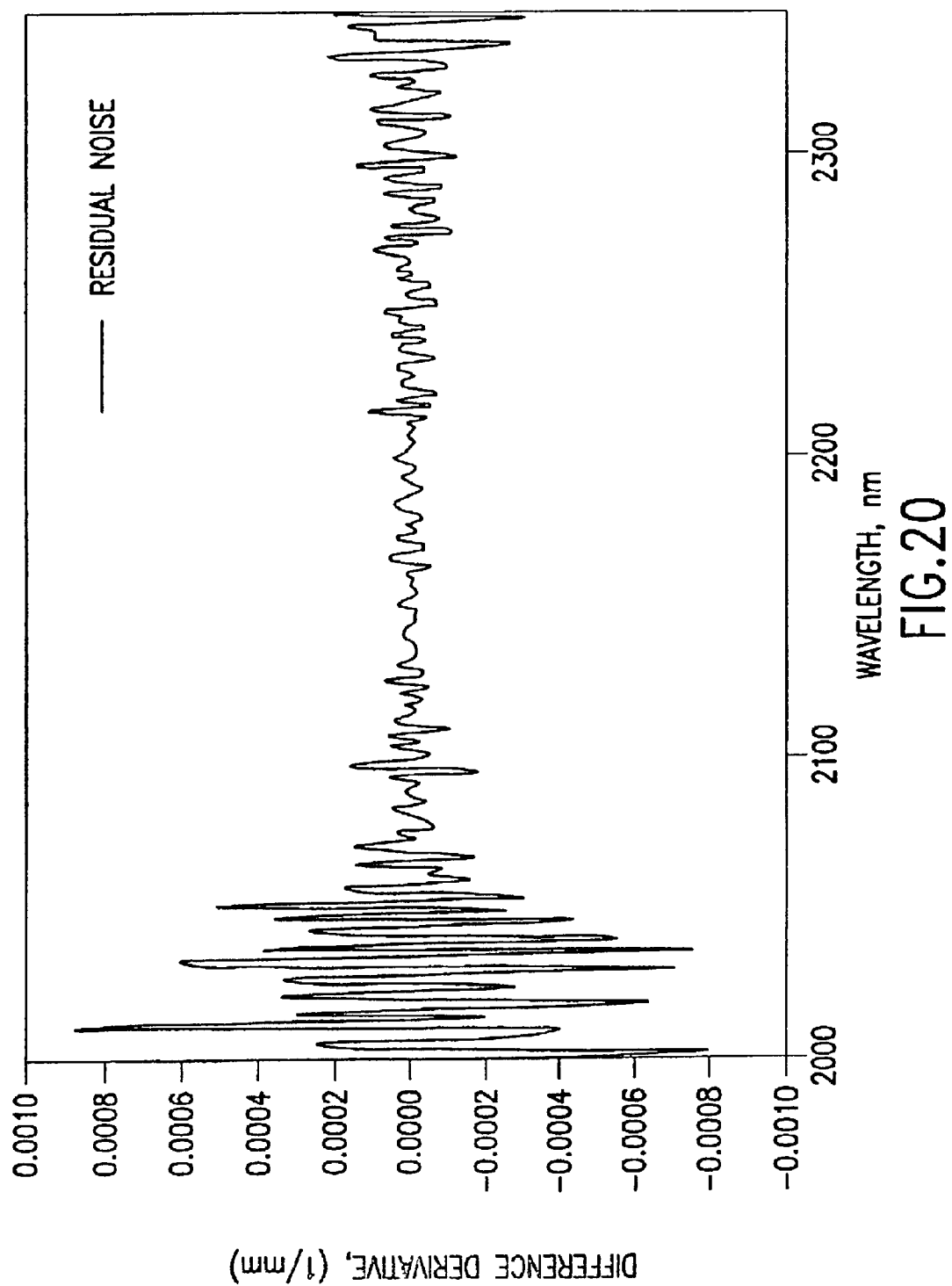
FIG. 20 is a graph showing typical residual noise of a spectrum of an analyte after the spectrum has been smoothed by means of a polynomial function.

In FIGS. 15 through 19, the concentrations of the analytes were sufficiently high and the magnitudes of the spectra sufficiently great that the noise extraneous to the signal was significantly smaller than the level of the signal. In clinical situations, however, the noise level for typical concentrations of these analytes is much larger relative to the signal strength. FIGS. 17 through 19 show spectra taken of urea, glucose, and albumin, respectively. These spectra were obtained using a state-of-the-art FTIR spectrometer optimized for measurements made in this wavelength range. Each figure shows the derivative spectrum and the smoothed derivative spectrum. FIG. 20 shows a typical spectrum of the noise that is removed from the derivative spectra with a polynomial noise reduction filter. That this noise spectrum is random can be established by visual inspection of the spectrum. Because (1) the magnitude is relatively small, (2) the values are distributed equally above and below zero, and (3) the average of the values approach zero, it can be assumed that the noise spectrum is random. There are other more sophisticated methods to ensure that the removed noise is random noise. One such method involves calculating the auto-correlation function. A single high peak at the origin of the auto-correlation function suggests that the noise is random noise.

The purpose of a noise reduction filter is to reduce the random noise superposed on the spectrum without distorting the spectral features associated with the analytes. A useful technique for this purpose is to use a mathematical function that would represent the spectral features while differentiating the random noise from the spectral features. There are several mathematical functions that can be used for this purpose. For example, a polynomial function, a Taylor series function, a Fourier series function, or a Gaussian function could approximate slowly varying spectral features. The random nature of the noise removed from the spectra in FIGS. 17 through 19 provides evidence that the features of the spectra have not been distorted. It has been discovered that the spectral features associated with the analytes can be approximated very well by a low order polynomial (e.g., a quadratic equation) over a small wavelength range. Preferably, the wavelength range has a width of from 1 nm to about 100 nm. In addition, the orders of the polynomial functions employed can be varied from spectral region to spectral region across the spectrum. The aforementioned spectral features can very often be represented by a quadratic equation. In other words, the spectral features associated with the analytes of interest in the infrared region have the form of a low order polynomial function, $$\alpha = x_0 + x_1\lambda + x_2\lambda^2 \qquad (13)$$

where

α represents absorption, $x_n$ where, n=0, 1, 2, are the coefficients, and

λ represents the wavelength.

It has been discovered that this equation provides an optimal fit for the infrared spectral region and that low order polynomials provide a suitable approximation of the underlying spectral feature that is to be observed.

The noise reduction method contemplated herein for the spectrum of a biological sample can be described by the following steps:

(a) identifying a mathematical function that is substantially similar to a region of a non-smoothed spectrum of the sample over a selected range of the non-smoothed spectrum;

(b) selecting a portion of the region of the non-smoothed spectrum such that noise in the selected portion is substantially random;

(c) determining coefficients of the mathematical function that result in a close fit of the function to the selected portion of the non-smoothed spectrum;

(d) calculating at least one value of the non-smoothed spectrum at at least one wavelength of the non-smoothed spectrum by means of the coefficients and the mathematical function of step (c), wherein said at least one wavelength includes the center of the region of the non-smoothed spectrum;

(e) assigning said at least one calculated value of the non-smoothed spectrum to a wavelength including the center of the selected portion of the region of the non-smoothed spectrum to form at least one point of a smoothed spectrum;

(f) shifting a selected distance in the non-smoothed spectrum and repeating steps (c), (d), and (e) until a desired amount of the smoothed spectrum is formed;

(g) forming a residual spectrum by subtracting each point of the desired amount of the smoothed spectrum at a given wavelength from each point of the non-smoothed spectrum at said given wavelength;

(h) inspecting the residual spectrum to determine if it is random; and (i) if the residual spectrum is not random, repeating steps (b), (c), (d), (e), (f), (g), and (h) to achieve a smoothing, wherein said residual spectrum is random.

In the foregoing method, the expression "close fit" means having little or no space between the measured spectrum and the selected mathematical function at a given wavelength. However, the closeness of fit is within the discretion of the user of the method and is not critical in the carrying out of the method of this invention. For example, the user can require that the fit of the selected mathematical function at any given wavelength be within 1%, 2%, 3%, 5%, 7%, 10%, or greater, of the measured value of the spectrum at that wavelength. The experience of the user, the requirements of the measurement, and the limitations of the computer are factors that should be considered in the selection of the closeness of fit. The expression "desired amount" is also within the discretion of the user of the method and is not critical in the carrying out of the method of this invention. For example, the user can require that the desired amount of the smoothed spectrum encompass a range based on the spectral feature of the analyte of interest and the convenience in carrying the computing steps. For example, in urinalysis, the desired amount could be the central 50% to 80% of the spectral range during the initial iteration of steps taken while searching for the optimal size of the spectral region for fitting. The desired amount could be the central 90% to 99% of the spectral range when verifying randomness and obtaining the final smoothed spectrum. The experience of the user, the requirements of the measurement, and the limitations of the computer are factors that should be considered in the selection of the desired amount of the spectrum that should be smoothed. Furthermore, the width of the portions used in the fitting of the mathematical function (or mathematical functions, if more than one mathematical function is employed) to the observed spectrum can be varied from spectral region to spectral region across the spectrum.

The method illustrated below is one procedure for determining a best fit to the spectral data to minimize the noise without distorting the spectral features that are to be observed. This method is a matrix operation for a least squares fit. Other procedures, such as a sum-and-difference method or a weighted least squares method can also be used.

In order to find the smoothed absorbance value $a_q$, a matrix $R_g$ is formed.

$$R_q = \begin{bmatrix} 1 & \lambda_{q-n/2} & \lambda_{q-n/2}^2 & \cdots & \lambda_{q-n/2}^l \\ 1 & \lambda_{q-n/2+1} & \lambda_{q-n/2+1}^2 & \cdots & \lambda_{q-n/2+1}^l \\ 1 & \vdots & \vdots & \vdots & \vdots \\ 1 & \lambda_q & \lambda_q^2 & \cdots & \lambda_q^l \\ 1 & \vdots & \vdots & \vdots & \vdots \\ 1 & \lambda_{q+n/2} & \lambda_{q+n/2}^2 & \cdots & \lambda_{q+n/2}^l \end{bmatrix}_{n+1,l+1} \qquad (14)$$

$$= \begin{bmatrix} r_{q-n/2} \\ r_{q-n/2+1} \\ \vdots \\ r_q \\ \vdots \\ r_{q+n/2} \end{bmatrix}$$

where n represents the number of wavelengths to be included in the fit, l represents the order of the polynomial that will be used in the fit, $\lambda_q^l$ represents the $q^{th}$ wavelength, of $l^{th}$ order, and $r_q$ represents the $q^{th}$ row vector in the $R_q$ matrix.

The number of wavelengths to be included in the fit can be chosen theoretically or empirically. Theoretically, a good rule of thumb is to use a number of wavelengths commonly used in a statistical analysis. For example, 20 data points are usually used for calculating the average value of a quantity under investigation. Empirically, a good number of wavelengths to be used can be found by searching through a range of numbers, such as from 10 to 30. Because this matrix operation is multi-dimensional, the search for optimal number of wavelengths can also be done in conjunction with the search for the order of polynomial function. A typical spectrum of a biological sample with wavelengths from the ultraviolet region to the visible region to the infrared region of the electromagnetic spectrum would include wavelengths from 190 nm to 40,000 nm. The number of wavelengths used would be 40 if 20 data points were used for fitting of a spectrum having a 2 nm step resolution.

The measured absorbance values are used to determine the coefficients of the polynomial by means of the following three equations:

$$\begin{bmatrix} a_{q-n/2} \\ a_{q-n/2+1} \\ \vdots \\ a_q \\ \vdots \\ a_{q+n/2} \end{bmatrix} = R_q \cdot \begin{bmatrix} x_0 \\ x_1 \\ x_2 \\ \vdots \\ x_l \end{bmatrix} \quad (15)$$

$$A_q = R_q \cdot X_q \quad (16)$$

$$X_q = [R_q^T \cdot R_q]^{-1} \cdot R_q^T \cdot A_q \quad (17)$$

where $X_q$ represents the $q^{th}$ set of polynomial coefficients, $[R_q^T \cdot R_q]^{-1} \cdot R_q^T$ represents the Pseudo-Inverse [see S. J. Leon, *Linear Algebra with Applications*, 2nd ed., Macmillan Publishing Company (1986)], and $A_q$ represents a column vector with the spectral absorbance centered at the $q^{th}$ wavelength, with n+1 elements.

The derivative spectrum can be smoothed in the same way. Higher order (second order and higher) derivatives can also be smoothed. The derivative spectra can also be determined directly from the smoothed absorbance spectra $$\frac{d}{d\lambda}\tilde{a}_q = \frac{d}{d\lambda}r_q \cdot X_q = \frac{d}{d\lambda}(x_0 + x_1\lambda + x_2\lambda^2 + \dots x_l\lambda^l) \quad (18)$$
$$= x_1 + 2x_2\lambda + \dots lx_{l-1}\lambda^{l-1}$$

A commonly used method for removing high frequency random variation is by averaging absorbance values that are neighbors to an absorbance value at a given wavelength. This method is known as box car averaging or running average smoothing. This method has the following disadvantages:

(a) reduction of peak height of spectral feature;

(b) distortion of spectrum by spreading spurious peak into wider area and smearing the distinction between spectral features and noise peaks, which could lead to incorrect results;

(c) coupling the averaged value of noise into the signal, which could contribute to run-to-run variation and adversely affect the calibration method.

Other methods such as low-pass Fourier filtering could work, but has the disadvantage that the basis functions of the Fourier transform do not resemble the features of the underlying spectrum, consequently requiring high order terms in the fit, which terms contain noise and require more data points to reduce the aliasing problem.

In a sample of urine, the analytes of interest include but are not limited to glucose, ketones, creatinine, albumin, nitrites, urea, bilirubin, hemoglobin, and urobilinogen. Each of these analytes are necessarily observed in a matrix containing many other analytes of varying concentration. The combination of the many analytes of no interest in the matrix makes up a background upon which the analyte of interest must be observed. Because of the large number of analytes in the background, the background may be varying and may be similar in structure to the spectral features of the analyte(s) of interest. Any useful data reduction method must be able to accurately quantify an analyte of interest, the signal of which may possibly be small in magnitude relative to the background.

Figure 21:
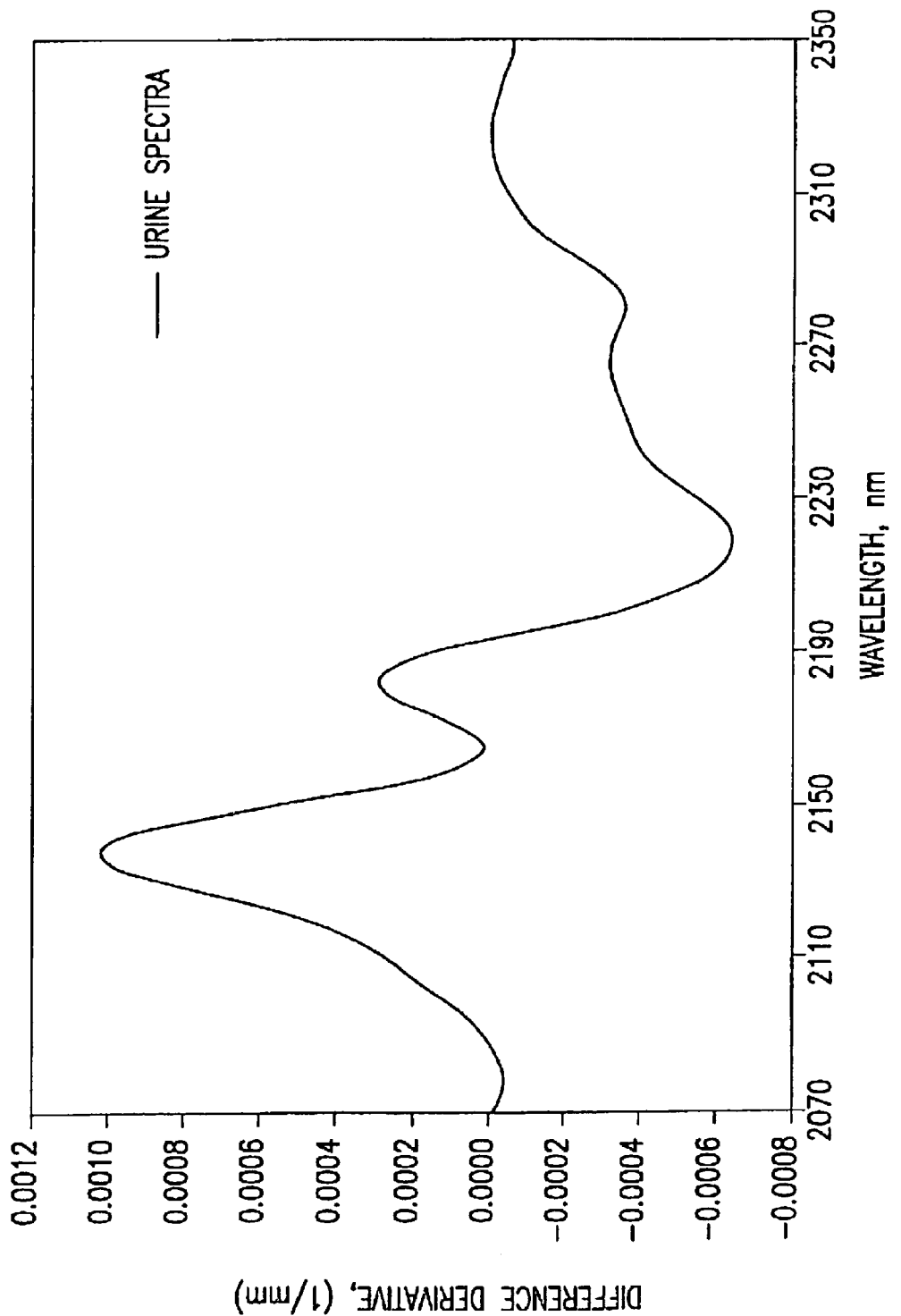
FIG. 21 is a graph showing a typical smoothed spectrum of a sample of urine.

FIG. 21 shows the derivative spectrum of a typical sample of urine. The derivative spectrum is determined from an absorption spectrum of urine, and then smoothed by means of the techniques previously described. The smoothed derivative spectrum of water has been subtracted from the smoothed derivative spectrum of urine. If it is assumed that the spectral features are due to urea, creatinine, glucose, albumin, ketones, and nitrites in this wavelength range, then the spectrum of urine should be, after subtracting the water background, $$S = L[c_U a_U + c_C a_C + c_G a_G + c_A a_A + c_K a_K + c_N a_N] \quad (19)$$

where $c_U a_U$, $c_C a_C$, $c_G a_G$, $c_A a_A$, $c_K a_K$, $c_N a_N$ represent the products of the concentrations and absorption spectra of urea, creatinine, glucose, albumin, ketones, and nitrites, respectively, and S and L are as previously defined.

Figure 22:
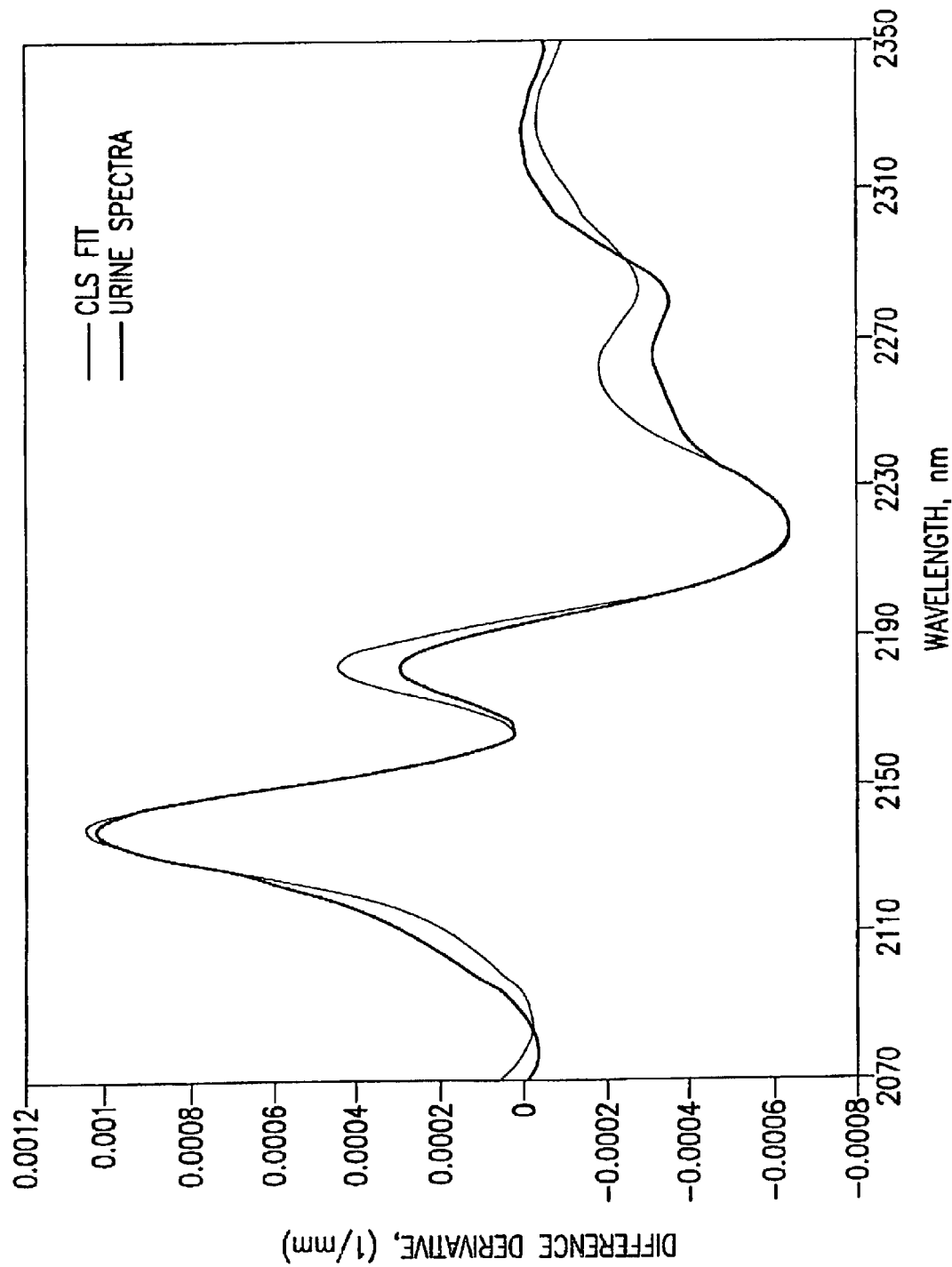
FIG. 22 is a graph showing both the spectrum of a sample of urine and a model spectrum consisting of the weighted spectra of six analytes commonly found in a urine sample.
Figure 23:
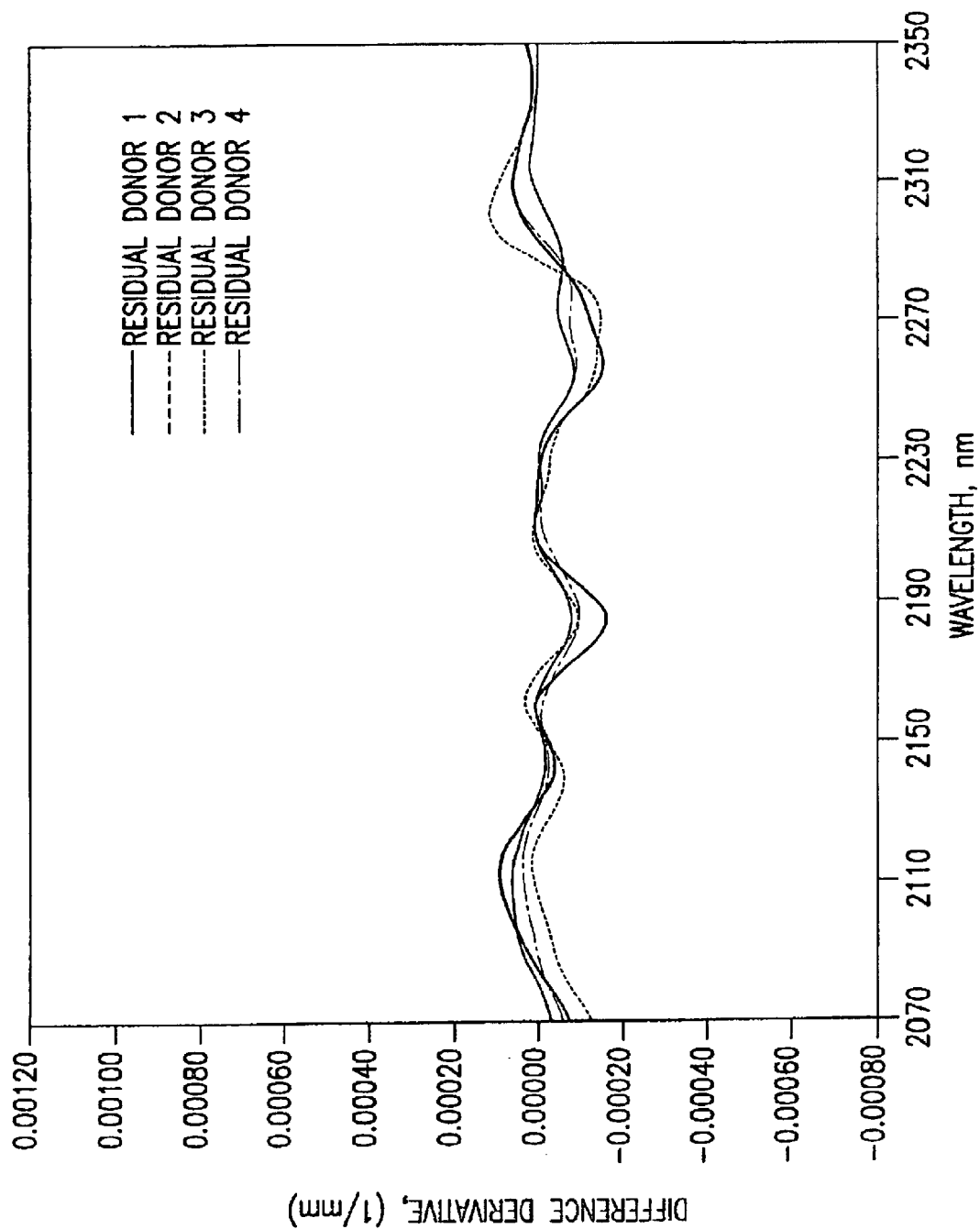
FIG. 23 is a graph showing the residual spectra from four different donors of samples of urine.
Figure 24:
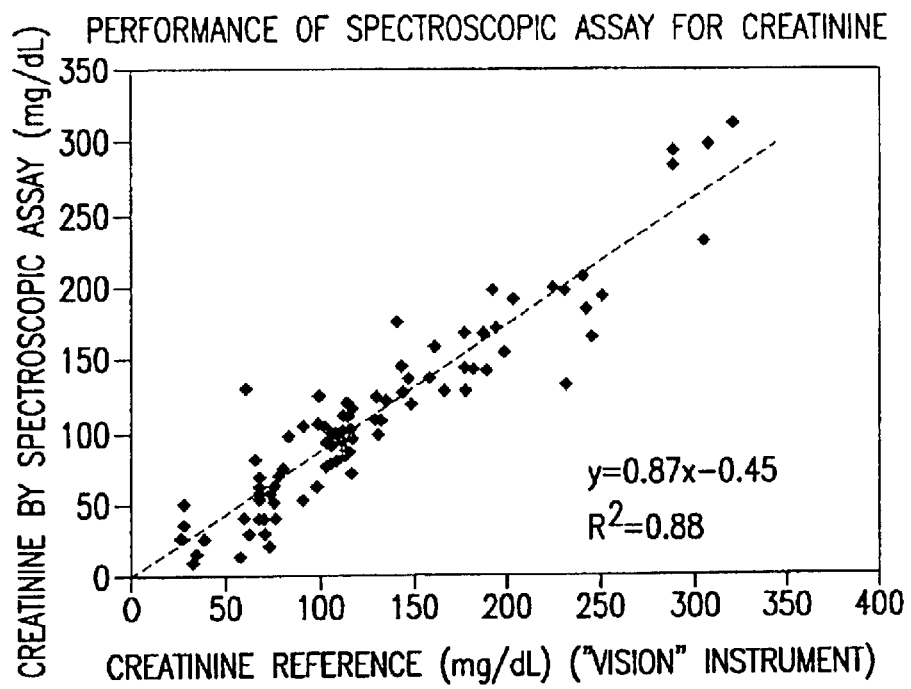
FIG. 24 is a graph showing the performance of a spectroscopic assay for creatinine.

By means of a classical least squares fit, the concentrations (represented by c's in the above equation) can be determined if the absorption spectra of the analytes of interest (represented by a's in the above equation) are known (by independent measurement in a calibration step). FIG. 22 shows the spectrum of urine along with the spectral fit S. The spectrum of urine and the spectral fit are not perfectly superposed, which means that additional analytes other than the six mentioned contribute to the spectral signature of urine. The difference between the spectral fit and the spectrum of urine is called the residual spectrum. If the residual spectrum is not equal to zero, it is assumed that additional analytes or noise or both have not been accounted for. FIG. 23 shows the residual spectra of samples of urine from four different patients.

The similarity of the residual spectra from the four different patients suggest that the residual spectrum is unlikely to be due to noise, because it is too consistent to be random. The residual spectrum is therefore more likely to be due to analytes other than urea, creatinine, glucose, albumin, ketones, and nitrites. Furthermore, this residual spectrum is very likely the result of summation of contributions from many different analytes, each present in a small amount. It is impractical to try to minimize the residual spectrum by including more and more minor analytes in the measurement, because the number of possibilities is too great. Furthermore, there is no need to have detailed account for the residual spectrum so long as the residual spectra are common among urine samples from different patients. Residual spectra can be compensated for by means of calibration.

The method of calibration must take into account the small fluctuations in the backgrounds. If the backgrounds from one person's urine to the next were completely different, then the ability to compensate for the fluctuating background would not be possible. However, it has been shown that this is not the case. Several mathematical tools are available to quantify small changes in spectral features in the presence of moderate changes in background signal. Among these tools are Partial Least Squares (PLS), Principle Component Analysis (PCA), Classical Least Squares (CLS), and Neural Networks.

The method contemplated herein for accounting for the residual spectrum in a biological sample can be described by the following steps:

(a) identifying at least one analyte that is a major component of said biological sample, said at least one analyte accounting for significant variations with respect to a plurality of spectra of biological samples from a plurality of donors of said biological samples;

(b) measuring a spectrum for each of the plurality of biological samples from the plurality of donors of the biological samples;

(c) calculating a model spectrum for each of the plurality of biological samples from the plurality of donors of the biological samples by mathematically fitting spectra of the analytes of the at least one identified analyte to each spectrum of each of the biological samples from the plurality of donors of the biological samples;

(d) calculating a residual spectrum for each spectrum of each of the biological samples from the plurality of donors of the biological samples by subtracting each value of the model spectrum from each value of the spectrum of the biological samples from the plurality of donors of the biological samples that corresponds to the model spectrum;

(e) repeating steps (a), (b), (c), and (d) at least one time by introducing at least one additional analyte to the model spectrum until the calculated residual spectra are substantially constant from one biological sample to another biological sample of the plurality of biological samples from the plurality of donors of the biological samples;

(f) determining a set of calibration parameters from the model spectra, said set of calibration parameters accounting for effects of said substantially constant residual spectra; and (g) using said calibration parameters to determine concentration of an analyte of interest in the sample of biological fluid of the individual.

In order to simplify the understanding of the aforementioned method, a typical determination will be described. In the case of a urine sample, five analytes can be identified as major components of a urine sample. These analytes are creatinine, urea, glucose, protein, and ketones. The spectrum for each of these five analytes, at unit concentration, are known. To simplify the determination, it can be assumed that three donors each provided a urine sample. The following symbols will be used to follow the determination to the desired result:

Cc represents the concentration of creatinine

Cu represents the concentration of urea

Cg represents the concentration of glucose

Cp represents concentration of protein

Ck represents the concentration of ketones

Sc represents the spectrum of creatinine at unit concentration

Su represents the spectrum of urea at unit concentration

Sg represents the spectrum of glucose at unit concentration

Sp represents the spectrum of protein at unit concentration

Sk represents the spectrum of ketones at unit concentration

S1 represents the spectrum of the urine sample from donor no. 1

S2 represents the spectrum of the urine sample from donor no. 2

S3 represents the spectrum of the urine sample from donor no. 3

MS1 represents the model spectrum of a urine sample from donor no. 1

MS2 represents the model spectrum of a urine sample from donor no. 2

MS3 represents the model spectrum of a urine sample from donor no. 3

RS1 represents the residual spectrum of a urine sample from donor no. 1

RS2 represents the residual spectrum of a urine sample from donor no. 2

RS3 represents the residual spectrum of a urine sample from donor no. 3

Ccn represents the concentration of creatinine in the urine sample from donor no. n, where n=1, 2, 3

Cun represents the concentration of urea in the urine sample from donor no. n, where n=1, 2, 3

Cgn represents the concentration of glucose in the urine sample from donor no. n, where n=1, 2, 3

Cpn represents concentration of protein in the urine sample from donor no. n, where n=1, 2, 3

Ckn represents the concentration of ketones in the urine sample from donor no. n, where n=1, 2, 3

Pcm represents a calibration parameter for creatinine in the urine sample of a test subject Pum represents a calibration parameter for urea in the urine sample of a test subject Pgm represents a calibration parameter for glucose in the urine sample of a test subject Ppm represents a calibration parameter for protein in the urine sample of a test subject Pkm represents a calibration parameter for ketones in the urine sample of a test subject Sc, Su, Sg, Sp, and Sk are control spectra. They are measured by spectrometry. S1, S2, and S3 are measured from the urine samples from the donors. The model spectra are calculated from the following equations:

$$MS1 = (Cc1 \times Sc) + (Cu1 \times Su) + (Cg1 \times Sg) + (Cp1 \times Sp) + (Ck1 \times Sk)$$

$$MS2 = (Cc2 \times Sc) + (Cu2 \times Su) + (Cg2 \times Sg) + (Cp2 \times Sp) + (Ck2 \times Sk)$$

$$MS3 = (Cc3 \times Sc) + (Cu3 \times Su) + (Cg3 \times Sg) + (Cp3 \times Sp) + (Ck3 \times Sk)$$

The coefficients Ccn, Cun, Cgn, Cpn, and Ckn can be the least squares fit of concentration creatine, urea, glucose, protein, and ketones, respectively, in the urine sample from donor no. n.

The residual spectra are calculated from the following equations:

$$RS1 = MS1 - S1$$

$$RS2 = MS2 - S2$$

$$RS3 = MS3 - S3$$

The foregoing calculations are repeated at least one time with at least one additional analyte until RS1, RS2, and RS3 are substantially equal. The calibration parameters can be obtained by means of mathematical operations, such as, for example, simultaneous equations, which can further employ techniques such as classical least squares, partial least squares, pseudo inverse matrix operations, neural networks, and the like. For example, Pc1, Pc2, and Pc3 can be obtained by a mathematical operation on MS1, MS2, and MS3 with respect to creatinine; Pg1, Pg2, and Pg3 can be obtained by a mathematical operation on MS1, MS2, and MS3 with respect to glucose; and so forth. The concentration of a given analyte in a urine sample from an actual test subject can be obtained by the operation on the spectrum of the sample. For example, Concentration of creatinine in sample=$[S(1) \times Pc1]+[S(2) \times Pc2]+[S(3) \times Pc3]+ \ldots +[S(m) \times Pcm]$ Concentration of glucose in sample=$[S(1) \times Pg1]+[S(2) \times Pg2]+[S(3) \times Pg3]+ \ldots +[S(m) \times Pgm]$ where m is the number of elements in the spectrum There is an optimal number of major components identified and accounted in an optical system. When that number is lower than the optimal number, the amount of variation remaining in the background is too great. When that number is greater than the optimal number, the system is costly to build and there is a risk in over-compensating for the background. One major feature of this invention is that the optimal number has been achieved with a fixed number of identified major components, thereby leading to a stable residual spectrum for many samples of urine. Therefore, the residual spectra in the calibration process can be accounted for in a manner similar to that used for subtracting a common background.

Operation

The operation of a system constructed for practicing this invention is uncomplicated. Referring now to FIGS. 2, 3, 4, 5, 6, 7, 8, and 9A, a biological sample, typically in the form of a liquid, e.g., urine, is introduced through the inlet port to fill the sample cell assembly and immerse the pH electrodes. The assemblies for carrying out the spectroscopic measurement and the refractive index measurement are activated and the measurements are read through the read zone of the sample cell assembly. pH is read simultaneously with the pH sensitive electrodes. All the foregoing steps of the operation are carried out under the control of a microprocessor. The methods of making the foregoing readings are well known to one of ordinary skill in the art. After the readings have been taken, the biological sample is expelled and the system is ready for the next sample. The microprocessor processes the data collected and reports the result either as concentration of an analyte of interest or as status of sample adulteration. FIGS. 24, 27, 28, and 29 show the results of the performance of spectroscopic assays for creatinine, glucose, nitrites, and urea, respectively.

There are at least two ways to expel the biological sample. The liquid sample can be pushed back through the inlet port to the original container or to a waste container. Alternatively, the liquid sample can be further drawn through the sample cell assembly through the outlet port to a waste container. The first way can employ a more compact instrument, especially when dispensing liquid back to its original container. The second way requires a waste container. Although the instrument might have to include additional weight to accommodate the waste container, it has the advantage over the first way in that the carry-over or cross-contamination problem is minimized.

Depending on the requirement for acceptable carry-over, there are several protocols for cleaning the sample cell assembly of the instrument of this invention. In some cases, such as in a high throughput screening operation, higher carry-over is tolerable as trade-off in favor of high-speed operation. Then, the residue from a previous sample can be cleaned by using part of the immediately succeeding sample as a cleaning solution. Passing greater volume of sample through the sample cell assembly can clean it by exchanging with the residue from the previous sample. However, this method of cleaning is not very effective due to the low exchange rate in a high flow rate situation. If even lower carry-over is desired, a protocol can be used to enhance the cleaning efficiency with the succeeding sample. In this protocol, a few pauses or a short backward flow motion of a pipetting process can be included in the step of loading the sample cell assembly with the sample through the inlet port. The reason that these additional motions are helpful in minimizing carry-over can be explained by principles of hydrodynamics. In a continuous flow situation, the affinity between the wall of a tube, e. g., the inlet tube, and the liquid causes the flow of liquid in the tube to be greater along the longitudinal axis of the tube than in any other area of the tube. This phenomenon is similar to the shear sheet flow of viscous liquid between two parallel plates in a hydrodynamics model. The slower flowing liquid clinging to the wall of the tube becomes a contaminant for the succeeding sample. To improve cleaning of the sample cell assembly, the shear sheet flow should be reduced to allow exchange of the fresh sample and the residue of the previous sample clinging to the wall of the tube. The additional pauses or backward flow motions can counter the hydrodynamics of the shear sheet flow of the sample inside both the tube and sample cell assembly. Less shear sheet flow will allow more effective mixing and therefore more thorough cleaning. The use of this protocol of a few pauses or a short backward flow motion typically results in a sample containing less than 0.01% of a previous sample. In cases where minimal carry-over is important, a washing buffer could be included to wash the line and sample cell assembly. Wash buffer can be introduced as blank sample between the liquid samples to provide additional washing of the instrument. Alternatively, another way, washing buffer can be introduced into the fluid line by means of a switching valve, thereby allowing high throughput.

The following non-limiting example will further illustrate the present invention.

EXAMPLE 1

This example illustrates an integrated system comprising a device that is capable of not only performing reagentless urinalysis but also of using reagents when desired. The reagentless urinalysis system can be coupled to a system that uses reagents to further exploit the advantages of the reagentless system. Protection of result integrity is a concern regardless of the diagnostic device employed. Result integrity could be compromised intentionally or unintentionally. Adulteration of urine samples for drug-of-abuse screening is an example of intentional attack on the result integrity by the sample provider. Dilution of a urine sample by means of alcoholic beverage consumption or diuretic medicine use is an example of unintentional compromise of result integrity. A marker, such as creatinine, which does not break down or is not significantly filtered by the kidney into urine, serves well for marking change of concentration of analyte as a function of change of urine volume. Thus, the ratio of the concentration of an analyte of interest to the concentration of creatinine is a better indicator than the concentration of the analyte of interest itself. For borderline cases where results could either be positive or negative, an analyte to creatinine ratio value would be very useful as tiebreaker to assign significance to the result.

In a simple embodiment, a reagentless urinalysis system can be fitted either to the front end of an analytical instrument or can be used as a parallel channel to the instrument. The front-end configuration could assay the analytes on desired markers and determine whether it is beneficial to expend the reagents for a clinical chemistry analysis. The results of a sample so screened would be expected to be accurate. Therefore, a front-end configuration provides the greatest economic benefit for reagent usage. However, such a configuration could delay the workflow, because screening and assaying are performed sequentially. If high throughput is desired and cost of reagent is of little concern, then parallel processing for both the adulteration marker and the analyte of interest would be more beneficial in term of reporting time. Results of analyte determination would be reported only if the adulteration channel indicated no adulteration. Reporting the ratio of the analyte of interest to creatinine along with determination of creatinine in the adulteration detection channel could be performed automatically.

In a more complicated embodiment, a reagentless urinalysis system could be modified to include a reagent-using module in an integrated unit. Such a unit would have the advantage of reagentless performance for most clinical chemistry analytes, while having the additional advantage of high sensitivity for analytes present in trace amounts or analytes having high specificity, such as those determined by immunoassay. For example, a reagentless urinalysis system combined with immunoassay for HCG could provide better quantitation for diagnosis of an abnormal type of pregnancy, ectopic pregnancy, where implantation occurred inside the Fallopian tube instead of inside the uterus, as it should be. As another example, a reagentless urinalysis system could be integrated with an assay for a given drug of abuse in a dedicated screening device for better reference and robust operation.

Figure 30A:
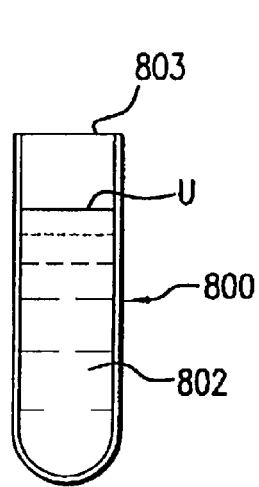
FIG. 30A is a schematic diagram illustrating a test tube containing a biological sample.
Figure 30B:
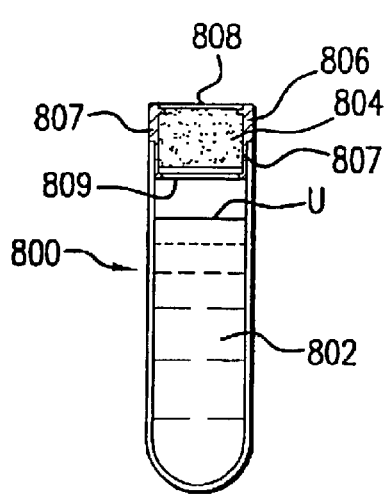
FIG. 30B is a schematic diagram illustrating dry reagent powder in asealed chamber in the cap of the test tube of FIG. 30A.
Figure 30C:
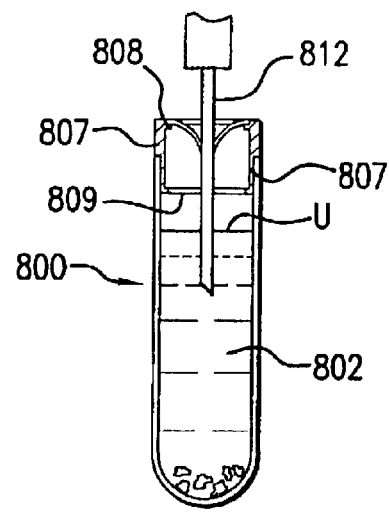
FIG. 30C is a schematic diagram illustrating a way of obtaining access to the dry reagent by piercing the sealed membrane on the cap so that the dry reagent can reach the sample in the lower portion of the test tube.

Several ways have been envisioned for integrating a system utilizing reagents with the reagentless system of this invention. As an example, in FIGS. 30A, 30B, and 30C, a reagent-using system comprises a container 800 having a receptacle portion 802 in which a chemical reaction can take place and a mouth 803 through which a biological sample can be introduced. In FIGS. 30A, 30B, and 30C, the container 800 is a test tube. The test tube can be a conventional test tube made from glass or a polymeric material. At least one reagent 804, which can be in liquid form or solid form, for a specific assay can be sealed in a cap 806, which cap can be used to seal the container 800. The cap 806 is of a size and a shape that it can be conveniently inserted into the mouth 803 of the container 800. The walls 807 of the cap 806 can be made from glass or a polymeric material, preferably an injection-molded polymeric material. The top 808 of the cap 806 can be made of a pierceable material, such as, for example, metallic foil, polymeric film, or rubber, and the bottom 809 of the cap 806 can be made of a rupturable material, such as, for example, frangible glass, metallic foil, or polymeric film. After the biological sample "U" is introduced into the container 800 and the cap 806 is sealed to the container 800, the container 800 is set in the assay instrument. A sampling probe 812 can pierce the top 808 of the sealed cap 806 and the shatter the bottom 809 of the sealed cap 806 to release the reagent 804 into the biological sample "U" in the receptacle portion 802 of the container 800. Additional mixing to ensure complete dispersion of the reagent into the biological sample can be accomplished by a few aspirating and dispensing operations of the probe to wash the area containing the reagent(s). The reaction mixture containing the biological sample and the reagent(s) can either be read through the receptacle 802 or transferred to a read chamber. A variation with dried reagent in the bottom of a sealed tube is also viable.

Figure 31:
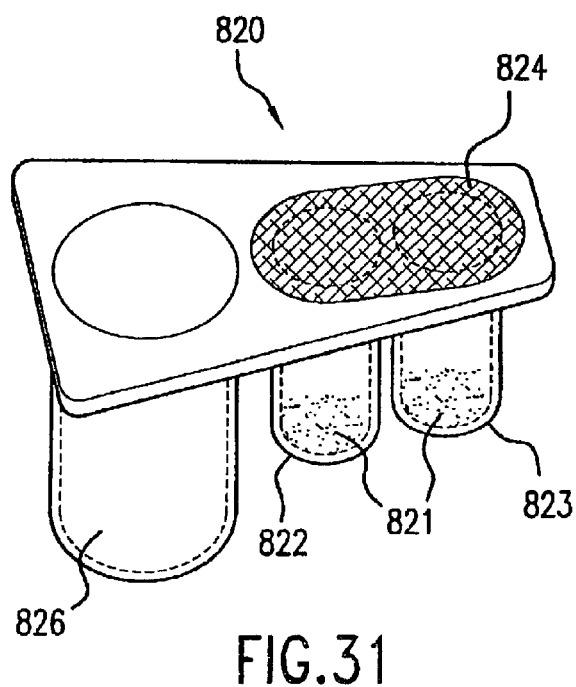
FIG. 31 is a schematic diagram of a test tube having a plurality of chambers for integrating the reagent-using option with the reagentless system of this invention.

In another example, as shown in FIG. 31, a container 820 contains at least one reagent 821, either in a dried form or in a liquid form, in receptacle portions 822, 823 which are sealed with a rupturable membrane 824. The rupturable membrane is preferably selected from glass, metallic foil, or polymeric film. Access to the reagent(s) can be achieved through the rupturable membrane 824 by a piercing probe (not shown). Dried reagent(s) can be reconstituted and the reconstituted reagent(s) can be transferred by means of pipetting to a receptacle portion 826 where the chemical reactions occur. Liquid reagents can be transferred by means of pipetting to the receptacle portion 826 where chemical reactions occur. The receptacle portions 822, 823 containing the reagent(s) can be physically separated from the receptacle portion 826 or they can be sub-compartments in a container 820 comprising a plurality of receptacle portions, as shown in FIG. 31.

In a still another embodiment, a reagentless read chamber could be fitted downstream of an automated analyzer that uses a reagent. After the chemical reaction with the reagent and the recording of its specific signals have occurred in an automated analyzer in a conventional manner, the reaction mixture is passed along to the reagentless read chamber, where the visible spectrum and the infrared spectrum can be collected. One caution in using this arrangement is that the reagent used in the automated analyzer should not have strong spectral features, because this would result in intererrence with the spectrum of the analyte of interest in the reagentless system.

EXAMPLE 2

This example illustrates an optical system and an integrated system for detection of nephropathy. A reagentless urinalysis system can be employed for many specific uses. One of such use involves detection of nephropathy in a diabetic patient. As indicators for complications to a diabetic condition, the monitoring of kidney function is essential. Urinary micro-albumin assay together with urinary creatinine is a commonly used tool for this monitoring. Such assays are usually performed in the physician's office as part of the quarterly or semi-annual check up of the diabetic patient. The two analytes, protein and creatinine, can be determined without reagents with the system of this invention. The system could employ infrared filter photometry. A few well-positioned filters at wavelengths ranging from 1900 to 2500 nm could determine albumin and creatinine and provide a useful ratio as an index for a nephropathy indicator. For screening where high precision is not necessary, a five-filter system can provide adequate performance. For monitoring where high precision is essential, more than five filters would be preferred for reducing noise and improving performance.

EXAMPLE 3

Figure 27:
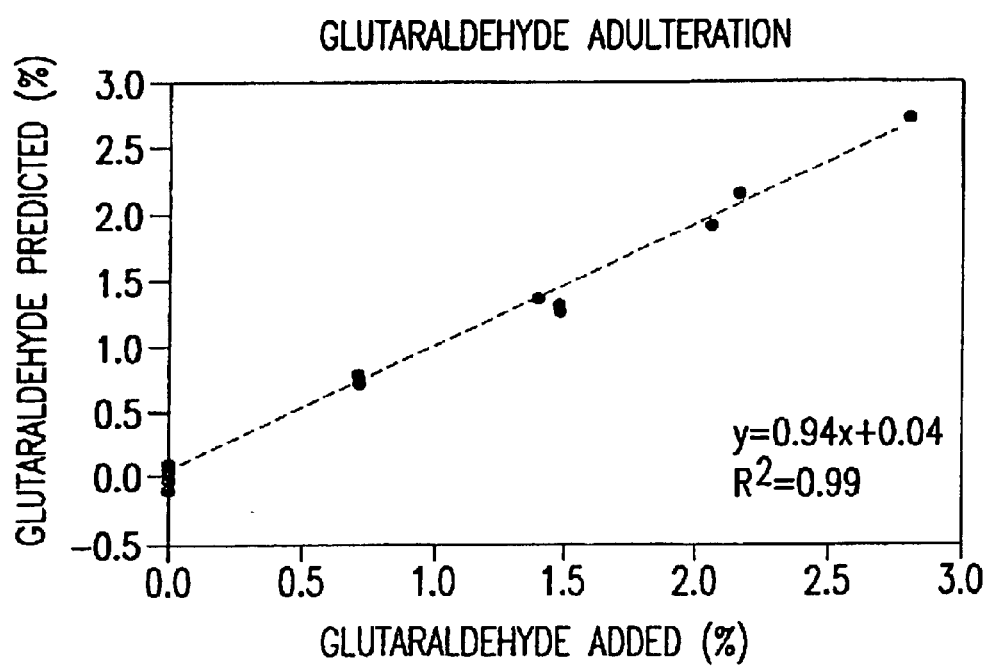
FIG. 27 is a graph showing the performance of a spectroscopic assay for glutaraldehyde.
Figure 28:
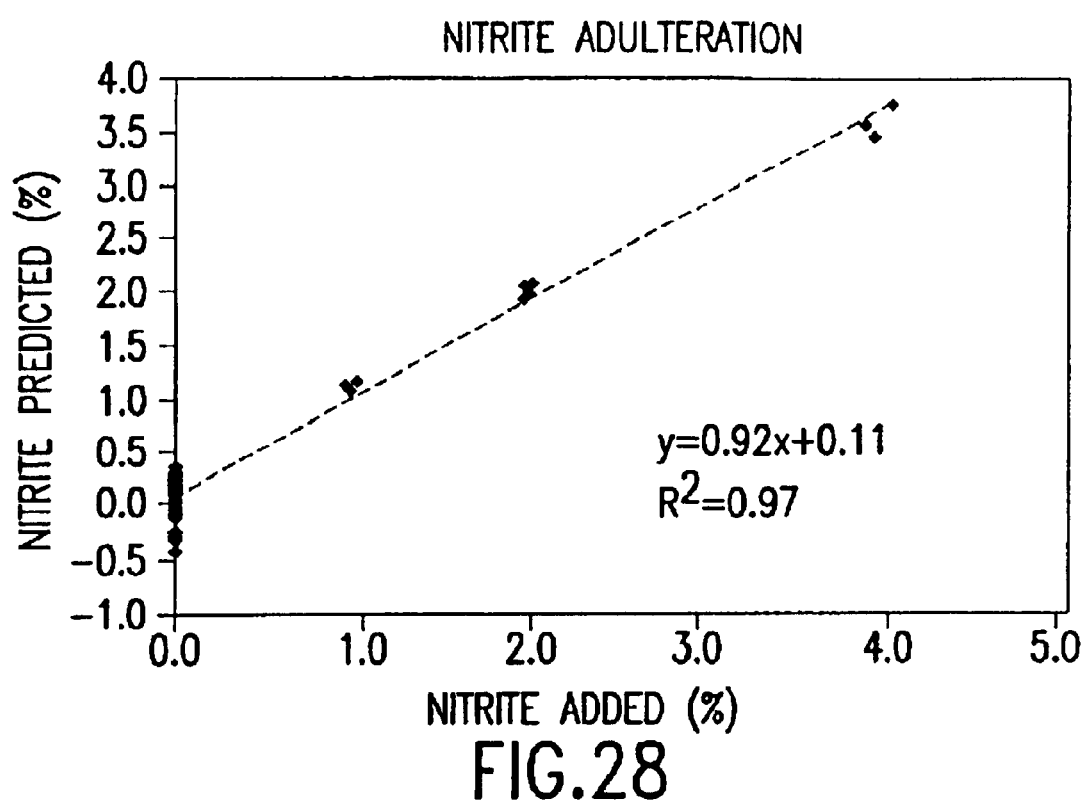
FIG. 28 is a graph showing the performance of a spectroscopic assay for nitrites.

This example illustrates an optical system and an integrated system for detection of urea in urine. Another specific use of a reagentless urinalysis system involves detection of urea in urine for monitoring kidney function for a diabetic patient. As an indicator for complications to a diabetic condition, monitoring of kidney function is essential. A high protein/low carbohydrate diet prescribed for a diabetic patients to control blood glucose level depends on the kidney function to remove urea and uric acid, which are byproducts of metabolizing a diet containing a high amount of protein. A high urinary urea concentration would be expected under these conditions. However, an overly long time of being subjected to a high protein diet tends to induce kidney damage. Therefore, it would be very useful for a diabetic patient to check urinary urea level periodically and to adjust his diet to have more fiber and liquid to relieve the stress induced by a high protein diet. A few well-positioned filters at wavelengths ranging from 1900 to 2500 nm can be used to determine urea concentration accurately and precisely. A simplified version of a system using infrared derivative spectroscopy would be sufficient for this purpose. A multiple function integrated apparatus incorporating measurement of urea, creatinine, protein, and other analytes would also be useful for the diabetic patient. FIG. 27 is a diagram illustrating the performance of a reagentless urea assay on a sample of urine. The reference value was obtained by using diluted urine on a "VISION" instrument. The reagentless method and apparatus of this invention showed good performance with good precision and high correlation to the reference method.

EXAMPLE 4

Figure 32:
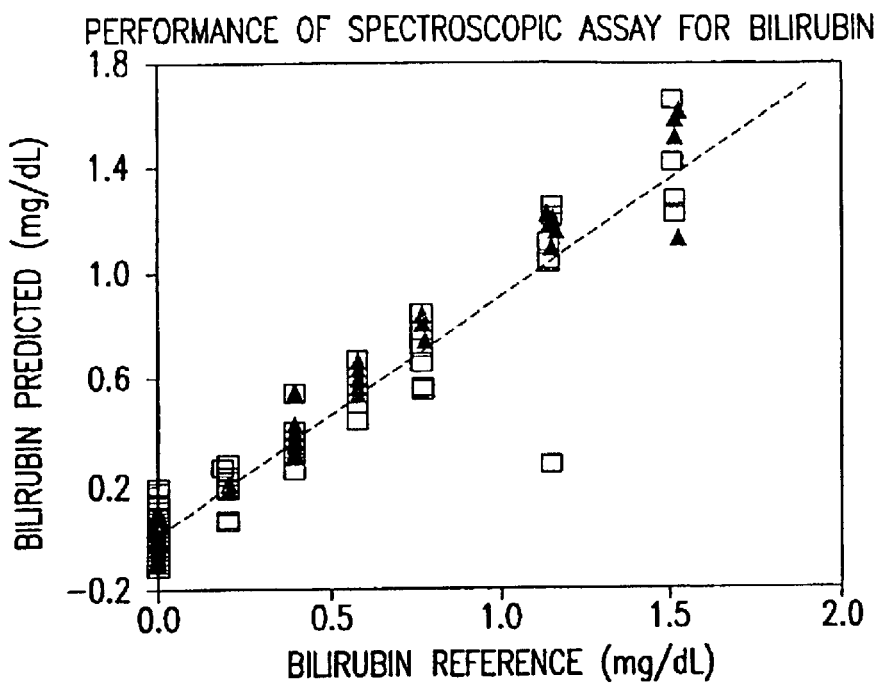
FIG. 32 is a graph showing the performance of a spectroscopic assay for bilirubin.
Figure 33:
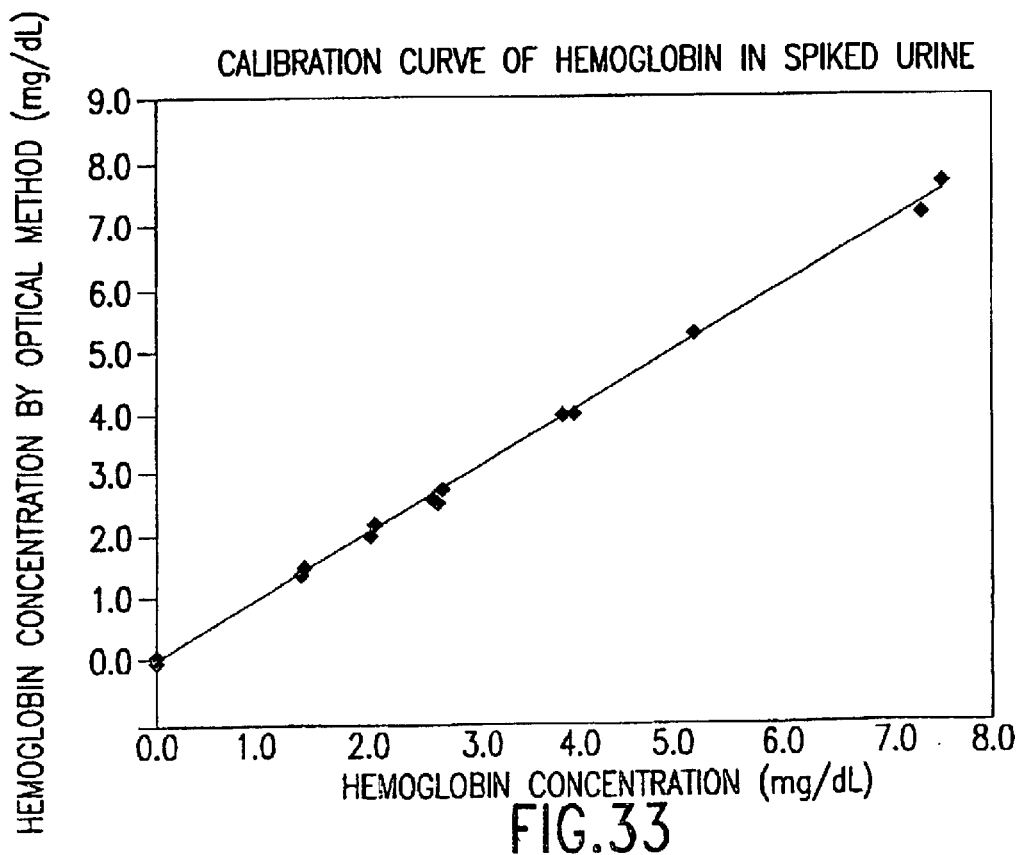
FIG. 33 is a graph showing the performance of a spectroscopic assay for hemoglobin.

This example illustrates an optical system and an integrated system for urinary bilirubin determination for newborn. Another specific use for a reagentless urinalysis system for determination of urinary bilirubin involves monitoring hemolytic jaundice in the newborn. Significant numbers of newborn babies suffer from excess bilirubin due to an immune response to the blood type of the mother. Excess hemolytic reaction produces a significantly high level of bilirubin, which could adversely affect the development of the baby. A blood bilirubin assay is usually used to monitor the development. The urinary bilirubin assay is non-invasive in nature. Urinary bilirubin measurements are painless to the baby and would be less likely to cause concern or heartache to the baby's parents. An optical device having continuous monitoring capability could track the clearance of bilirubin from the baby's system effectively. A simplified version of an instrument using visible light derivative spectroscopy would be sufficient for this purpose. A multiple function integrated apparatus incorporating measurement of creatinine, protein, hemoglobin, and other analytes could also be useful for additional information for tracking the baby's development. FIG. 32 is a diagram illustrating the performance of the reagentless bilirubin assay in urine samples. FIG. 33 illustrates the performance of an assay for hemoglobin in urine samples. The reference values were obtained by gravimetric spiking of bilirubin or hemoglobin into base urine samples. The reagentless optical method showed good recovery of the spiked amount with high precision.

EXAMPLE 5

This example illustrates a smoothing process for reducing noise in an absorption spectroscopy measurement. For simplicity, only a small segment of a spectrum of an actual urine sample was used. The wavelength range of this example begins at 450 nm and ends at 508 nm. The data involved 30 points. The wavelength increment between neighboring data points was 2 nm. A region comprising 15 data points and encompassing a spectral width of 30 nm was chosen for fitting. The fitting function in this example was a polynomial function of second order, namely, a quadratic equation as shown in equation (13) above. In Table I, the first column lists the sequence number of each data point used. Table I shows the wavelength in the second column and raw data of absorbance, recorded with a commercially available spectrometer, in the third column. The numbered position of each column is read from left to right. The next six columns in Table I exemplify the values in the matrix to be used in the pseudo inverse operation that was set forth in equations (14), (15), (16), and (17), except each column has been displaced downward three rows to illustrate its relationship to the original raw data. The three-row shift in this example corresponds to a three data point contribution for the smoothed spectrum from each portion of raw data. The coefficients of the second order polynomial function based on a least squares fit to each selected portion of raw data is shown in Table II. The value of the fitted second order polynomial function for each portion of spectrum listed Table I was calculated with the corresponding coefficients and is shown in the corresponding column in Table III. A smoothed spectrum, formed by collecting three data points from each spectral portion is shown in the tenth column of Table III. The residual spectrum, i. e., the difference of the smoothed spectrum and the non-smoothed spectrum, is shown in the eleventh column in Table III. This residual spectrum represents the high frequency random noise. That this spectrum represents high frequency random noise can be is confirmed in two ways: (1) absolute value for each data point in the residual spectrum is low, and (2) the averaged value for all the data points in the residual spectrum, as shown in last row of Table III, is close to zero. Random variation would be expected to provide a measured value having about an equal chance of being higher or lower than true value, and the average of the differences should approach zero.

TABLE I

| Seq. No. | Wave-length (nm) | Absorb-ance Raw Data | Portions of Spectral Region for Fitting with Selected Mathematical Function | | | | | |
|---|---|---|---|---|---|---|---|---|
| | | | 1st | 2nd | 3rd | 4th | 5th | 6th |
| 1 | 450 | 1.0469 | 1.0469 | | | | | |
| 2 | 452 | 1.0148 | 1.0148 | | | | | |
| 3 | 454 | 0.9855 | 0.9855 | | | | | |
| 4 | 456 | 0.9582 | 0.9582 | 0.9582 | | | | |
| 5 | 458 | 0.9327 | 0.9327 | 0.9327 | | | | |
| 6 | 460 | 0.9066 | 0.9066 | 0.9066 | | | | |

TABLE I-continued

| Seq. No. | Wave-length (nm) | Absorb-ance Raw Data | Portions of Spectral Region for Fitting with Selected Mathematical Function | | | | | |
|---|---|---|---|---|---|---|---|---|
| | | | 1st | 2nd | 3rd | 4th | 5th | 6th |
| 7  | 462 | 0.8846 | 0.8846 | 0.8846 | 0.8846 |        |        |        |
| 8  | 464 | 0.8608 | 0.8608 | 0.8608 | 0.8608 |        |        |        |
| 9  | 466 | 0.8383 | 0.8383 | 0.8383 | 0.8383 |        |        |        |
| 10 | 468 | 0.8174 | 0.8174 | 0.8174 | 0.8174 | 0.8174 |        |        |
| 11 | 470 | 0.7972 | 0.7972 | 0.7972 | 0.7972 | 0.7972 |        |        |
| 12 | 472 | 0.7770 | 0.7770 | 0.7770 | 0.7770 | 0.7770 |        |        |
| 13 | 474 | 0.7565 | 0.7565 | 0.7565 | 0.7565 | 0.7565 | 0.7565 |        |
| 14 | 476 | 0.7375 | 0.7375 | 0.7375 | 0.7375 | 0.7375 | 0.7375 |        |
| 15 | 478 | 0.7183 | 0.7183 | 0.7183 | 0.7183 | 0.7183 | 0.7183 |        |
| 16 | 480 | 0.6999 |        | 0.6999 | 0.6999 | 0.6999 | 0.6999 | 0.6999 |
| 17 | 482 | 0.6821 |        | 0.6821 | 0.6821 | 0.6821 | 0.6821 | 0.6821 |
| 18 | 484 | 0.6670 |        | 0.6670 | 0.6670 | 0.6670 | 0.6670 | 0.6670 |
| 19 | 486 | 0.6445 |        |        | 0.6445 | 0.6445 | 0.6445 | 0.6445 |
| 20 | 488 | 0.6282 |        |        | 0.6282 | 0.6282 | 0.6282 | 0.6282 |
| 21 | 490 | 0.6110 |        |        | 0.6110 | 0.6110 | 0.6110 | 0.6110 |
| 22 | 492 | 0.5938 |        |        |        | 0.5938 | 0.5938 | 0.5938 |
| 23 | 494 | 0.5755 |        |        |        | 0.5755 | 0.5755 | 0.5755 |
| 24 | 496 | 0.5581 |        |        |        | 0.5581 | 0.5581 | 0.5581 |
| 25 | 498 | 0.5406 |        |        |        |        | 0.5406 | 0.5406 |
| 26 | 500 | 0.5222 |        |        |        |        | 0.5222 | 0.5222 |
| 27 | 502 | 0.5046 |        |        |        |        | 0.5046 | 0.5046 |
| 28 | 504 | 0.4883 |        |        |        |        |        | 0.4883 |
| 29 | 506 | 0.4720 |        |        |        |        |        | 0.4720 |
| 30 | 508 | 0.4572 |        |        |        |        |        | 0.4572 |

TABLE II

|       | 1st      | 2nd       | 3rd       | 4th       | 5th       | 6th       |
|-------|----------|-----------|-----------|-----------|-----------|-----------|
| $x_0$ | 29.786   | 23.068    | 16.699    | 11.868    | 7.1635    | 8.6609    |
| $x_1$ | −0.1131  | −0.0844   | −0.0574   | −0.0372   | −0.0178   | −0.024    |
| $x_2$ | 0.000109 | 0.00007875| 0.00005015| 0.00002903| 0.00000903| 0.00001545|

TABLE III

| Seq. No. | Wave-length (nm) | Raw Data | Fitted Values of Selected Portions of Spectral Region | | | | | | Smoothed | Residual |
|---|---|---|---|---|---|---|---|---|---|---|
| | | | 1st | 2nd | 3rd | 4th | 5th | 6th | | |
| 1  | 450 | 1.0469 | 1.0445 |        |        |        |        |        |        |         |
| 2  | 452 | 1.0148 | 1.0157 |        |        |        |        |        |        |         |
| 3  | 454 | 0.9855 | 0.9877 |        |        |        |        |        |        |         |
| 4  | 456 | 0.9582 | 0.9606 | 0.9566 |        |        |        |        |        |         |
| 5  | 458 | 0.9327 | 0.9344 | 0.9317 |        |        |        |        |        |         |
| 6  | 460 | 0.9066 | 0.9090 | 0.9075 |        |        |        |        |        |         |
| 7  | 462 | 0.8846 | 0.8846 | 0.8839 | 0.8844 |        |        |        | 0.8846 | −0.0001 |
| 8  | 464 | 0.8608 | 0.8610 | 0.8610 | 0.8625 |        |        |        | 0.8610 | 0.0002  |
| 9  | 466 | 0.8383 | 0.8383 | 0.8386 | 0.8410 |        |        |        | 0.8383 | −0.0001 |
| 10 | 468 | 0.8174 | 0.8164 | 0.8169 | 0.8199 | 0.8164 |        |        | 0.8169 | −0.0004 |
| 11 | 470 | 0.7972 | 0.7955 | 0.7959 | 0.7991 | 0.7965 |        |        | 0.7959 | −0.0014 |
| 12 | 472 | 0.7770 | 0.7754 | 0.7754 | 0.7788 | 0.7768 |        |        | 0.7754 | −0.0016 |
| 13 | 474 | 0.7565 | 0.7562 | 0.7556 | 0.7589 | 0.7573 | 0.7551 |        | 0.7589 | 0.0024  |
| 14 | 476 | 0.7375 | 0.7378 | 0.7365 | 0.7394 | 0.7381 | 0.7367 |        | 0.7394 | 0.0019  |
| 15 | 478 | 0.7183 | 0.7203 | 0.7179 | 0.7203 | 0.7191 | 0.7183 |        | 0.7203 | 0.0019  |
| 16 | 480 | 0.6999 |        | 0.7000 | 0.7016 | 0.7003 | 0.7000 | 0.7006 | 0.7003 | 0.0003  |
| 17 | 482 | 0.6821 |        | 0.6827 | 0.6832 | 0.6817 | 0.6818 | 0.6823 | 0.6817 | −0.0004 |
| 18 | 484 | 0.6670 |        | 0.6661 | 0.6653 | 0.6634 | 0.6636 | 0.6642 | 0.6634 | −0.0036 |
| 19 | 486 | 0.6445 |        |        | 0.6478 | 0.6453 | 0.6455 | 0.6461 | 0.6455 | 0.0010  |
| 20 | 488 | 0.6282 |        |        | 0.6307 | 0.6275 | 0.6275 | 0.6282 | 0.6275 | −0.0007 |
| 21 | 490 | 0.6110 |        |        | 0.6140 | 0.6099 | 0.6096 | 0.6104 | 0.6096 | −0.0014 |
| 22 | 492 | 0.5938 |        |        |        | 0.5925 | 0.5917 | 0.5928 | 0.5928 | −0.0010 |
| 23 | 494 | 0.5755 |        |        |        | 0.5753 | 0.5739 | 0.5753 | 0.5753 | −0.0002 |
| 24 | 496 | 0.5581 |        |        |        | 0.5584 | 0.5562 | 0.5578 | 0.5578 | −0.0003 |
| 25 | 498 | 0.5406 |        |        |        |        | 0.5386 | 0.5406 |        |         |
| 26 | 500 | 0.5222 |        |        |        |        | 0.5210 | 0.5234 |        |         |
| 27 | 502 | 0.5046 |        |        |        |        | 0.5035 | 0.5064 |        |         |
| 28 | 504 | 0.4883 |        |        |        |        |        | 0.4894 |        |         |

TABLE III-continued

| Seq. No. | Wavelength (nm) | Raw Data | Fitted Values of Selected Portions of Spectral Region | | | | | | Smoothed | Residual |
|---|---|---|---|---|---|---|---|---|---|---|
| | | | 1st | 2nd | 3rd | 4th | 5th | 6th | | |
| 29 | 506 | 0.4720 | | | | | | 0.4727 | | |
| 30 | 508 | 0.4572 | | | | | | 0.4560 | | |
| | | | | | | | | | Average = | −0.00018 |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for (a) determining concentration of at least one analyte of interest in a biological sample by means of a spectroscopic analysis and (b) measuring refractive index of said biological sample, said method comprising the steps of:
   (a) providing a beam of light for a spectroscopic measurement;
   (b) providing a beam of light for a refractive index measurement, said beam of light for said spectroscopic measurement and said beam of light for said refractive index measurement beam not being co-linear;
   (c) providing a sample cell assembly for containing a biological sample to be used in determining concentration at least one analyte in said biological sample, said sample cell assembly comprising:
      (1) a port into which said biological sample can be introduced into the sample cell assembly;
      (2) said port of (a) communicating with an expansion zone;
      (3) said expansion zone communicating with a read zone;
      (4) said read zone communicating with a contraction zone;
      (5) said contraction zone communicating with a port from which said biological sample can be removed from said sample cell assembly;
      (6) a first pair of windows; and
      (7) a second pair of windows, said second pair of windows comprising a first window having two major surfaces and a second window having two major surfaces, said major surfaces of said first window not being parallel to said major surfaces of said second window.
   (d) introducing a biological sample into said sample cell assembly;
   (e) introducing said beam of light for said spectroscopic measurement into said sample;
   (f) introducing said beam of light for said refractive index measurement into said sample;
   (g) detecting said beam of light for said spectroscopic measurement emerging from said sample;
   (h) detecting said beam of light for said refractive index measurement emerging from said sample;
   (i) determining concentration of said analyte from said detected beam of light for said spectroscopic measurement;
   (h) determining said refractive index of said sample from said detected beam of light for said refractive index measurement.

2. The method claim 1, wherein said biological sample is a fluid.

3. The method of claim 2, wherein said biological sample is selected from the group consisting of urine, whole blood, plasma, serum, sputum, saliva, sweat, interstitial fluid, cerebral spinal fluid, and dialysate obtained in kidney dialysis.

4. The method claim 1, wherein said biological sample is urine.

5. The method of claim 4, wherein said at least one analyte of interest is selected from the group consisting of urea, creatinine, protein, glucose, and ketones.

6. The method of claim 4, wherein said at least one analyte of interest is selected from the group consisting of hemoglobin and bilirubin.

7. The method of claim 1, wherein said spectroscopic analysis is selected from the group consisting of ultraviolet absorption spectroscopy, visible absorption spectroscopy, infrared absorption spectroscopy, ultraviolet scattering spectroscopy, visible scattering spectroscopy, infrared scattering spectroscopy, fluorescence spectroscopy, and Raman spectroscopy.

8. The method of claim 1, wherein said spectroscopic analysis is filter photometry.

9. The method of claim 1, wherein said spectroscopic analysis is derivative spectroscopy.

10. The method of claim 1, wherein said spectroscopic analysis utilizes measurement of transmitted light.

11. The method of claim 1, wherein said spectroscopic analysis utilizes measurement of reflected light.

12. The method of claim 1, wherein said beam of light for said refractive index measurement is perpendicular to said beam of light for said spectroscopic measurement.

13. The method of claim 1, wherein the wavelength of said beam of light for said refractive index measurement ranges from about 500 nm to about 1000 nm.

14. The method of claim 1, wherein the wavelength of said beam of light for said spectroscopic measurement ranges from about 300 nm to about 2500 nm.

15. The method of claim 1, further including the step of employing at least one measurement selected from the following additional measurements: light scattering, impedance, pH, ion, and temperature.

* * * * *